US007612173B2

(12) United States Patent
Abrecht et al.

(10) Patent No.: US 7,612,173 B2
(45) Date of Patent: Nov. 3, 2009

(54) VACCINE FOR PREVENTION AND TREATMENT OF HIV-INFECTION

(75) Inventors: Helge Abrecht, Rixensart (BE); Martine Delchambre, Rixensart (BE); Martine Marchand, Rixensart (BE); Nathalie Louise Mathy, Rixensart (BE); Philippe Jean Gervais Ghislain Permanne, Rixensart (BE); Gerald Hermann Voss, Rixensart (BE)

(73) Assignee: GlaxoSmithKline Biologicals, s.a., Rixensart (BE)

( * ) Notice: Subject to any disclaimer, the term of this patent is extended or adjusted under 35 U.S.C. 154(b) by 0 days.

(21) Appl. No.: 11/573,128

(22) PCT Filed: Aug. 3, 2005

(86) PCT No.: PCT/EP2005/008434

§ 371 (c)(1),
(2), (4) Date: Feb. 2, 2007

(87) PCT Pub. No.: WO2006/013106

PCT Pub. Date: Feb. 9, 2006

(65) Prior Publication Data

US 2007/0243203 A1 Oct. 18, 2007

(30) Foreign Application Priority Data

Aug. 5, 2004 (GB) ................................. 0417494.2

(51) Int. Cl.
*C07K 14/00* (2006.01)
(52) U.S. Cl. ..................................................... 530/350
(58) Field of Classification Search ....................... None
See application file for complete search history.

(56) References Cited

U.S. PATENT DOCUMENTS

| 5,221,610 | A | 6/1993 | Montagnier et al. |
|---|---|---|---|
| 5,962,635 | A | 10/1999 | Azad et al. |
| 2003/0108562 | A1 | 6/2003 | Hanke et al. |
| 2003/0190308 | A1 | 10/2003 | Braun et al. |
| 2004/0073008 | A1* | 4/2004 | Iglesias Perez et al. ..... 530/350 |
| 2005/0175627 | A1 | 8/2005 | Schneider |

FOREIGN PATENT DOCUMENTS

| EP | 0577894 | 12/1994 |
|---|---|---|
| EP | 115596 | 6/2006 |
| WO | 01/43693 | 6/2001 |
| WO | 02/22080 | 3/2002 |
| WO | 02/068654 | 9/2002 |
| WO | 03/025003 | 3/2003 |
| WO | 2004/041851 | 5/2004 |
| WO | 2004/041852 | 5/2004 |
| WO | 2005/030964 | 4/2005 |

OTHER PUBLICATIONS

Woodberry et al., Immunogenicity of a Human Immunodeficiency Virus (HIV) Polytope Vaccine Containing Multiple HLA A2 HIV CD81 Cytotoxic T-Cell Epitopes, Journal of Virology, Jul. 1999, 73(7): 5320-5325.*
Vazquez-Blomquist et al., The HIV-1 chimeric protein CR3 expressed by poxviral vectors induces a diverse CD8+ T cell response in mice and is antigenic for PBMCs from HIV+ patients, Vaccine, 2003, 22:145-155.*
Moore et al., The adjuvant combination monophosphoryl lipid A and QS21 switches T cell responses induced with a soluble recombinant HIV protein from Th2 to Th1, Vaccine, 1999, 17:2517-2527.*
Kong, et al., "Immunogenicity of Multiple Gene and Clade Human Immunodeficiency Virus Type 1 DNA Vaccines," J. Virol. 77:12764-12772 (Dec. 2003).
Asjo et al., Phase I trial of a therapeutic HIV type 1 vaccine, Vacc-4x, in HIV type 1-infected individuals with or without antiretroviral therapy, AIDS Res Hum Retroviruses 18(18):1357-65 (Dec. 2002).
Azad et al., Large-scale production and characterization of recombinant HIV-1 Nef, J. General Virology, 75:651-655 (1994).
Berzofsky, Progress toward an artificial vaccine for HIV: identification of helper and cytotoxic T-cell epitopes and methods of immunization. Biotechnol. Ther. 2(1-2): 123-35 (1991).
Betts et al., Optimal antigens for HIV vaccines based on CD8+ T response, protein length, and sequence variability. DNA Cell Biology 21(9):665-70 (Sep. 2002).
Bodeus et al., In vitro binding and phosphorylation of HIV-1 Nef protein by serine/threonine protein kinase, J. General Virology, 76:1337-44 (1995).
Buck et al. The HIV-1 gag gene encodes an internal ribosome entry site, Journal of Virology 75(1):181-191 (2001).
Cosma et al., Therapeutic vaccination with MVA-HIV-1 nef elicits Nef-specific T-helper cell responses in chronically HIV-1 infected individuals. Vaccine 22(1)21-9 (Dec. 2003).
Dinchuk et al., Generation of transgenic mice carrying H IV TAT and NEF genes. (Abstract) *Int Conf AIDS 1990 Jun. 20-23; 6:192 (abstract No. Th.A.291).*
Estaquier et al., Comprehensive delineation of antigenic and immunogenic properties of peptides derived from the nef HIV-1 regulatory protein. Vaccine 11(11):1083-92 (1993).
Gahery-Segard et al., Long-term specific immune responses induced in humans by a human immunodeficiency virus type 1 lipopeptide vaccine: characterization of CD8+-T-cell epitopes recognized. J. Virol. 77(20):11220-31 (Oct. 2003).

(Continued)

Primary Examiner—Gary B Nickol
Assistant Examiner—Nicole Kinsey White
(74) Attorney, Agent, or Firm—Gwynedd Warren; Virginia G. Campen; SmithKline Beecham Corporation-Corporate Intellectual Property-US

(57) ABSTRACT

This invention relates to novel HIV polypeptide and polynucleotide fusions of Gag, Pol and Nef which are useful in immunogenic compositions and vaccines. The invention relates in particular to a polypeptide which comprises Nef or an immunogenic fragment thereof, and p17 Gag and/or p24 Gag or immunogenic fragments thereof, wherein when both p17 and p24 Gag are present there is at least one HIV antigen or immunogenic fragment between them. The polypeptide may also comprise Pol or RT or an immunogenic fragment thereof.

26 Claims, 21 Drawing Sheets

OTHER PUBLICATIONS

Gahery-Segard et al., Multiepitopic B- and T-cell responses induced in humans by a human immunodeficiency virus type 1 lipopeptide vaccine. J. Virol. 74(4):1694-703 (Feb. 2000).

Hinkula et al., Recognition of prominent viral epitopes induced by immunization with HIV-1 regulatory genes, J. Virology, 71:7 5528-39 (1997).

Iglesias et al. Chimeric proteins containing HIV1 T cell epitopes: expression in E. coli, purification and induction of antibodies in mice, J. Biochem Mol Bio & Biophys, 5:109-122 (2000).

Johnson and Walker. Cytotoxic T lymphocytes in human immunodeficiency virus infection: responses to structural proteins. Curr Top Microbiol Immunol;189:35-63 (1994).

Kmieciak et al., Enhancement of cellular and humoral immune responses to human immunodeficiency virus type 1 Gag and Pol by a G/P-92 fusion protein expressing highly immunogenic Gag p17/p24 and Pol p51 antigens. J. Human Virology 4(6):306-16 (2001).

Letvin et a., Progress in the development of Nan HIV-1 vaccine, Science, 280:1875 (1998).

Menendez-Arias et al., Cytotoxic T-lymphocyte responses to HIV-1 reverse transcriptase (review). Viral Immunol 11(4) :167-81 (1998).

Miller and Sarver, HIV accessory proteins as therapeutic targets. Nat Med 3(4):389-94 (1997).

Moore et al. The adjuvant combination monophosphoryl lipid A and QS21 switches T cell responses induced with a soluble recombinant HIV protein from Th2 to Th1, Vaccine, 1999, 17:2517-2527 (1999).

Murphy et al., The HIV-1 regulatory protein Nef has a specific function in viral expression in a murine macrophage cell line. J. Leukocyte Biology 56:294-303 (Sep. 1994).

Partidos et al., The effect of orientation of peptides on the immunogenicity of chimeric synthetic peptides representing measles virus protein sequences, Molecular Immunology, 29(5):651-658 (1992).

Pialoux et al., Lipopeptides induce cell-mediated anti-HIV immune responses in seronegative volunteers. AIDS 15(10):1239-49 (Jul. 2001).

Robert-Guroff, HIV Regulatory and accessory proteins: new targets for vaccine development. DNA and Cell Biology. 21(9): 597-598. (Sep. 2002).

Ruprecht et al., 1999: a time to re-evaluate AIDS vaccine strategies. Journal of Hum. Virol. 3(2):88-93 (2000).

Shiver et al., Recent advances in the development of HIV-1 vaccines using replication-incompetent adenovirus vectors. Annual Rev Med. 55:355-72 (2004).

* cited by examiner

Figure 1A
10% SDS-PAGE-Reducing (F4 p24-RT-Nef-p17)
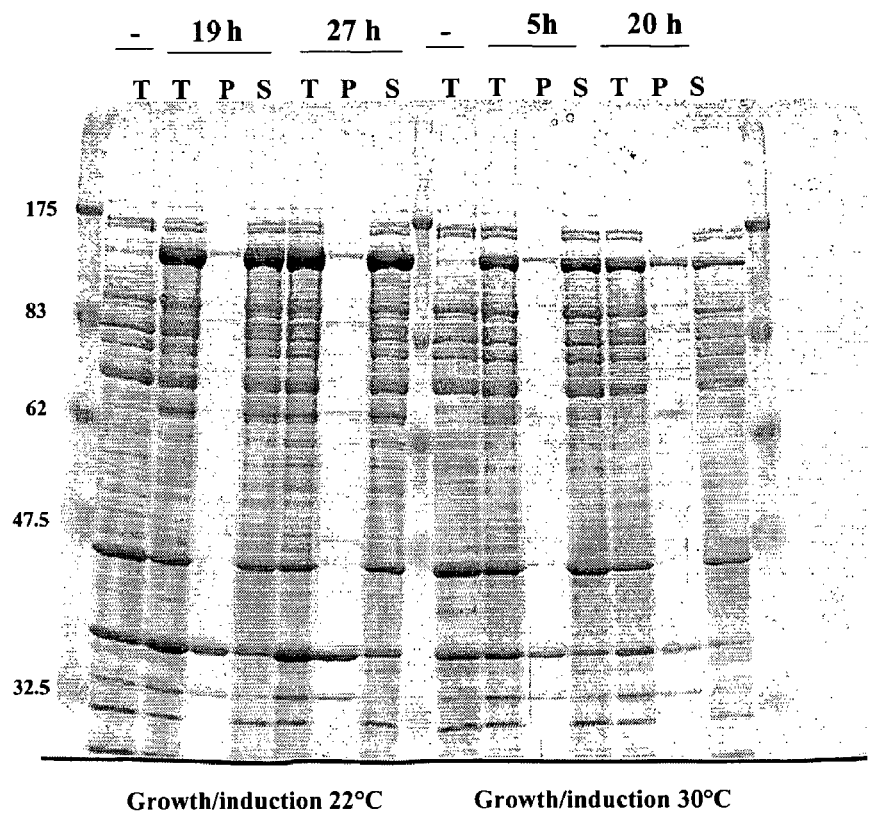
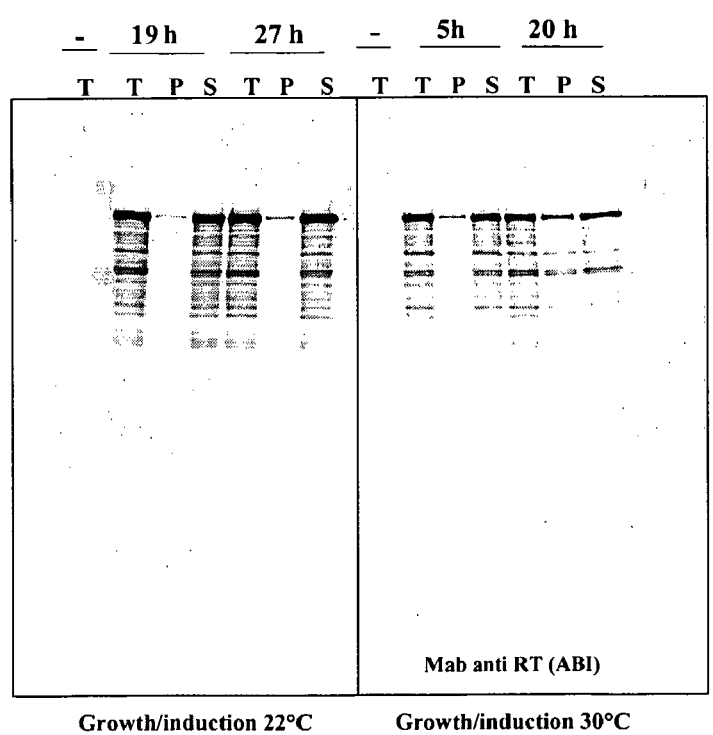

Figure 1B
Solubility Assay (F4 p24-RT-Nef-p17)
Reducing gels (10% SDS-PAGE)
Coomassie
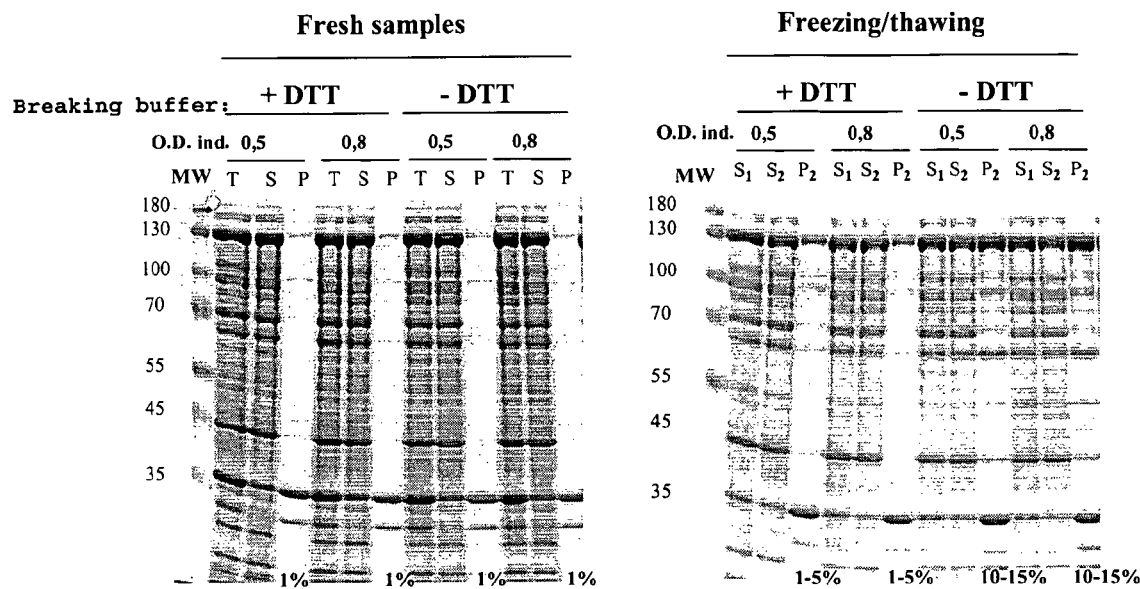
Western blot:
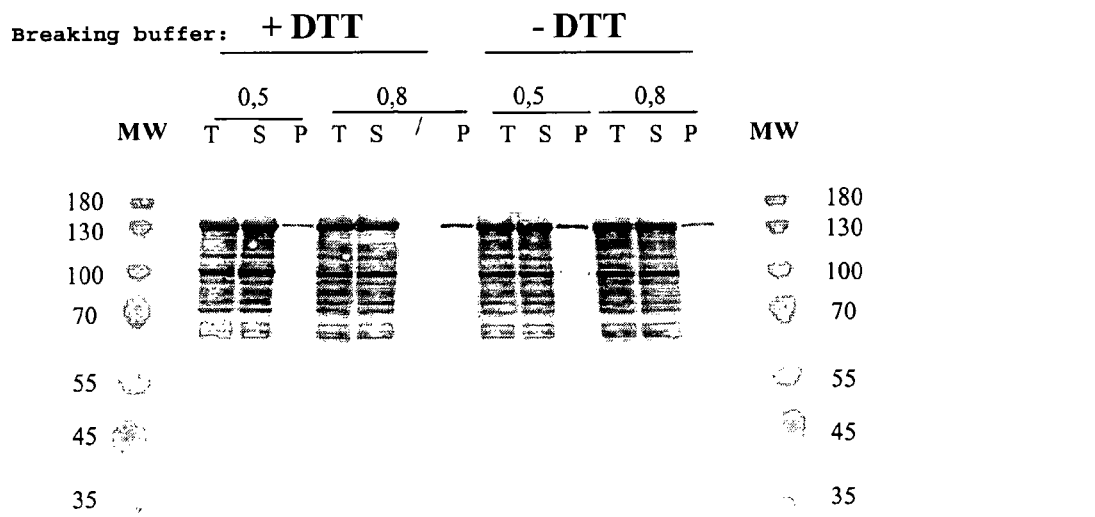

Figure 2: Coomassie stained gel and Western Blot for F4 codon-optimized
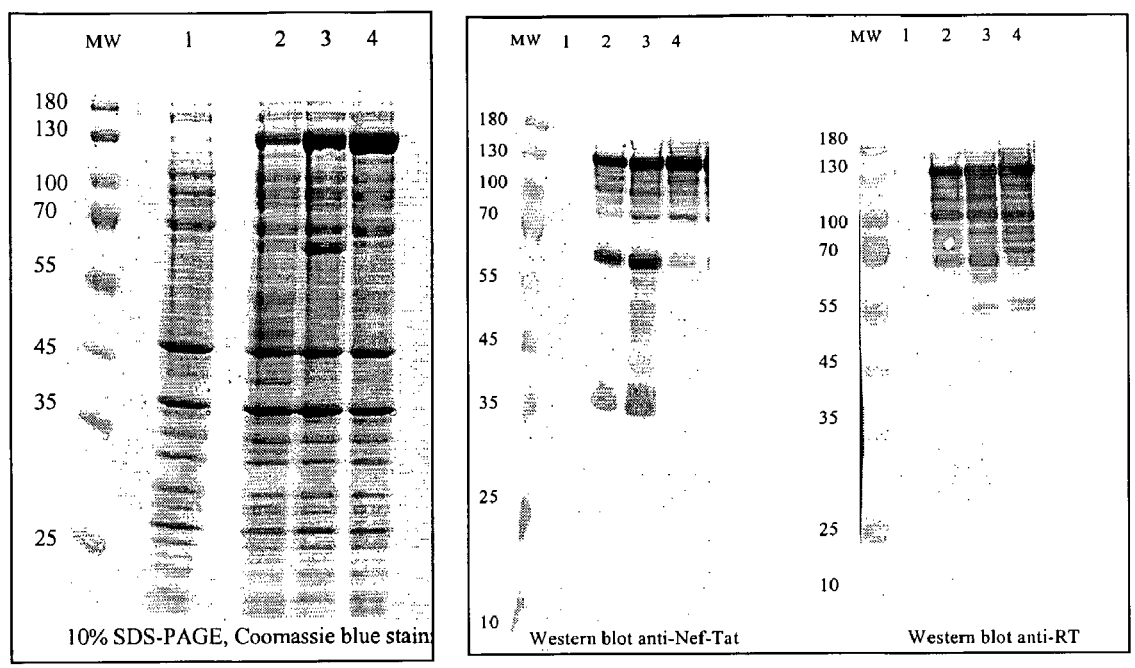
1/ non induced
2/ B834(DE3) / F4 (native gene)
3/ BLR(DE3) / F4 (native gene)
4/ BLR(DE3) / F4 (codon-optimized gene)

Figure 3
Alignment of RT proteins : GSK construct, HXB2, BH10

```
                          *          20          *          40          *
RT-GSK      : MGPISPIETVSVKLKPGMDGPKVKQWPLTEEKIKALVEICTEMEKEGKISKIGPE :  55
RT-HXB2     : --PISPIETVPVKLKPGMDGPKVKQWPLTEEKIKALVEICTEMEKEGKISKIGPE :  53
RT-BH10     : --PISPIETVPVKLKPGMDGPKVKQWPLTEEKIKALVEICTEMEKEGKISKIGPE :  53

60          *          80          *         100          *
RT-GSK      : NPYNTPVFAIKKKDSTKWRKLVDFRELNKRTQDFWEVQLGIPHPAGLKKKKSVTV : 110
RT-HXB2     : NPYNTPVFAIKKKDSTKWRKLVDFRELNKRTQDFWEVQLGIPHPAGLKKKKSVTV : 108
RT-BH10     : NPYNTPVFAIKKKDSTKWRKLVDFRELNKRTQDFWEVQLGIPHPAGLKKKKSVTV : 108

120          *         140          *         160
RT-GSK      : LDVGDAYFSVPLDEDFRKYTAFTIPSINNETPGIRYQYNVLPQGWKGSPAIFQSS : 165
RT-HXB2     : LDVGDAYFSVPLDEDFRKYTAFTIPSINNETPGIRYQYNVLPQGWKGSPAIFQSS : 163
RT-BH10     : LDVGDAYFSVPLDEDFRKYTAFTIPSINNETPGIRYQYNVLPQGWKGSPAIFQSS : 163

*         180          *         200          *         220
RT-GSK      : MTKILEPFRKQNPDIVIYQYMDDLYVGSDLEIGQHRTKIEELRQHLLRWGLTTPD : 220
RT-HXB2     : MTKILEPFRKQNPDIVIYQYMDDLYVGSDLEIGQHRTKIEELRQHLLRWGLTTPD : 218
RT-BH10     : MTKILEPFKKQNPDIVIYQYMDDLYVGSDLEIGQHRTKIEELRQHLLRWGLTTPD : 218

*         240          *         260          *
RT-GSK      : KKHQKEPPFLKMGYELHPDKWTVQPIVLPEKDSWTVNDIQKLVGKLNWASQIYPG : 275
RT-HXB2     : KKHQKEPPFLWMGYELHPDKWTVQPIVLPEKDSWTVNDIQKLVGKLNWASQIYPG : 273
RT-BH10     : KKHQKEPPFLWMGYELHPDKWTVQPIVLPEKDSWTVNDIQKLVGKLNWASQIYPG : 273

280          *         300          *         320          *
RT-GSK      : IKVRQLCKLLRGTKALTEVIPLTEEAELELAENREILKEPVHGVYYDPSKDLIAE : 330
RT-HXB2     : IKVRQLCKLLRGTKALTEVIPLTEEAELELAENREILKEPVHGVYYDPSKDLIAE : 328
RT-BH10     : IKVRQLCKLLRGTKALTEVIPLTEEAELELAENREILKEPVHGVYYDPSKDLIAE : 328

340          *         360          *         380
RT-GSK      : IQKQGQGQWTYQIYQEPPFKNLKTGKYARMRGAHTNDVKQLTEAVQKITTESIVIW : 385
RT-HXB2     : IQKQGQGQWTYQIYQEPPFKNLKTGKYARMRGAHTNDVKQLTEAVQKITTESIVIW : 383
RT-BH10     : IQKQGQGQWTYQIYQEPPFKNLKTGKYARMRGAHTNDVKQLTEAVQKITTESIVIW : 383

*         400          *         420          *         440
RT-GSK      : GKTPKFKLPIQKETWETWWTEYWQATWIPEWEFVNTPPLVKLWYQLEKEPIVGAE : 440
RT-HXB2     : GKTPKFKLPIQKETWETWWTEYWQATWIPEWEFVNTPPLVKLWYQLEKEPIVGAE : 438
RT-BH10     : GKTPKFKLPIQKETWETWWTEYWQATWIPEWEFVNTPPLVKLWYQLEKEPIVGAE : 438

*         460          *         480          *
RT-GSK      : TFYVDGAANRETKLGKAGYVTNRGRQKVVTLTDTTNQKTELQAIYLALQDSGLEV : 495
RT-HXB2     : TFYVDGAANRETKLGKAGYVTNRGRQKVVTLTDTTNQKTELQAIYLALQDSGLEV : 493
RT-BH10     : TFYVDGAANRETKLGKAGYVTNKGRQKVVPLTNTTNQKTELQAIYLALQDSGLEV : 493

500          *         520          *         540          *
RT-GSK      : NIVTDSQYALGIIQAQPDQSESELVNQIIEQLIKKEKVYLAWVPAHKGIGGNEQV : 550
RT-HXB2     : NIVTDSQYALGIIQAQPDQSESELVNQIIEQLIKKEKVYLAWVPAHKGIGGNEQV : 548
RT-BH10     : NIVTDSQYALGIIQAQPDKSESELVNQIIEQLIKKEKVYLAWVPAHKGIGGNEQV : 548

560
RT-GSK      : DKLVSAGIRKVL : 562
RT-HXB2     : DKLVSAGI---- : 556
RT-BH10     : DKLVSAGI---- : 556
```

K: point mutation introduced to remove enzyme activity
Bold and underlined: amino acids differing from RT/HXB2
Highlighted block: Rnase H domain
Bold: first amino acids of integrase
Bracket: end of p51

Coomassie stained gel and Western Blot for P51 RT (codon optimized)

NP=Nef-p17          PN= p17-Nef
NLP=Nef- GSGGGP - p17   PLN= p17- GSGGGP - Nef

10 % SPS-PAGE reducing gel, coomassie blue staining

WB α Nef-Tat (LAS 97340 - Rabbit 388), 1/5000

Figure 11
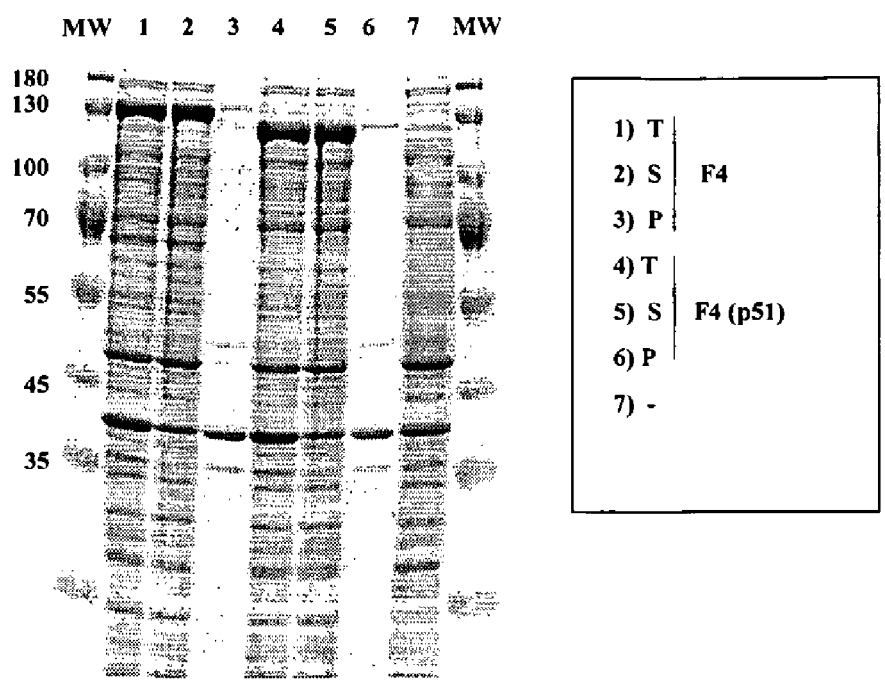
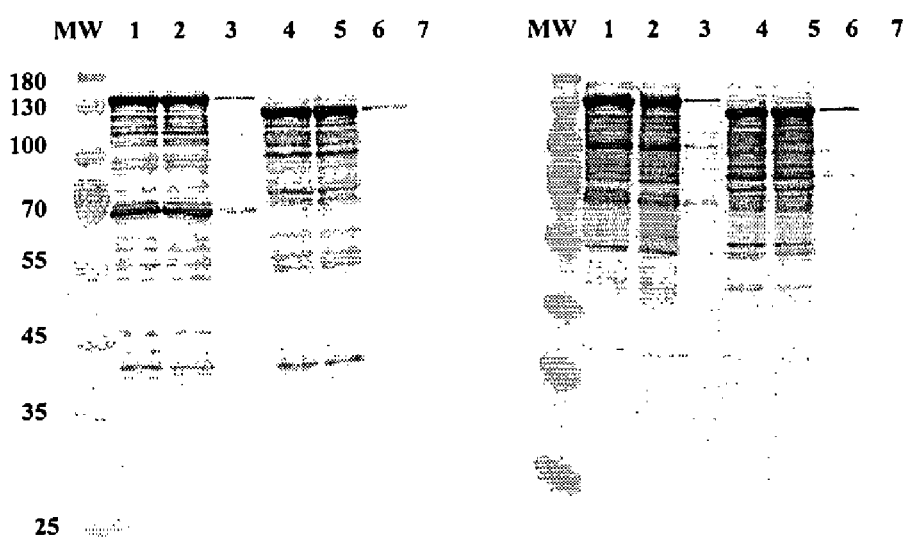
Western Blot anti NefTat (rabbit 388)    Western Blot anti RT (rabbit P03L16)t Figure 13: Purification of F4.
A: Coomassie blue-stained 4-20% SDS-gel, 5 µg protein/lane; B: anti-p24/anti Nef-Tat western blot, 0.5 µg protein/lane. lane 1, MW standard; lane 2, homogenate; lane 3, clarified homogenate; lane 4, resuspended AS precipitate; lane 5, SO3 eluate; lane 6, Octyl sepharose eluate; lane 7, Q sepharose eluate; lane 8, Superdex 200 eluate.

Figure 14

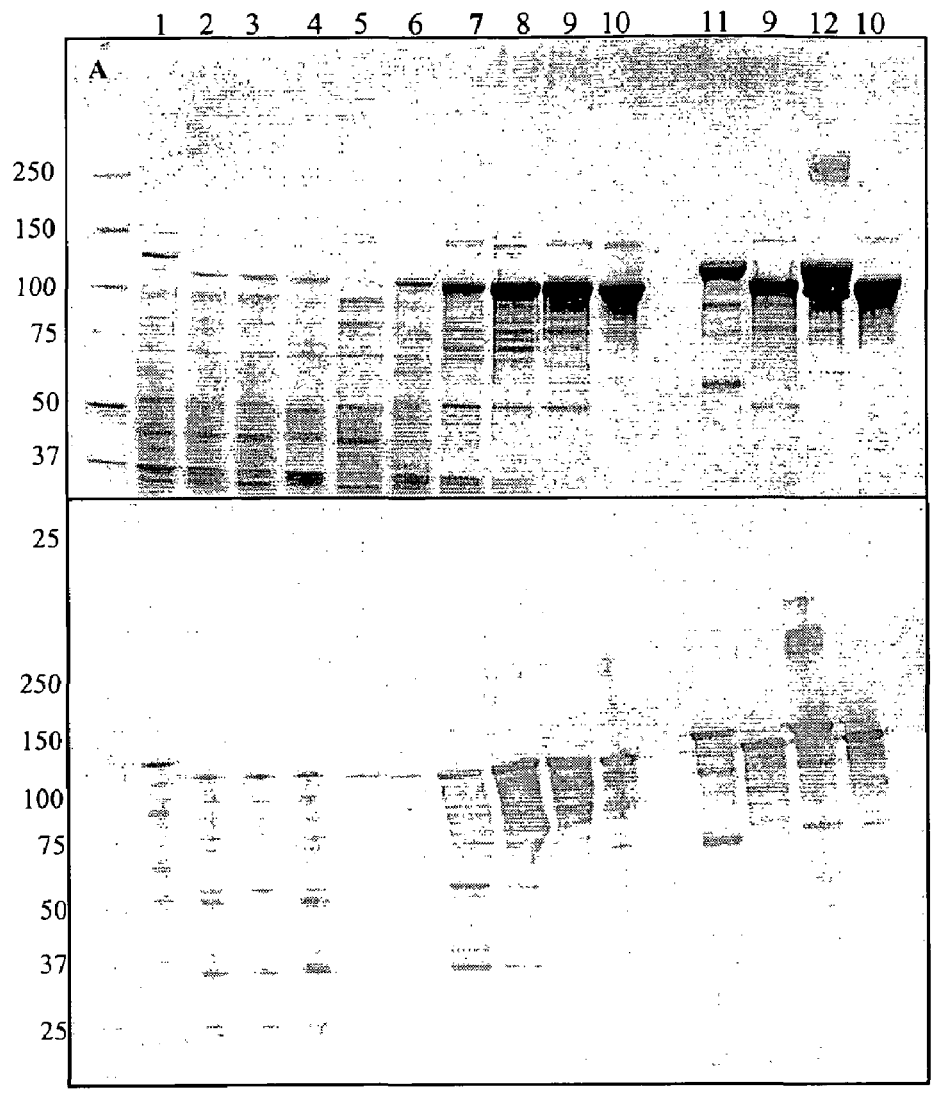

Figure 14: Purification of F4(p51)*
A: Coomassie blue-stained 4-20% SDS-gel, 5 µg protein/lane; B: anti-p24/anti Nef-Tat western blot, 0.5 µg protein/lane. lane 1, homogenate F4; lane 2, homogenate F4(p51)*; lane 3, clarified homogenate; lane 4, homogenate pellet; lane 5, AS precipitation supernatant,; lane 6, resuspended AS precipitate; lane 7, SO3 eluate; lane 8, Octyl sepharose eluate; lane 9, Q sepharose eluate; lane 10, Superdex 200 eluate; lane 11, Q eluate F4; lane 12, Superdex 200 eluate F4.

Figure 15: Purification of F4*.
A: Coomassie blue-stained 4-20% SDS-gel, 5 μg protein/lane; B: anti-p24/anti Nef-Tat western blot, 0.5 μg protein/lane. Lane 1, homogenate; 2, clarified homogenate; 3, resuspended AS precipitate; 4, SO3 eluate; 5, Octyl sepharose eluate; 6, Q eluate; 7, concentrated/dialyzed Q sepharose eluate; 8, Superdex 200 eluate; 9, rejected fraction from Superdex 200 eluate.

Figure 16: Purity of F4 vs F4* vs F4(51)*.
A: Q eluate, B: S200 eluate. The 4-12% SDS-gels were loaded with 5 µg protein for the Coomassie blue stain (on the left) and with 0.5 µg for the anti-p24/anti-Nef-Tat western blot (on the right).

Figure 17: SDS-PAGE follow up of the purification of F4co and carboxyamidated F4co. 5 μg of each fraction collected during the purification of F4co or F4coca were separated on a 4-12% SDS gel. The gel was Coomassie blue stained. 1: Homogenate; 2: CM hyperZ eluate; 3: Q sepharose eluate; 4: Purified bulk.

Figure 18: SDS-PAGE analysis of F4, F4co and F4coca purified according to purification method I or method II. 5 μg of each protein were separated on a 4-12% SDS gel in reducing conditions (left) or non-reducing conditions (right). The gel was Coomassie blue stained. 1: Method II – F4co; 2: Method II – F4coca; 3: Method I – F4coca; 4: Method I – F4; 5: Method I – F4 carboxyamidated.

US 7,612,173 B2

VACCINE FOR PREVENTION AND TREATMENT OF HIV-INFECTION

CROSS-REFERENCE TO RELATED APPLICATIONS

This application is a § 371 application of PCT/EP2005/008434, filed 3 Aug. 2005. This application also claims benefit of the earlier filing date of Great Britain Patent Application No. 0417494.2, filed 5 Aug. 2004.

FIELD OF THE INVENTION

The present invention relates to novel HIV polypeptide constructs, to their use in medicine, to pharmaceutical compositions comprising them and to methods for their manufacture. The invention also relates to polynucleotides encoding the polypeptides. In particular, the invention relates to fusion proteins comprising HIV-1 Nef and HIV-1 Gag or fragments thereof, and to polynucleotides encoding them. More particularly, the invention relates to fusion proteins comprising HIV-1 Nef, HIV-1 Pol and HIV-1 Gag proteins or fragments thereof and to polynucleotides encoding them.

HIV-1 is the primary cause of the acquired immune deficiency syndrome (AIDS) which is regarded as one of the world's major health problems. There is a need for a vaccine for the prevention and/or treatment of HIV infection.

BACKGROUND TO THE INVENTION

HIV-1 is an RNA virus of the family Retroviridiae. The HIV genome encodes at least nine proteins which are divided into three classes: the major structural proteins Gag, Pol and Env, the regulatory proteins Tat and Rev, and the accessory proteins Vpu, Vpr, Vif and Nef. The HIV genome exhibits the 5'LTR-gag-pol-env-LTR3' organization of all retroviruses.

The HIV envelope glycoprotein gp120 is the viral protein that is used for attachment to the host cell. This attachment is mediated by binding to two surface molecules of helper T cells and macrophages, known as CD4 and one of the two chemokine receptors CCR-5 or CXCR-4. The gp120 protein is first expressed as a larger precursor molecule (gp160), which is then cleaved post-translationally to yield gp120 and gp41. The gp120 protein is retained on the surface of the virion by linkage to the gp41 molecule, which is inserted into the viral membrane.

The gp120 protein is the principal target of neutralizing antibodies, but unfortunately the most immunogenic regions of the proteins (V3 loop) are also the most variable parts of the protein. Therefore, the use of gp120 (or its precursor gp160) as a vaccine antigen to elicit neutralizing antibodies is thought to be of limited use for a broadly protective vaccine. The gp120 protein does also contain epitopes that are recognized by cytotoxic T lymphocytes (CTL). These effector cells are able to eliminate virus-infected cells, and therefore constitute a second major antiviral immune mechanism. In contrast to the target regions of neutralizing antibodies some CTL epitopes appear to be relatively conserved among different HIV strains. For this reason gp120 and gp160 maybe useful antigenic components in vaccines that aim at eliciting cell-mediated immune responses (particularly CTL).

Non-envelope proteins of HIV-1 include for example internal structural proteins such as the products of the gag and pol genes and other non-structural proteins such as Rev, Nef, Vif and Tat (Green et al., New England J. Med, 324, 5, 308 et seq (1991) and Bryant et al. (Ed. Pizzo), Pediatr. Infect. Dis. J., 11, 5, 390 et seq (1992).

HIV Nef is an early protein, that is it is expressed early in infection and in the absence of structural protein.

The Nef gene encodes an early accessory HIV protein which has been shown to possess several activities. For example, the Nef protein is known to cause the down regulation of CD4, the HIV receptor, and MHC class I molecules from the cell surface, although the biological importance of these functions is debated. Additionally Nef interacts with the signal pathway of T cells and induces an active state, which in turn may promote more efficient gene expression. Some HIV isolates have mutations in this region, which cause them not to encode functional protein and are severely compromised in their replication and pathogenesis in vivo.

The Gag gene is translated as a precursor polyprotein that is cleaved by protease to yield products that include the matrix protein (p17), the capsid (p24), the nucleocapsid (p9), p6 and two space peptides, p2 and p1.

The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6.

In addition to the 3 major Gag proteins, all Gag precursors contain several other regions, which are cleaved out and remain in the virion as peptides of various sizes. These proteins have different roles e.g. the p2 protein has a proposed role in regulating activity of the protease and contributes to the correct timing of proteolytic processing.

The p17 (MA) polypeptide is derived from the N-terminal, myristoylated end of p55. Most MA molecules remain attached to the inner surface of the virion lipid bilayer, stabilizing the particle. A subset of MA is recruited inside the deeper layers of the virion where it becomes part of the complex which escorts the viral DNA to the nucleus. These MA molecules facilitate the nuclear transport of the viral genome because a karyophilic signal on MA is recognized by the cellular nuclear import machinery. This phenomenon allows HIV to infect non-dividing cells, an unusual property for a retrovirus.

The p24 (CA) protein forms the conical core of viral particles. Cyclophilin A has been demonstrated to interact with the p24 region of p55 leading to its incorporation into HIV particles. The interaction between Gag and cyclophilin A is essential because the disruption of this interaction by cyclosporin A inhibits viral replication.

The NC region of Gag is responsible for specifically recognizing the so-called packaging signal of HIV. The packaging signal consists of four stem loop structures located near the 5' end of the viral RNA, and is sufficient to mediate the incorporation of a heterologous RNA into HIV-1 virions. NC binds to the packaging signal through interactions mediated by two zinc-finger motifs. NC also facilitates reverse transcription.

The p6 polypeptide region mediates interactions between p55 Gag and the accessory protein Vpr, leading to the incorporation of Vpr into assembling virions. The p6 region also contains a so-called late domain which is required for the efficient release of budding virions from an infected cell.

The Pol gene encodes two proteins containing the two activities needed by the virus in early infection, the RT and the integrase protein needed for integration of viral DNA into cell DNA. The primary product of Pol is cleaved by the virion protease to yield the amino terminal RT peptide which contains activities necessary for DNA synthesis (RNA and DNA-dependent DNA polymerase activity as well as an RNase H function) and carboxy terminal integrase protein. HIV RT is a heterodimer of full-length RT (p66) and a cleavage product (p51) lacking the carboxy terminal RNase H domain.

RT is one of the most highly conserved proteins encoded by the retroviral genome. Two major activities of RT are the DNA Pol and Ribonuclease H. The DNA Pol activity of RT uses RNA and DNA as templates interchangeably and like all DNA polymerases known is unable to initiate DNA synthesis de novo, but requires a pre existing molecule to serve as a primer (RNA).

The RNase H activity inherent in all RT proteins plays the essential role early in replication of removing the RNA genome as DNA synthesis proceeds. It selectively degrades the RNA from all RNA-DNA hybrid molecules. Structurally the polymerase and ribo H occupy separate, non-overlapping domains with the Pol covering the amino two thirds of the Pol.

The p66 catalytic subunit is folded into 5 distinct subdomains. The amino terminal 23 of these have the portion with RT activity. Carboxy terminal to these is the RNase H Domain.

WO 03/025003 describes DNA constructs encoding HIV-1 p17/24 Gag, Nef and RT, wherein the DNA sequences may be codon optimized to resemble highly expressed human genes. These constructs are useful in DNA vaccines.

Fusion proteins containing multiple HIV antigens have been suggested as vaccine candidates for HIV, for example the Nef-Tat fusion as described in WO 99/16884. However, fusion proteins are not straightforward to produce; there can be difficulties in expressing them because they do not correspond to native proteins. There can be difficulties at the transcription level, or further downstream. Also, they may not be straightforward to formulate into a pharmaceutically acceptable composition. Notably, the majority of approaches to HIV vaccines that involve multiple antigens fused together, are DNA or live vector approaches rather than polypeptide fusion proteins.

SUMMARY OF THE INVENTION

The present invention provides novel constructs for use in vaccines for the prophylaxis and treatment of HIV infections and AIDS.

BRIEF DESCRIPTION OF THE DRAWINGS

FIGS. 1A and B are images of Coomassie stained gels (upper panels) and western blots (lower panels) of F4 p24-RT-Nef-P17.

FIG. 2 is images of a Coomassie stained gels (upper panel) and western blot (lower panel) of codon-optimized F4.

FIG. 3 is an alignment of FT proteins.

FIG. 11 is images of a Coomassie stained gel (upper panel) and western blots (lower panels) showing expression of F4(p51).

FIGS. 14 A and B are images of a Coomassie stained gel (A) and western blot (B) showing purification of F4(p51)*.

DETAILED DESCRIPTION

Figure 4:
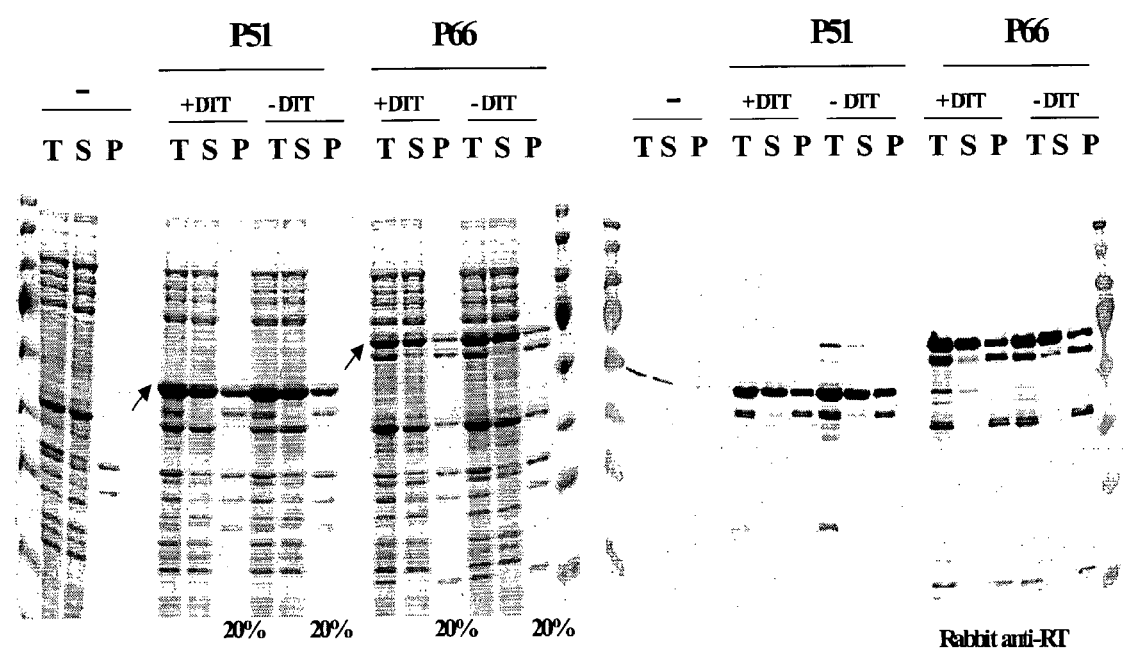
FIG. 4 is images of a Coomassie stained gel (left panel) and western blot (right panel) of P51 RT (codon optimized).

In one aspect the invention provides a polypeptide which comprises Nef or an immunogenic fragment or derivative thereof, and p17 Gag and/or p24 Gag or immunogenic fragments or derivatives thereof, wherein when both p17 and p24 Gag are present there is at least one HIV antigen or immunogenic fragment between them.

In the constructs and compositions according to the invention as described herein, the Nef is preferably a full length Nef.

In the constructs according to the invention the p17 Gag and p24 Gag are preferably full length p17 and p24 respectively.

In one embodiment the polypeptide comprises both p17 and p24 Gag or immunogenic fragments thereof. In such a construct the p24 Gag component and p17 Gag component are separated by at least one further HIV antigen or immunogenic fragment, such as Nef and/or RT or immunogenic fragments or derivatives thereof.

Alternatively p17 or p24 Gag may be provided separately. Thus the invention also provides a composition comprising (i) a polypeptide which comprises Nef or an immunogenic fragment or derivative thereof and p17 Gag or an immunogenic fragment or derivative thereof, and (ii) p24 Gag or an immunogenic fragment or derivative thereof, or (i) a polypeptide which comprises Nef or an immunogenic fragment or derivative thereof and p24 Gag or an immunogenic fragment or derivative thereof, and (ii) p17 Gag or an immunogenic fragment or derivative thereof.

In another embodiment the polypeptide construct according to the invention further comprises Pol or a derivative of Pol such as RT or an immunogenic fragment or derivative thereof. Particular fragments of RT that are suitable for use in the invention are fragments in which the RT is truncated at the C terminus, preferably such that they lack the carboxy terminal RNase H domain. One such fragment lacking the carboxy terminal Rnase H domain is the p51 fragment described herein.

Preferably the RT or immunogenic fragment in the fusion proteins described herein is p66 RT or p51 RT.

The RT component of the fusion protein or composition according to the invention optionally comprises a mutation at position 592, or equivalent mutation in strains other than HXB2, such that the methionine is removed by mutation to another residue e.g. lysine. The purpose of this mutation is to remove a site which serves as an internal initiation site in prokaryotic expression systems.

The RT component also, or alternatively, comprises a mutation to remove the enzyme activity (reverse transcriptase). Thus K231 may be present instead of W.

In fusion proteins according to the invention which comprise p24 and RT, it may be preferable that the p24 precedes the RT in the construct because when the antigens are expressed alone in E. coli better expression of p24 than of RT is observed.

Preferred constructs according to the invention include the following:

1. p24-RT-Nef-p17
2. p24-RT*-Nef-p17
3. p24-p51RT-Nef-p17
4. p24-p51RT*-Nef-p17
5. p17-p51RT-Nef
6. p17-p51RT*-Nef
7. Nef-p17
8. Nef-p17 with linker
9. p17-Nef
10. p17-Nef with linker

* represents RT methionine$_{592}$ mutation to lysine

The linker included in the constructs listed above may be any short amino acid sequence for decreasing potential interactions between the two fusion partners that it links together. The linker may be for example from 4-10 amino acids in length. For example, it may be a 6 amino acid sequence such as the GSGGGP sequence (SEQ ID NO:20) described herein in the examples.

In another aspect the present invention provides a fusion protein of HIV antigens comprising at least four HIV antigens or immunogenic fragments, wherein the four antigens or fragments are or are derived from Nef, Pol and Gag. Preferably Gag is present as two separate components which are separated by at least one other antigen in the fusion. Preferably the Nef is full length Nef. Preferably the Pol is p66 or p51RT. Preferably the Gag is p17 and p24 Gag. Other preferred features and properties of the antigen components of the fusion in this aspect of the invention are as described herein.

Preferred embodiments of this aspect of the invention are the four component fusions as already listed above:

1. p24-RT-Nef-p17
2. p24-RT*-Nef-p17
3. p24-p51RT-Nef-p17
4. p24-p51RT*-Nef-p17

The term "derived from" or "derivative" in relation to the HIV antigens included in the invention means that the antigens may have been altered in a limited way compared to their native counterparts. This includes point mutations which may change the properties of the protein for example by improving expression in prokaryotic systems or removing undesirable activity including undesirable enzyme activity. The point mutations described herein for RT are designed to achieve these things. However, the antigens must remain sufficiently similar to the native antigens such that they retain the antigenic properties desirable in a vaccine and thus they remain capable of raising an immune response against the native antigen. Whether or not a particular derivative raises such an immune response may be measured by a suitable immunological assay such as an ELISA (for antibody responses) or flow cytometry using suitable staining for cellular markers and cytokines (for cellular responses).

The polypeptide constructs of HIV antigens according to the invention are capable of being expressed in in vitro systems including prokaryotic systems such as E. coli. Advantageously they can be purified by conventional purification methods.

The fusions described herein are preferably soluble when expressed in a selected expression system, that is they are present in a substantial amount in the supernatant of a crude extract from the expression system. The presence of the fusion protein in the crude extract can be measured by conventional means such as running on an SDS gel, coomassie staining and checking the appropriate band by densitometric measurement. Fusion proteins according to the invention are preferably at least 50% soluble, more preferably at least 70% soluble, most preferably 90% soluble or greater as measured by the techniques described herein in the Examples. Techniques to improve solubility of recombinantly expressed proteins are known, for example in prokaryotic expression systems solubility is improved by lowering the temperature at which gene expression is induced.

The fusion proteins described herein can be purified. In particular they can be purified while remaining soluble or significantly soluble.

Immunogenic fragments as described herein will contain at least one epitope of the antigen and display HIV antigenicity and are capable of raising an immune response when presented in a suitable construct, such as for example when fused to other HIV antigens or presented on a carrier, the immune response being directed against the native antigen. Typically the immunogenic fragments contain at least 20, preferably 50, more preferably 100 contiguous amino acids from the HIV antigen.

The invention provides in a further aspect polynucleotides encoding the polypeptides according to the invention.

Polynucleotides according to the invention may be used as polynucleotide vaccines. The polynucleotides may be present within any of a variety of delivery systems known to those of ordinary skill in the art, including nucleic acid expression systems such as plasmid DNA, bacterial and viral expression systems. Numerous gene delivery techniques are well known in the art, such as those described by Rolland, Crit. Rev. Therap. Drug Carrier Systems 15:143-198, 1998 and references cited therein. Appropriate nucleic acid expression systems contain the necessary DNA sequences for expression in the patient (such as a suitable promoter and terminating signal). When the expression system is a recombinant live microorganism, such as a virus or bacterium, the gene of interest can be inserted into the genome of the live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox, modified poxviruses e.g. Modified Virus Ankara (MVA)), alphaviruses (Sindbis virus, Semliki Forest Virus, Venezuelian Equine Encephalitis Virus), flaviviruses (yellow fever virus, Dengue virus, Japanese encephalitis virus), adenoviruses, adeno-associated virus, picornaviruses (poliovirus, rhinovirus), herpesviruses (varicella zoster virus, etc), morbilliviruses (e.g. measles), *Listeria, Salmonella, Shigella, Neisseria*, BCG. These viruses and bacteria can be virulent, or attenuated in various ways in order to obtain live vaccines. Such live vaccines also form part of the invention.

A preferred measles vector for use as a live vector according to the invention is the Schwartz strain or a strain derived therefrom.

A preferred adenovirus for use as a live vector is a low sero-prevalent human adenovirus such as Ad5 or Ad35 or a non-human originating adenovirus such as a non-human primate adenovirus such as a simian adenovirus. Such low sero-prevalent human or similar adenoviruses will have less than 60, typically less than 50% sero-prevelance in the population. Preferably the vectors are replication defective. Typically these viruses contain an E1 deletion and can be grown on cell lines that are transformed with an E1 gene. Preferred simian adenoviruses are viruses isolated from chimpanzee. In particular C68 (also known as Pan 9) (See U.S. Pat. No. 6,083,716) and Pan 5, 6 and Pan 7 (WO 03/046124) are preferred for use in the present invention. These vectors can be manipulated to insert a heterologous polynucleotide according to the invention such that the polypeptides according to the invention maybe expressed. The use, formulation and manufacture of such recombinant adenoviral vectors is described in detail in WO 03/046142.

Thus, the Nef, p17 and p24 Gag and RT of a preferred vaccine according to the invention may be provided in the form of a polynucleotide encoding the desired polypeptide.

Polynucleotides according to the invention may be used to express the encoded polypeptides in a selected expression system. At least one of the HIV antigens, for example the RT, may be encoded by a codon optimized sequence in the polynucleotide, that is to say the sequence has been optimized for expression in a selected recombinant expression system such as *E. coli*.

In another aspect the invention provides a p51 RT polypeptide or derivative thereof or a polynucleotide encoding it, preferably codon optimized for expression in a suitable expression system, particularly a prokaryotic system such as *E. coli*.

The p51 RT polypeptide or polynucleotide may be used alone, or in combination with a polypeptide or polynucleotide construct according to the invention. Thus in a further aspect the invention provides a composition comprising (i) a polypeptide which comprises Nef or a fragment containing a Nef epitope and p17 Gag and/or p24 Gag, wherein when both p17 and p24 Gag are present there is at least one HIV antigen or immunogenic fragment between them and (ii) a p51 RT polypeptide. The invention further provides polynucleotides encoding these.

According to this embodiment (i) may be selected from for example:
1. Nef-p17
2. Nef-p17 with linker
3. p17-Nef
4. p17-Nef with linker Preferably Nef is full length Nef. Preferably p17 is full length p17.

The polypeptides and polynucleotides according to the invention may be combined with other antigens or polynucleotides encoding other antigens. In particular, this may include HIV env proteins or fragments or derivatives thereof. Preferred forms of env are gp120, gp140 and gp160. The env may be for example the envelope protein described in WO 00/07631 from an HIV-1 clade B envelope clone known as R2, or a fragment or derivative thereof. Thus the invention further provides a composition comprising any of the polypeptides or polypeptide compositions according to the invention, together with an HIV env protein or fragment or derivative thereof. Similarly the invention provides a composition comprising a polynucleotide or polynucleotides encoding a polypeptides or polypeptides according to the invention and a polynucleotide encoding an HIV env protein or fragment or derivative thereof.

The invention further provides methods of preparing the polypeptides described herein which method comprises expressing a polynucleotide encoding the polypeptide in a suitable expression system, particularly a prokaryotic system such as *E. coli* and recovering the expressed polypeptide. Preferably expression is induced at a low temperature, that is a temperature below 37°, to promote the solubility of the polypeptide.

The invention further provides a process for purifying a polypeptide as described herein, which process comprises:
i). providing a composition comprising the unpurified polypeptide;
ii). Subjecting the composition to at least two chromatographic steps;
iii). Optionally carboxyamidating the polypeptide;
iv) Performing a buffer exchange step to provide the protein in a suitable buffer for a pharmaceutical formulation.

The carboxyamidation may be performed between the two chromatographic steps. The carboxyamidation step may be performed using iodoacetimide.

In one example, the process according to the invention uses no more than two chromatographic steps.

The invention further provides pharmaceutical compositions and immunogenic compositions and vaccines comprising the polypeptides and polynucleotides according to the invention, in combination with a pharmaceutically acceptable adjuvant or carrier.

Vaccines according to the invention may be used for prophylactic or therapeutic immunization against HIV.

The invention further provides the use of the polypeptides and polypeptide compositions and the polynucleotides and polynucleotide compositions as described herein, in the manufacture of a vaccine for prophylactic or therapeutic immunization against HIV.

The vaccine of the present invention will contain an immunoprotective or immunotherapeutic quantity of the polypeptide and/or polynucleotide antigens and may be prepared by conventional techniques.

Vaccine preparation is generally described in New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in the vaccine dose is selected as an amount which induces an immunoprotective response without significant, adverse side effects in typical vaccines. Such amount will vary depending upon which specific immunogen is employed and the vaccination regimen that is selected. Generally, it is expected that each dose will comprise 1-1000 µg of each protein, preferably 2-200 µg, most preferably 4-40 µg of the polypeptide fusion. An optimal amount for a particular vaccine can be ascertained by standard studies involving observation of antibody titres and other immune responses in subjects. Following an initial vaccination, subjects may receive a boost in about 4 weeks, and a subsequent second booster immunisation.

The proteins of the present invention are preferably adjuvanted in the vaccine formulation of the invention. Adjuvants are described in general in Vaccine Design—the Subunit and Adjuvant Approach, edited by Powell and Newman, Plenum Press, New York, 1995.

Suitable adjuvants include an aluminium salt such as aluminium hydroxide or aluminium phosphate, but may also be a salt of calcium, iron or zinc, or may be an insoluble suspension of acylated tyrosine, or acylated sugars, cationically or anionically derivatised polysaccharides, or polyphosphazenes.

In the formulation of the invention it is preferred that the adjuvant composition induces a preferential Th1 response. However it will be understood that other responses, including other humoral responses, are not excluded.

An immune response is generated to an antigen through the interaction of the antigen with the cells of the immune system. The resultant immune response may be broadly distinguished into two extreme categories, being humoral or cell mediated immune responses (traditionally characterised by antibody and cellular effector mechanisms of protection respectively). These categories of response have been termed Th1-type responses (cell-mediated response), and Th2-type immune responses (humoral response).

Extreme Th1-type immune responses may be characterised by the generation of antigen specific, haplotype restricted cytotoxic T lymphocytes, and natural killer cell responses. In mice Th1-type responses are often characterised by the generation of antibodies of the IgG2a subtype, whilst in the human these correspond to IgG1 type antibodies. Th2-type immune responses are characterised by the generation of a broad range of immunoglobulin isotypes including in mice IgG1, IgA, and IgM.

It can be considered that the driving force behind the development of these two types of immune responses are cytokines, a number of identified protein messengers which serve to help the cells of the immune system and steer the eventual immune response to either a Th1 or Th2 response. Thus high levels of Th1-type cytokines tend to favour the induction of cell mediated immune responses to the given antigen, whilst high levels of Th2-type cytokines tend to favour the induction of humoral immune responses to the antigen.

It is important to remember that the distinction of Th1 and Th2-type immune responses is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) *TH1 and TH2 cells: different patterns of lymphokine secretion lead to different functional properties.* *Annual Review of Immunology*, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumour necrosis factor-β (TNF-β).

It is known that certain vaccine adjuvants are particularly suited to the stimulation of either Th1 or Th2-type cytokine responses. Traditionally the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses.

Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype.

Preferred Th1-type immunostimulants which may be formulated to produce adjuvants suitable for use in the present invention include and are not restricted to the following.

Monophosphoryl lipid A, in particular 3-de-O-acylated monophosphoryl lipid A (3D-MPL), is a preferred Th1-type immunostimulant for use in the invention. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al., 1986, *Int. Arch. Allergy. Immunol.*, 79(4):392-6; Hilgers et al., 1987, Immunology, 60(1):141-6; and EP 0 549 074 B1). A preferred form of 3D-MPL is in the form of a particulate formulation having a small particle size less than 0.2 µm in diameter, and its method of manufacture is disclosed in EP 0 689 454.

Saponins are also preferred Th1 immunostimulants in accordance with the invention. Saponins are well known adjuvants and are taught in: Lacaille-Dubois, M and Wagner H. (1996. A review of the biological and pharmacological activities of saponins. Phytomedicine vol 2 pp 363-386). For example, Quil A (derived from the bark of the South American tree *Quillaja Saponaria Molina*), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP 0 362 279 B1. The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. One such system is known as an Iscorn and may contain one or more saponins.

Another preferred immunostimulant is an immunostimulatory oligonucleotide containing unmethylated CpG dinucleotides ("CpG"). CpG is an abbreviation for cytosineguanosine dinucleotide motifs present in DNA. CpG is known in the art as being an adjuvant when administered by both systemic and mucosal routes (WO 96/02555, EP 468520, Davis et al., *J. Immunol,* 1998, 160(2):870-876; McCluskie and Davis, *J. Immunol.,* 1998, 161(9):4463-6). Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequences containing oligonucleotides can activate various immune subsets, including natural killer cells (which produce interferon γ and have cytolytic activity) and macrophages (Wooldrige et al Vol 89 (no. 8), 1977). Other unmethylated CpG containing sequences not having this consensus sequence have also now been shown to be immunomodulatory.

CpG when formulated into vaccines, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., *Proc. Natl. Acad. Sci., USA,* 1998, 95(26), 15553-8).

Such immunostimulants as described above may be formulated together with carriers, such as for example liposomes, oil in water emulsions, and or metallic salts, including aluminium salts (such as aluminium hydroxide). For example, 3D-MPL may be formulated with aluminium hydroxide (EP 0 689 454) or oil in water emulsions (WO 95/17210); QS21 may be advantageously formulated with cholesterol containing liposomes (WO 96/33739), oil in water emulsions (WO 95/17210) or alum (WO 98/15287); CpG may be formulated with alum (Davis et al. supra; Brazolot-Millan supra) or with other cationic carriers.

Combinations of immunostimulants are also preferred, in particular a combination of a monophosphoryl lipid A and a saponin derivative (WO 94/00153; WO 95/17210; WO 96/33739; WO 98/56414; WO 99/12565; WO 99/11241), more particularly the combination of QS21 and 3D-MPL as disclosed in WO 94/00153. Alternatively, a combination of CpG plus a saponin such as QS21 also forms a potent adjuvant for use in the present invention. Alternatively the saponin may be formulated in a liposome or in an Iscorn and combined with an immunostimulatory oligonucleotide.

Thus, suitable adjuvant systems include, for example, a combination of monophosphoryl lipid A, preferably 3D-MPL, together with an aluminium salt. An enhanced system involves the combination of a monophosphoryl lipid A and a saponin derivative particularly the combination of QS21 and 3D-MPL as disclosed in WO 94/00153, or a less reactogenic composition where the QS21 is quenched in cholesterol containing liposomes (DQ) as disclosed in WO 96/33739. This combination may additionally comprise an immunostimulatory oligonucleotide.

A particularly potent adjuvant formulation involving QS21, 3D-MPL & tocopherol in an oil in water emulsion is described in WO 95/17210 and is another preferred formulation for use in the invention.

Another preferred formulation comprises a CpG oligonucleotide alone or together with an aluminium salt.

In a further aspect of the present invention there is provided a method of manufacture of a vaccine formulation as herein described, wherein the method comprises admixing a polypeptide according to the invention with a suitable adjuvant.

Particularly preferred adjuvant combinations for use in the formulations according to the invention are as follows:

i) 3D-MPL+QS21 in a liposome ii) Alum+3D-MPL iii) Alum+QS21 in a liposome+3D-MPL iv) Alum+CpG v) 3D-MPL+QS21+oil in water emulsion vi) CpG Administration of the pharmaceutical composition may take the form of one or of more than one individual dose, for example as repeat doses of the same polypeptide containing composition, or in a heterologous "prime-boost" vaccination regime. A heterologous prime-boost regime uses administration of different forms of vaccine in the prime and the boost, each of which may itself include two or more administrations. The priming composition and the boosting composition will have at least one antigen in common, although it is not necessarily an identical form of the antigen, it may be a different form of the same antigen.

Prime boost immunisations according to the invention may be performed with a combination of protein and DNA-based formulations. Such a strategy is considered to be effective in inducing broad immune responses. Adjuvanted protein vaccines induce mainly antibodies and T helper immune responses, while delivery of DNA as a plasmid or a live vector induces strong cytotoxic T lymphocyte (CTL) responses. Thus, the combination of protein and DNA vaccination will provide for a wide variety of immune responses. This is particularly relevant in the context of HIV, since both neutralising antibodies and CTL are thought to be important for the immune defence against HIV.

In accordance with the invention a schedule for vaccination may comprise the sequential ("prime-boost") or simultaneous administration of polypeptide antigens and DNA encoding the polypeptides. The DNA may be delivered as naked DNA such as plasmid DNA or in the form of a recombinant live vector, e.g. a poxvirus vector, an adenovirus vector, a measles virus vector or any other suitable live vector. Protein antigens may be injected once or several times followed by one or more DNA administrations, or DNA may be used first for one or more administrations followed by one or more protein immunisations.

A particular example of prime-boost immunisation according to the invention involves priming with DNA in the form of a recombinant live vector such as a modified poxvirus vector, for example Modified Virus Ankara (MVA) or an alphavirus, for example Venezuelian Equine Encephalitis Virus, or an adenovirus vector, or a measles virus vector, followed by boosting with a protein, preferably an adjuvanted protein.

Thus the invention further provides a pharmaceutical kit comprising:
   a) a composition comprising a polypeptide comprising Nef or an immunogenic fragment or derivative thereof and p17 and/or p24 Gag or an immunogenic fragment or derivative thereof, wherein when both p17 and p24 Gag are present there is at least one HIV antigen or immunogenic fragment or derivative between them, together with a pharmaceutically acceptable excipient; and
   b) a composition comprising a polynucleotide encoding one or more of Nef and Gag or an immunogenic fragment or derivative of Nef or Gag containing a Nef or Gag epitope present in the polypeptide of a), together with a pharmaceutically acceptable excipient.

Preferably the polypeptide of a) further comprises RT or an immunogenic fragment or derivative thereof such as p51RT.

In an alternative embodiment the pharmaceutical kit comprises:
   a) a composition comprising a polynucleotide encoding a polypeptide comprising Nef or an immunogenic fragment or derivative thereof and p17 and/or p24 Gag or an immunogenic fragment or derivative thereof, wherein when both p17 and p24 Gag are present there is at least one HIV antigen or immunogenic fragment or derivative between them, together with a pharmaceutically acceptable excipient; and
   b) a composition comprising a polypeptide comprising one or more of Nef and Gag or an immunogenic fragment or derivative of Nef or Gag containing a Nef or Gag epitope present in the polypeptide of a), together with a pharmaceutically acceptable excipient.

Preferably the polynucleotide of a) encodes a polypeptide which further comprises RT or an immunogenic fragment or derivative thereof such as p51RT.

Preferred polypeptides and polynucleotides for use in a prime/boost kit according to the invention are the polypeptides and polynucleotides as described herein. Thus, the protein component of a protein/DNA type prime boost approach may be any of the preferred fusion proteins described herein. Likewise, the DNA component may be a polynucleotide encoding any of the preferred proteins.

Thus for example, the p24-RT-Nef-p17, p24-RT*-Nef-p17, p24-p51RT-Nef-p17, p24-p51RT*-Nef-p17, p17-p51RT-Nef or p17-p51RT*-Nef fusions or any of the p17-Nef fusions as described herein may be provided in a prime boost kit wherein the priming composition comprises the fusion protein and the boosting composition comprises a polynucleotide encoding the fusion protein, or the priming composition comprises the polynucleotide and the boosting composition comprises the fusion protein.

Both the priming composition and the boosting composition may be delivered in more than one dose. Furthermore the initial priming and boosting doses may be followed up with further doses which may be alternated to result in e.g. a DNA plasmid prime/protein boost/further DNA plasmid dose/further protein dose.

By codon optimisation it is meant that the polynucleotide sequence, is optimised to resemble the codon usage of genes in the desired expression system, for example a prokaryotic system such as *E. coli*. In particular, the codon usage in the sequence is optimised to resemble that of highly expressed *E. coli* genes.

The purpose of codon optimizing for expression in a recombinant system according to the invention is twofold: to improve expression levels of the recombinant product and to render expression products more homogeneous (obtain a more homogeneous expression pattern). Improved homogeneity means that there are fewer irrelevant expression products such as truncates. Codon usage adaptation to *E. coli* expression can also eliminate the putative "frame-shift" sequences as well as premature termination and/or internal initiation sites.

The DNA code has 4 letters (A, T, C and G) and uses these to spell three letter "codons" which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons.

Where more than one codon is available to code for a given amino acid, it has been observed that the codon usage patterns of organisms are highly non-random. Different species show a different bias in their codon selection and, furthermore, utilisation of codons may be markedly different in a single species between genes which are expressed at high and low levels. This bias is different in viruses, plants, bacteria and mammalian cells, and some species show a stronger bias away from a random codon selection than others. For example, humans and other mammals are less strongly biased than certain bacteria or viruses. For these reasons, there is a significant probability that a viral gene from a mammalian virus expressed in *E. coli*, or a foreign or recombinant gene expressed in mammalian cells will have an inappropriate distribution of codons for efficient expression. It is believed that the presence in a heterologous DNA sequence of clusters of codons or an abundance of codons which are rarely observed in the host in which expression is to occur, is predictive of low heterologous expression levels in that host.

In the polynucleotides of the present invention, the codon usage pattern may thus be altered from that typical of human immunodeficiency viruses to more closely represent the codon bias of the target organism, e.g. *E. coli*.

There are a variety of publicly available programs useful for codon optimization, for example "CalcGene" (Hale and Thompson, Protein Expression and Purification 12: 185-189 (1998).

EXAMPLES

Example 1

Construction and Expression of HIV-1 p24-RT-Nef-p17 Fusion F4 and F4 Codon Optimized (co)

1. F4 Non-Codon-Optimised

HIV-1 gag p24 (capsid protein) and p17 (matrix protein), the reverse transcriptase and Nef proteins were expressed in *E. coli* B834 strain (B834 (DE3) is a methionine auxotroph parent of BL21 (DE3)), under the control of the bacteriophage T7 promoter (pET expression system).

They were expressed as a single fusion protein containing the complete sequence of the four proteins. Mature p24 coding sequence comes from HIV-1 BH10 molecular clone, mature p17 sequence and RT gene from HXB2 and Nef gene from the BRU isolate.

After induction, recombinant cells expressed significant levels of the p24-RT-Nef-p17 fusion that amounted to 10% of total protein.

When cells were grown and induced at 22° C., the p24-RT-Nef-p17 fusion protein was confined mainly to the soluble fraction of bacterial lysates (even after freezing/thawing). When grown at 30° C., around 30% of the recombinant protein was associated with the insoluble fraction.

The fusion protein p24-RT-Nef-p17 is made up of 1136 amino acids with a molecular mass of approximately 129 kDa. The full-length protein migrates to about 130 kDa on SDS gels. The protein has a theoretical isoeleectric point (pI) of 7.96 based on its amino acid sequence, confirmed by 2D-gel electrophoresis.

Details of the Recombinant Plasmid:

| | |
|---|---|
| name: | pRIT15436 (or lab name pET28b/p24-RT-Nef-p17) |
| host vector: | pET28b |
| replicon: | colE1 |
| selection: | kanamycin |
| promoter: | T7 |
| insert: | p24-RT-Nef-p17 fusion gene. |

Details of the Recombinant Protein:

p24-RT-Nef-p17 fusion protein: 1136 amino acids.

N-term-p24: 232a.a.-hinge: 2a.a.-RT: 562a.a.-hinge:2a.a.-Nef: 206a.a.-P17: 132a.a.-C-term Nucleotide and Amino-Acid Sequences:

Nucleotide Sequence

[SEQ ID NO: 1]

```
atggttatcgtgcagaacatccaggggcaaatggtacatcaggccatatcacctagaactttaaatgcatgggtaaaagt agtagaagagaaggctttcagcccagaagtaatacccatgttttcagcattatcagaaggagccaccccacaagattta aacaccatgctaaacacagtggggggacatcaagcagccatgcaaatgttaaaagagaccatcaatgaggaagctgc agaatgggatagagtacatccagtgcatgcagggcctattgcaccaggccagatgagagaaccaaggggaagtgaca tagcaggaactactagtacccttcaggaacaaataggatggatgacaaataatccacctatcccagtaggagaaattta taaaagatggataatcctgggattaaataaaatagtaagaatgtatagccctaccagcattctggacataagacaagga ccaaaagaaccttttagagactatgtagaccggttctataaaactctaagagccgagcaagcttcacaggaggtaaaaa attggatgacagaaaccttgttggtccaaaatgcgaacccagattgtaagactattttaaaagcattgggaccagcggct acactagaagaaatgatgacagcatgtcagggagtaggaggacccggccataaggcaagagttttgcatatgggcccc attagccctattgagactgtgtcagtaaaattaaagccaggaatggatggcccaaaagttaaacaatggccattgacagaagaaa aaataaaagcattagtagaaatttgtacagagatggaaaaggaagggaaaatttcaaaaattgggcctgaaaatccatacaatact ccagtatttgccataaagaaaaaagacagtactaaatggagaaaattagtagatttcagagaacttaataagagaactcaagactt ctgggaagttcaattaggaataccacatcccgcagggttaaaaaagaaaaaatcagtaacagtactggatgtgggtgatgcatat ttttcagttcccttagatgaagacttcaggaaatatactgcatttaccatacctagtataaacaatgagacaccagggattagatatca gtacaatgtgcttccacagggatggaaaggatcaccagcaatattccaaagtagcatgacaaaaatcttagagccttttagaaaac aaaatccagacatagttatctatcaatacatggatgatttgtatgtaggatctgacttagaaatagggcagcatagaacaaaaatag aggagctgagacaacatctgttgaggtggggacttaccacaccagacaaaaaacatcagaaagaacctccattccttaaaatgg gttatgaactccatcctgataaatggacagtacagcctatagtgctgccagaaaaagacagctggactgtcaatgacatacagaa gttagtgggaaattgaattgggcaagtcagatttacccagggattaaagtaaggcaattatgtaaactccttagaggaaccaaag cactaacagaagtaataccactaacagaagaagcagagctagaactggcagaaaacagagagattctaaaagaaccagtacat ggagtgtattatgacccatcaaaagacttaatagcagaaatacagaagcaggggcaaggccaatggacatatcaaatttatcaag agccatttaaaaatctgaaaacaggaaaatatgcaagaatgaggggtgcccacactaatgatgtaaaacaattaacagaggcag tgcaaaaaataaccacagaaagcatagtaatatggggaaagactcctaaatttaaactgcccatacaaaaggaaacatgggaaa catggtggacagagtattggcaagccacctggattcctgagtgggagtttgttaatacccctcctttagtgaaattatggtaccagtt agagaaagaacccatagtaggagcagaaaccttctatgtagatggggcagctaacagggagactaaattaggaaaagcagga tatgttactaatagaggaagacaaaaagttgtcaccctaactgacacaacaaatcagaagactgagttacaagcaatttatctagct ttgcaggattcgggattagaagtaaacatagtaacagactcacaatatgcattaggaatcattcaagcacaaccagatcaaagtga
```

-continued

```
atcagagttagtcaatcaaataatagagcagttaataaaaaaggaaaaggtctatctggcatgggtaccagcacacaaaggaatt
ggaggaaatgaacaagtagataaattagtcagtgctggaatcaggaaagtgctagctatgggtggcaagtggtcaaaaagtagt
gtggttggatggcctactgtaagggaaagaatgagacgagctgagccagcagcagatggggtgggagcagcatctcgagac
ctggaaaaacatggagcaatcacaagtagcaatacagcagctaccaatgctgcttgtgcctggctagaagcacaagaggagga
ggaggtggqttttccagtcacacctcaggtacctttaagaccaatgact
tacaaggcagctgtagatcttagccactttttaaaagaaaaggggggactggaagggctaattcactcccaacgaagacaagat
atccttgatctgtggatctaccacacacaaggctacttccctgattggcagaactacacaccagggccagggqtcagatatccac
tgacctttggatggtgctacaagctagtaccagttgagccagataaggtagaagaggccaataaaggagagaacaccagcttgt
tacaccctgtgagcctgcatggaatggatgaccctgagagagaagtgttagagtggaggtttgacagccgcctagcatttcatca
cgtggcccgagagctgcatccggagtacttcaagaactgcaggcctatgggtgcgagagcgtcagtattaagcggggagaa
ttagatcgatgggaaaaaattcggttaaggccaggggaaagaaaaaatataaattaaaacatatagtatgggcaagcagggag
ctagaacgattcgcagttaatcctggcctgttagaaacatcagaaggctgtagacaaatactgggacagctacaaccatccttca
gacaggatcagaagaacttagatcattatataatacagtagcaaccctctattgtgtgcatcaaaggatagagataaaagacacca
aggaagctttagacaagatagaggaagagcaaaacaaaagtaagaaaaaagcacagcaagcagcagctgacacaggacac
agcaatcaggtcagccaaaattactaa
``` p24 sequence is in bold
Nef sequence is underlined
Boxes: nucleotides introduced by genetic construction Amino-Acid Sequence

```
MVIVQNIQGQMVHQAISPRTLNAWVKVVEEKAFSPEVIPMFSALSEGATP      50
QDLNTMLNTVGGHQAAMQMLKETINEEAAEWDRVHPVHAGPIAPGQMREP     100
RGSDIAGTTSTLQEQIGWMTNNPPIPVGEIYKRWIILGLNKIVRMYSPTS     150
ILDIRQGPKEPFRDYVDRFYKTLRAEQASQEVKNWMTETLLVQNANPDCK     200
TILKALGPAATLEEMMTACQGVGGPGHKARVLHMGPISPIETVSVKLKPG     250
MDGPKVKQWPLTEEKIKALVEICTEMEKEGKISKIGPENPYNTPVFAIKK     300
KDSTKWRKLVDFRELNKRTQDFWEVQLGIPHPAGLKKKKSVTVLDVGDAY     350
FSVPLDEDFRKYTAFTIPSINNETPGIRYQYNVLPQGWKGSPAIFQSSMT     400
KILEPFRKQNPDIVIYQYMDDLYVGSDLEIGQHRTKIEELRQHLLRWGLT     450
TPDKKHQKEPPFLKMGYELHPDKWTVQPIVLPEKDSWTVNDIQKLVGKLN     500
WASQIYPGIKVRQLCKLLRGTKALTEVIPLREEAELELAENREILKEPVH     550
GVYYDPSKDLIAEIQKQGQGQWTYQIYQEPFKNLKTGKYARMRGAHTNDV     600
KQLTEAVQKITTESIVIWGKTPKFKLPIQKETWETWWTEYWQATWIPEWE     650
FVNTPPLVKLWYQLEKEPIVGAETFYVDGAANRETKLGKAGYVTNRGRQK     700
VVTLTDTTNQKTELQAIYLALQDSGLEVNIVTDSQYALGIIQAQPDQSES     750
ELVNQIIEQLIKKEKVYLAWVPAHKGIGGNEQVDKLVSAGIRKVLAMGGK     800
WSKSSVVGWPTVRERMRRAEPAADGVGAASRDLEKHGAITSSNTAATNAA     850
CAWLEAQEEEEVGFPVTPQVPLRPMTYKAAVDLSHFLKEKGGLEGLIHSQ     900
RRQDILDLWIYHTQGYFPDWQNYTPGPGVRYPLTFGWCYKLVPVEPDKVE     950
EANKGENTSLLHPVSLHGMDDPEREVLEWRFDSRLAFHHVARELHPEYFK    1000
NCREMGARASVLSGGELDRWEKIRLRPGKKKYKLKHIVWASRELERFAV    1050
NPGLLETSEGCRQILGQLQPSLQTGSEELRSLYNTVATLYCVHQRIEIKD    1100
TKEALDKIEEEQNKSKKKAQQAAADTGHSNQVSQNY                 1136
[SEQ ID NO:2]
```

P24 sequence: amino-acids 1-232 (in bold)
RT sequence: amino-acids 235-795
Nef sequence: amino-acids 798-1002
P17 sequence: amino-acids 1005-1136
Boxes: amino-acids introduced by genetic construction
K (Lysine): instead of Tryptophan (W). Mutation introduced to remover enzyme activity.

Expression of the Recombinant Protein:

In pET plasmid, the target gene (p24-RT-Nef-p17) is under control of the strong bacteriophage T7 promoter. This promoter is not recognized by E. coli RNA polymerase and is dependent on a source of T7 RNA polymerase in the host cell. B834 (DE3) host cell contains a chromosomal copy of the T7 RNA polymerase gene under lacUV5 control and expression is induced by the addition of IPTG to the bacterial culture.

Pre-cultures were grown, in shake flasks, at 37° C. to mid-log phase (A620:0.6) and then stored at 4° C. overnight (to avoid stationary phase cultures). Cultures were grown in LBT medium supplemented with 1% glucose and 50 μg/ml kanamycin. Addition of glucose to the growth medium has the advantage to reduce the basal recombinant protein expression (avoiding cAMP mediated derepression of lacUV5 promoter)

Ten ml of cultures stored overnight at 4° C. were used to inoculate 200 ml of LBT medium (without glucose) containing kanamycin. Cultures were grown at 30° C. and 22° C. and when O.D.620 reached 0.6, IPTG was added (1 mM final). Cultures were incubated for further 3, 5 and 18 hours (overnight). Samples were collected before and after 3, 5 and 18 hours induction.

Extract preparation was as follows:

Cell pellets were suspended in breaking buffer* (at a theoretical O.D. of 10) and disrupted by four passages in French press (at 20.000 psi or 1250 bars). Crude extracts (T) were centrifuged at 20.000 g for 30 min to separate the soluble (S) and insoluble (P) fractions.

*Breaking buffer: 50 mM Tris-HCL pH 8.0, 1 mM EDTA, 1 mM DTT+protease inhibitors cocktail (Complete/Boerhinger).

SDS-PAGE and Western Blot analysis:

Fractions corresponding to insoluble pellet (P), supernatant (S) and crude extract (T) were run on 10% reducing SDS-PAGE. p24-RT-Nef-p17 recombinant was detected by Coomassie blue staining and on Western blot (WB).

Coomassie staining: p24-RT-Nef-p17 protein appears as:
one band at ±130 kDa (fitting with calculated MW)
MW theoretical: 128.970 Daltons
MW apparent: 130 kDa Western blot analysis:

Reagents=—Monoclonal antibody to RT (p66/p51) Purchased from ABI (Advanced Biotechnologies) dilution: 1/5000
    Alkaline phosphatase-conjugate anti-mouse antibody dilution: 1/7500

Expression level: —Very strong p24-RT-Nef-p17 specific band after 20 h induction at 22° C., representing up to 10% of total protein (See FIG. 1A).

Recombinant protein "solubility":

"Fresh" cellular extracts (T, S, P fractions): With growth/induction at 22° C./20 h, almost all p24-RT-Nef-p17 fusion protein is recovered in the soluble fraction of cellular extract (FIG. 1A). With growth/induction at 30° C./20 h, around 30% of p24-RT-Nef-p17 protein is associated with the insoluble fraction (FIG. 1A).

"Freezing/thawing" (S2, P2 fractions):

Soluble (S1) fraction (20 h induction at 22° C.) conserved at −20° C. Thawed and centrifuged at 20.000 g/30 min: S2 and P2 (resuspended in 1/10 vol.)

Breaking buffer with DTT: almost all p24-RT-Nef-p17 fusion protein still soluble (only 1-5% precipitated) (see FIG. 1B)

Breaking buffer without DTT: 85-90% of p24-RT-Nef-p17 still soluble (FIG. 1B)

Figures:

FIG. 1A—Coomassie staining and western blot.
    FIG. 1B—p24-RT-Nef-p17 solubility assay
The F4 protein was purified using purification method I in Example 7.

The cell growth and induction conditions and cellular extracts preparation for the examples which follow are as described in Example 1 unless other conditions are specified (e.g. temperature, composition of breaking buffer).

2. F4 Codon-Optimised

The following polynucleotide sequence is codon optimized such that the codon usage resembles the codon usage in a highly expressed gene in *E. coli*. The amino acid sequence is identical to that given above for F4 non-codon optimized.

Nucleotide Sequence for F4co:

```
atggtcattgttcagaacatacagggccaaatggtccaccaggcaattagtccgcgaact
cttaatgcatgggtgaaggtcgtggaggaaaaggcattctcccggaggtcattccgatg
tttctgcgctatctgagggcgcaacgccgcaagaccttaataccatgcttaacacggta
ggcgggcaccaagccgctatgcaaatgctaaaagagactataaacgaagaggccgccgaa
tgggatcgagtgcaccccggtgcacgccggcccaattgcaccaggccagatgcgcgagccg
cgcgggtctgatattgcaggaactacgtctaccccttcaggagcagattgggtggatgact
aacaatccaccaatcccggtcggagagatctataagaggtggatcatactgggactaaac
aagatagtccgcatgtattctccgacttctatactggatatacgccaaggcccaaaggag
ccgttcagggactatgtcgaccgattctataagacccttcgcgcagagcaggcatcccag
gaggtcaaaaattggatgacagaaactcttttggtgcagaatgcgaatccggattgtaaa
acaattttaaaggctctaggaccggccgcaacgctagaagagatgatgacggcttgtcag
ggagtcggtggaccggggcataaagcccgcgtcttacacatcggcccgatatctccgat
agaaacagtttcggtcaagcttaaaccaggggatggatcgtccaaaggtcaagcagtggcc
gctaacggaagagaagattaaggcgctcgtagagatttgtactgaaatggagaaggaagg
caagataagcaagatcgggccagagaacccgtacaatacaccggtatttgcaataaagaa
aaaggattcaacaaaatggcgaaagcttgtagattttagggaactaaacaagcgaaccca
```

-continued

```
agactttgggaagtccaactagggatcccacatccagccggtctaaagaagaagaaatc
ggtcacagtcctggatgtaggagacgcatattttagtgtaccgcttgatgaggacttccg
aaagtatactgcgtttactataccgagcataaacaatgaaacgccaggcattcgctatca
gtacaacgtgctcccgcagggctggaaggggtctccggcgatatttcagagctgtatgac
aaaaatacttgaaccattccgaaagcagaatccggatattgtaatttaccaatacatgga
cgatctctatgtgggctcggatctagaaattgggcagcatcgcactaagattgaggaact
gaggaaacatctgcttcgatgggcctcactactcccgacaagaagcaccagaaggagcc
gccgttcctaaagatgggctacgagcttcatccggacaagtggacagtacagccgatagt
gctgcccgaaaaggattcttggaccgtaaatgatattcagaaactagtcggcaagcttaa
ctgggcctctcagatttacccaggcattaaggtccgacagctttgcaagctactgagggg
aactaaggctctaacagaggtcatcccattaacggaggaagcagagcttgagctggcaga
gaatcgcgaaattcttaaggagccggtgcacggggtatactacgaccccctccaaggacct
tatagccgagatccagaagcagggggcagggccaatggacgtaccagatatatcaagaacc
gtttaagaatctgaagactgggaagtacgcgcgcatgcgagggctcatactaatgatgt
aaagcaacttacggaagcagtacaaaagattactactgagtctattgtgatatggggcaa
gacccaaagttcaagctgcccatacagaaggaaacatgggaaacatggtggactgaata
ttggcaagctacctggattccagaatgggaatttgtcaacacgccgccacttgttaagct
ttggtaccagcttgaaaaggagccgatagtaggggcagagacctttctatgtcgatggcgc
cgcgaatcgcgaaacgaagctaggcaaggcgggatacgtgactaataggggccgccaaaa
ggtcgtaaccctttacggataccaccaatcagaagactgaactacaagcgatttaccttgc
acttcaggatagtggcctagaggtcaacatagtcacggactctcaatatgcgcttggcat
tattcaagcgcagccagatcaaagcgaaagcgagcttgtaaaccaaataatagaacagct
tataaagaaagagaaggtatatctggcctgggtccccgctcacaagggaattggcggcaa
tgagcaagtggacaagctagtcagcgctgggattcgcaaggttctt┌gcgatg┐gggta
agtggtctaagtctagcgtagtcggctggccgacagtccgcgagcgcatgcgacgcgccg
aaccagccgcagatggcgtggggggcagcgtctagggatctggagaagcacggggctataa
cttccagtaacacggcggcgacgaacgccgcatgcgcatggttagaagcccaagaagagg
aagaagtagggtttccggtaactcccagctgccgttaaggccgatgacc
tataaggcagcggtggatctttctcacttccttaaggagaaagggggctggagggctta
attcacagccagaggcgacaggatattcttgatctgtggatttaccatacccagggtac
tttccggactggcagaattacaccccgggggccaggcgtgcgctatcccctgactttcggg
tggtgctacaaactagtcccagtggaacccgacaaggtcgaagaggctaataagggcgag
aacacttctcttcttcacccggtaagcctgcacgggatggatgacccagaacgagaggtt
ctagaatggaggttcgactctcgacttgcgttccatcacgtagcacgcgagctgcatcca
gaatatttcaagaactgc┌cgccca┐atgggcgccagggccagtgtacttagtggcggaga
actagatcgatgggaaaagatacgcctacgcccgggggggcaagaagaagtacaagcttaa
gcacattgtgtgggcctctcgcgaacttgagcgattcgcagtgaatccaggcctgcttga
gacgagtgaaggctgtaggcaaattctggggcagctacagccgagcctacagactggcag
cgaggagcttcgtagtctttataataccgtcgcgactctctactgcgttcatcaacgaat
tgaaataaaggatactaaagaggcccttgataaaattgaggaggaacagaataagtcgaa
aaagaaggcccagcaggccgccgccgacaccgggcacagcaaccaggtgtcccaaaacta
ctaa
[SEQ ID NO:3]
``` p24 sequence is in bold
Nef sequence is underlined
Boxes: nucleotides introduced by genetic construction The procedures used in relation to F4 non-codon optimized were applied for the codon-optimised sequence.

Details of the Recombinant Plasmid:

| | |
|---|---|
| name: | pRIT15513 (lab name: pET28b/p24-RT-Nef-p17) |
| host vector: | pET28b |
| replicon: | colE1 |
| selection: | kanamycin |
| promoter: | T7 |
| insert: | p24-RT-Nef-p17 fusion gene, codon-optimized |

The F4 codon-optimised gene was expressed in *E. coli* BLR(DE3) cells, a recA⁻ derivative of B834(DE3) strain. RecA mutation prevents the putatitve production of lambda phages.

Pre-cultures were grown, in shake flasks, at 37° C. to mid-log phase ($A_{620}$:0.6) and then stored at 4° C. overnight (to avoid stationary phase cultures).

Cultures were grown in LBT medium supplemented with 1% glucose and 50 μg/ml kanamycin. Addition of glucose to the growth medium has the advantage to reduce the basal recombinant protein expression (avoiding cAMP mediated derepression of lacUV5 promoter).

Ten ml of cultures stored overnight at 4° C. were used to inoculate 200 ml of LBT medium (without glucose) containing kanamycin. Cultures were grown at 37° C. and when $O.D._{620}$ reached 0.6, IPTG was added (1 mM final). Cultures were incubated for further 19 hours (overnight), at 22° C. Samples were collected before and 19 hours induction.

Extract preparation was as follows:

Cell pellets were resuspended in sample buffer (at a theoretical O.D. of 10), boiled and directly loaded on SDS-PAGE.

SDS-PAGE and Western Blot analysis:

Crude extracts samples were run on 10% reducing SDS-PAGE.

p24-RT-Nef-p17 recombinant protein is detected by Coomassie blue staining (FIG. 2) and on Western blot.

| | |
|---|---|
| Coomassie staining: | p24-RT-Nef-p17 protein appears as: |
| | one band at ±130 kDa (fitting with calculated MW) |
| MW theoretical: | 128.967 Daltons |
| MW apparent: | 130 kDa |
| Western blot analysis: | |
| Reagents = | Rabbit polyclonal anti RT (rabbit PO3L16) |
| | dilution: 1/10.000 |
| | Rabbit polyclonal anti Nef-Tat (rabbit 388) |
| | dilution 1/10.000 |
| | Alkaline phosphatase-conjugate anti-rabbit antibody. |
| | dilution: 1/7500 |

After induction at 22° C. over 19 hours, recombinant BLR (DE3) cells expressed the F4 fusion at a very high level ranging from 10-15% of total protein.

In comparison with F4 from the native gene, the F4 recombinant product profile from the codon-optimised gene is slightly simplified. The major F4-related band at 60 kDa, as well as minor bands below, disappeared (see FIG. 2). Compared to the B834(DE3) recombinant strain expressing F4, the BLR(DE3) strain producing F4co has the following advantages: higher production of F4 full-length protein, less complex band pattern of recombinant product.

Example 2

Construction and Expression of P51 RT (Truncated, Codon-Optimised RT)

The RT/p66 region between amino acids 428-448 is susceptible to E. coli proteases. The P51 construct terminates at Leu 427 resulting in the elimination of RNaseH domain (see RT sequence alignment in FIG. 3).

The putative E. coli "frameshift" sequences identified in RT native gene sequence were also eliminated (by codon-optimization of p51 gene).

p51 Synthetic Gene Design/Construction:

The sequence of the synthetic p51 gene was designed according to E. coli codon usage. Thus it was codon optimized such that the codon usage resembles the codon usage in a highly expressed gene in E. coli. The synthetic gene was constructed as follows: 32 oligonucleotides were assembled in a single-step PCR. In a second PCR the full-length assembly was amplified using the ends primers and the resulting PCR product was cloned into pGEM-T intermediate plasmid. After correction of point errors introduced during gene synthesis, the p51 synthetic gene was cloned into pET29a expression plasmid. This recombinant plasmid was used to transform B834 (DE3) cells.

Recombinant Protein Characteristics:

P51 RT Nucleotide Sequence

```
atcagtactggtccgatctctccgatagaaacagtttcggtcaagcttaaaccagggatg    60
gatggtccaaaggtcaagcagtggccgctaacggaagagaagattaaggcgctcgtagag   120
atttgtactgaaatggagaaggaaggcaagataagcaagatcgggccagagaacccgtac   180
aatacaccggtatttgcaataaagaagaaggattcaacaaaatggcgaaagcttgtagat   240
tttagggaactaaacaagcgaacccaagacttttgggaagtccaactaggtatcccacat   300
ccagccggtctaaagaagaagaaatcggtcacagtcctggatgtaggagacgcatatttt   360
agtgtaccgcttgatgaggacttccgaaagtatactgcgtttactataccgagcataaac   420
aatgaaacgccaggcattcgctatcagtacaacgtgctcccgcagggctggaagggggtct   480
ccggcgatatttcagagctctatgacaaaaatacttgaaccattccgaaagcagaatccg   540
gatattgtaatttaccaatacatggacgatctctatgtgggctcggatctagaaattggg   600
cagcatcgcactaagattgaggaactgaggcaacatctgcttcgatggggcctcactact   660
cccgacaagaagcaccagaaggagccgccgttcctaaagatgggctacgagcttcatccg   720
gacaagtggacagtacagccgatagtgctgcccgaaaaggattcttggaccgtaaatgat   780
attcagaaactagtcggcaagcttaactgggcctctcagatttacccaggcattaaggtc   840
cgacagctttgcaagctactgaggggaactaaggctctaacagaggtcatcccattaacg   900
gaggaagcagagcttgagctggcagagaatcgcgaaattcttaaggagccggtgcacggg   960
gtatactacgaccccctccaaggaccttatagccgagatccagaagcaggggcagggccaa  1020
tggacgtaccagatatatcaagaaccgtttaagaatctgaagactgggaagtacgcgcgc  1080
atgcgaggggctcatactaatgatgtaaagcaacttacggaagcagtacaaaagattact  1140
actgagtctattgtgatatggggcaagaccccaaagttcaagctgcccatacagaaggaa  1200
acatgggaaacatggtggactgaatattggcaagctacctggattccagaatgggaattt  1260
gtcaacacgccgccgcctggtaaaactgaaggcctgctagctaa                  1302
[SEQ ID NO:4]
```

Boxes: amino-acids introduced by genetic construction

Amino-Acid Sequence:

```
MSTGPISPIETVSVKLKPGMDGPKVKQWPLTEEKIKALVEICTEMEKEGKISKIGPENPY    60
NTPVFAIKKKDSTKWRKLVDFRELNKRTQDFWEVQLGIPHPAGLKKKKSVTVLDVGDAYF   120
SVPLDEDFRKYTAFTIPSINNETPGIRYQYNVLPQGWKGSPAIFQSSMTKILEPFRKQNP   180
DIVIYQYMDDLYVGSDLEIGQHRTKIEELRQHLLRWGLTTPDKKHQKEPPFLKMGYELHP   240
DKWTVQPIVLPEKDSWTVNDIQKLVGKLNWASQIYPGIKVRQLCKLLRGTKALTEVIPLT   300
EEAELELAENREILKEPVHGVYYDPSKDLIAEIQKQGQGQWTYQIYQEPPFKNLKTGKYAR   360
MRGAHTNDVKQLTEAVQKITTESIVIWGKTPKFKLPIQKETWETWWTEYWQATWIPEWEF   420
VNTPPLVKLRPAS                                                  433
[SEQ ID NO:5]
```

Boxes: amino-acids introduced by genetic construction.

K (Lysine): instead of Tryptophan (W). Mutation introduced to remover enzyme activity.

Length, Molecular Weight, Isoelectric Point (IP):
433 AA, MW: 50.3 kDa, IP: 9.08 p51 Expression in B834(DE3) Cells:
P51 expression level and recombinant protein solubility were evaluated, in parallel to RT/p66 production strain.

p51 Expression Level:
Induction condition: cells grown/induced at 37° C. (+1 mM IPTG), during 5 hours.
Breaking buffer: 50 mM Tris/HCl, pH: 7.5, 1 mM EDTA, +/−1 mM DTT.
Western blot analysis:
Reagents:
rabbit polyclonal anti RT (rabbit PO3L16) (dilution: 1/10, 000)
Alkaline phosphatase-conjugate anti-rabbit antibody (dilution: 1/7500)
Cellular fractions corresponding to crude extracts (T), insoluble pellet (P) and supernatant (S) were run on 10% reducing SDS-PAGE.
As illustrated on Coomassie stained gel and Western Blot (FIG. 4) very high expression of P51 (15-20% of total protein) was observed, higher than that observed for P66.
For both p51 and p66 proteins (after 5 h induction at 37° C.), 80% of the recombinant products were recovered in the soluble fraction (S1) of cellular extracts (See FIG. 4). When expressed at 30° C., 99% of recombinant proteins were associated with the soluble fraction (data not shown).
The p51 Western Blot pattern was multiband, but less complex than that observed for P66.

Figure 5:
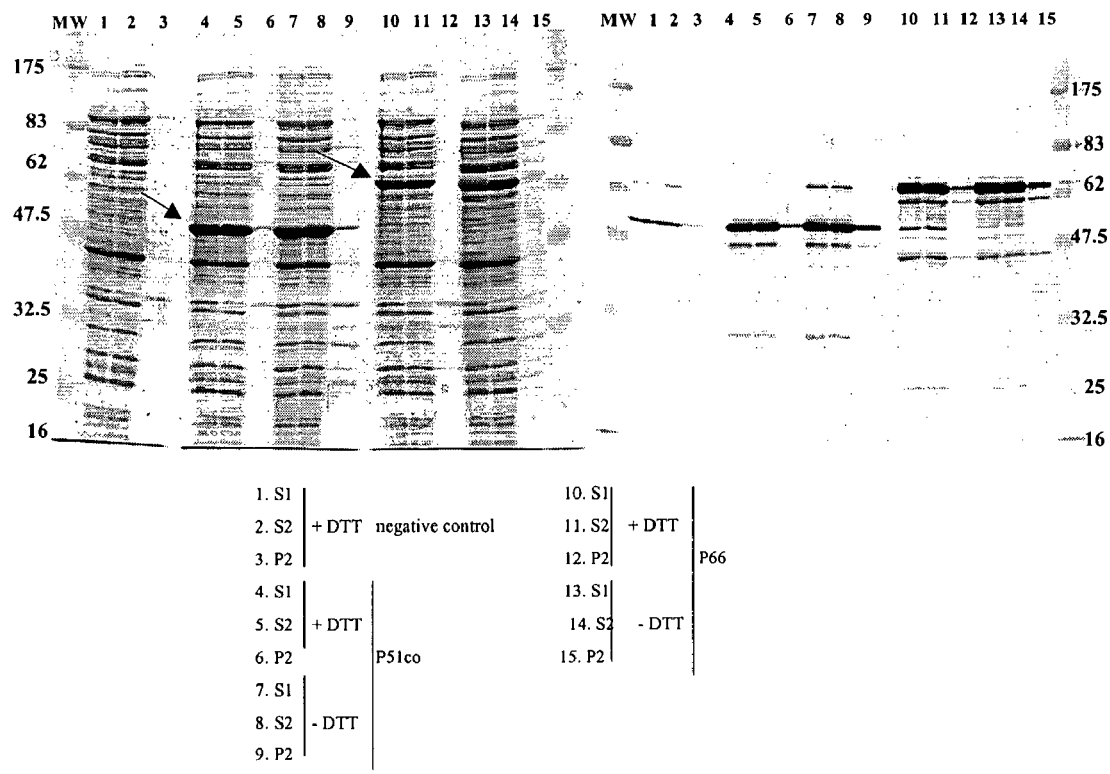
FIG. 5 is images of a Coomassie stained gel (left panel) and western blot (right panel) illustrating a solubility of RT/P51 and RT/p66.

Solubility Assay
Solubility assay: Freezing/thawing of Soluble (S1) fraction (5 h induction, 37° C.) prepared under reducing (breaking buffer with DTT) and non-reducing conditions. After thawing, S1 samples were centrifuged at 20.000 g/30 minutes, generating S2 and P2 (p2 is resuspended in 1/10 vol).
After freezing/thawing of soluble fractions (S1), prepared under reducing as well as non-reducing conditions, 99% of p51 and p66 are still recovered in soluble (S2) fraction. Only 1% is found in the precipitate (P2). This is shown in FIG. 5.

Example 3

Construction and Expression of p17-Nef and Nef-p17 with or without Linker

The double fusion proteins were constructed with and without linkers. The linkers aimed to decrease potential interactions between the two fusion partners and are as follows:

```
Nef-GSGGGP-P17 and p17-GSGGGP-Nef
```

Recombinant Plasmids Construction:
pET29a/Nef-p17 Expression Vector:
Nef-p17 fusion gene was amplified by PCR from the F4 recombinant plasmid. The PCR product was cloned into the intermediate pGEM-T cloning vector and subsequently into the pET29a expression vector.
pET28b/p17-Nef Expression Vector:
Nef gene was amplified by PCR from the F4 recombinant plasmid. The PCR product was cloned into the intermediate pGEM-T cloning vector and subsequently into the pET28b/p17 expression vector, as a C-terminal in frame fusion with the p17 gene.
pET29a/Nef-Linker-p17 and pET28b/p17-Linker-Nef Expression Vector:
A 18 bp DNA fragment coding for the hexapeptide linker (GSGGGP; SEQ ID NO:20) was inserted between Nef and p17 fusion partners, by site-directed mutagenesis (using the "GeneTailor Site-Directed Mutagenesis System", Invitrogen).

Recombinant Protein Characteristics:
Length, Molecular Weight, Isoelectric Point (IP)

```
Nef-p17 (named NP): 340 AA, MW: 38.5 kDa, IP:7.48
Nef-GSGGGP-P17 (named NLP): 346 AA, MW:38.9 kDa, IP: 7.48
p-17-Nef (named PN): 342 AA, MW: 38.7 kDa, IP: 7.19
p17-GSGGGP-Nef (named PLN): 348 AA, MW:39.1kDa, IP:N7.19
```

Amino-Acid Sequences and Polynucleotide Sequences:
Nef-p17 Nucleotide Sequence

[SEQ ID NO:6]

```
Atgggtggcaagtggtcaaaaagtagtgtggttggatggcctactgtaagggaaagaatg    60

Agacgagctgagccagcagcagatggggtgggagcagcatctcgagacctggaaaaacat   120

Ggagcaatcacaagtagcaatacagcagctaccaatgctgcttgtgcctggctagaagca   180

Caagaggaggaggaggtgggttttccagtcacacctcaggtacctttaagaccaatgact   240

Tacaaggcagctgtagatcttagccacttttaaaagaaaaggggggactggaagggcta   300

Attcactcccaacgaagacaagatatccttgatctgtggatctaccacacacaaggctac   360

Ttccctgattggcagaactacacaccagggccaggggtcagatatccactgacctttgga   420

Tggtgctacaagctagtaccagttgagccagataaggtagaagaggccaataaaggagag   480
```

-continued

```
Aacaccagcttgttacaccctgtgagcctgcatggaatggatgaccctgagagagaagtg    540

Ttagagtggaggtttgacagccgcctagcatttcatcacgtggcccgagagctgcatccg    600

Gagtacttcaagaactgcaggcctatgggtgcgagagcgtcagtattaagcggggagaa     660

Ttagatcgatgggaaaaaattcggttaaggccaggggggaaagaaaaaatataaattaaaa  720

Catatagtatgggcaagcagggagctagaacgattcgcagttaatcctggcctgttagaa   780

Acatcagaaggctgtagacaaatactgggacagctacaaccatcccttcagacaggatca   840

Gaagaacttagatcattatataatacagtagcaaccctctattgtgtgcatcaaaggata   900

Gagataaaagacaccaaggaagctttagacaagatagaggaagagcaaaacaaaagtaag   960

Aaaaaagcacagcaagcagcagctgacacaggacacagcaatcaggtcagccaaaattac  1020

Taa                                                            1023
```

Nef-p17 (NP)

```
MGGKWSKSSVVGWPTVRERMRRAEPAADGVGAASRDLEKHGAITSSNTAATNAACAWLEA    60
QEEEEVGFPVTPQVPLRPMTYKAAVDLSHFLKEKGGLEGLIHSQRRQDILDLWIYHTQGY   120
FPDWQNYTPGPGVRYPLTFGWCYKLVPVEPDKVEEANKGENTSLLHPVSLHGMDDPEREV   180
LEWRFDSRLAFHHVARELHPEYFKNCREMGARASVLSGGELDRWEKIRLRPGGKKKYKLK   240
HIVWASRELERFAVNPGLLETSEGCRQILGQLQPSLQTGSEELRSLYNTVATLYCVHQRI   300
EIKDTKEALDKIEEEQNKSKKKAQQAAADTGHSNQVSQNY                      340
[SEQ ID NO:7]
```

Box: amino-acids introduced by genetic construction.
Nef sequence is in bold.

P17-Nef Nucleotide Sequence:

```
                                                          [SEQ ID NO:8]
Atgggtgcgagagcgtcagtattaagcggggagaattagatcgatgggaaaaaattcgg     60

Ttaaggccaggggggaaagaaaaaatataaattaaaacatatagtatgggcaagcagggag  120

Ctagaacgattcgcagttaatcctggcctgttagaaacatcagaaggctgtagacaaata   180

Ctgggacagctacaaccatcccttcagacaggatcagaagaacttagatcattatataat   240

Acagtagcaaccctctattgtgtgcatcaaaggatagagataaaagacaccaaggaagct   300

Ttagacaagatagaggaagagcaaaacaaaagtaagaaaaaagcacagcaagcagcagct   360

Gacacaggacacagcaatcaggtcagccaaaattacctcgacaggcctatgggtggcaag   420

Tggtcaaaaagtagtgtggttggatggcctactgtaagggaaagaatgagacgagctgag   480

Ccagcagcagatggggtgggagcagcatctcgagacctgaaaaacatggagcaatcaca    540

Agtagcaatacagcagctaccaatgctgcttgtgcctggctagaagcacaagaggaggag   600

Gaggtgggttttccagtcacacctcaggtacctttaagaccaatgacttacaaggcagct   660

Gtagatcttagccactttttaaaagaaaaggggggactggaagggctaattcactcccaa   720

Cgaagacaagatatccttgatctgtggatctaccacacacaaggctacttccctgattgg   780

Cagaactacacaccagggccaggggtcagatatccactgacctttggatggtgctacaag   840

Ctagtaccagttgagccagataaggtagaagaggccaataaaggagagaacaccagcttg   900

Ttacaccctgtgagcctgcatggaatggatgaccctgagagagaagtgttagagtggagg   960

Tttgacagccgcctagcatttcatcacgtggcccgagagctgcatccggagtacttcaag  1020

Aactgctaa                                                     1029
```

P17-Nef (PN)

```
MGARASVLSGGELDRWEKIRLRPGGKKKYKLKHIVWASRELERFAVNPGLLETSEGCRQI    60
LGQLQPSLQTGSEELRSLYNTVATYLCVHQRIEIKDTKEALDKIEEEQNKSKKKAQQAAA   120
DTGHSNQVSQNYLDRHMGGKWSKSSVVGWPTVRERMRRAEPAADGVGAASRDLEKHGAIT   180
SSNTAATNAACAWLEAQEEEEVGFPVTPQVPLRPMTYKAAVDLSHFLKEKGGLEGLIHSQ   240
RRQDILDLWIYHTQGYFPDWQNYTPGPGVRYPLTFGWCYKLVPVEPDKVEEANKGENTSL   300
LHPVSLHGMDDPEREVLEWRFDSRLAFHHVARELHPEYFKCN                    342
[SEQ ID NO:9]
```

Box: amino-acids introduced by genetic construction.
p17 sequence is in bold.

Nef-Linker-p17 Nucleotide Sequence:

[SEQ ID NO:10]

```
Atgggtggcaagtggtcaaaaagtagtgtggttggatggcctactgtaagggaaagaatg    60
Agacgagctgagccagcagcagatggggtgggagcagcatctcgagacctggaaaaacat   120
Ggagcaatcacaagtagcaatacagcagctaccaatgctgcttgtgcctggctagaagca   180
Caagaggaggaggaggtgggttttccagtcacacctcaggtacctttaagaccaatgact   240
Tacaaggcagctgtagatcttagccactttttaaaagaaaagggggggactggaagggcta   300
Attcactcccaacgaagacaagatatccttgatctgtggatctaccacacacaaggctac   360
Ttccctgattggcagaactacacaccagggccaggggtcagatatccactgacctttgga   420
Tggtgctacaagctagtaccagttgagccagataaggtagaagaggccaataaaggagag   480
Aacaccagcttgttacaccctgtgagcctgcatggaatggatgaccctgagagagaagtg   540
Ttagagtggaggtttgacagccgcctagcatttcatcacgtggcccgagagctgcatccg   600
Gagtacttcaagaactgcaggcctggatccgtggcggccctatgggtgcgagagcgtca   660
Gtattaagcggggagaattagatcgatgggaaaaaattcggttaaggccaggggaaag    720
Aaaaatataaattaaaacatatagtatgggcaagcagggagctagaacgattcgcagtt   780
Aatcctggcctgttagaaacatcagaaggctgtagacaaatactgggacagctacaacca   840
Tcccttcagacaggatcagaagaacttagatcattatataatacagtagcaaccctctat   900
Tgtgtgcatcaaaggatagagataaaagacaccaaggaagctttagacaagatagaggaa   960
Gagcaaaacaaaagtaagaaaaaagcacagcaagcagcagctgacacaggacacagcaat  1020
Caggtcagccaaaattactaa                                        1041
```

```
MGGKWSKSSVVGWPTVRERMRRAEPAADGVGAASRDLEKHGAITSSNTAATNAACAWLEA    60
QEEEEVGFPVTPQVPLRPMTYKAAVDLSHFLKEKGGLEGLIHSQRRQDILDLWIYHTQGY   120
FPDWQNYTPGPGVRYPLTFGWCYKLVPVEPDKVEEANKGENTSLLHPVSLHGMDDPEREV   180
LEWRFDSRLAFHHVARELHPEYFKNCRPGSGGGPMGARASVLSGGELDRWEKIRLRPGGK   240
KKYKLKHIVWASRELERFAVNPGLLETSEGCRQILGQLQPSLQTGSEELRSLYNTVATLY   300
CVHQRIEIKDTKEALDKIEEEQNKSKKKAQQAAADTGHSNQVSQNY                346
[SEQ ID NO:11]
```

Hexapeptide linker
Box: amino-acids introduced by genetic construction.

P17-Linker-Nef Nucleotide Sequence:

[SEQ ID NO:12]

```
Atgggtgcgagagcgtcagtattaagcggggagaattagatcgatgggaaaaaattcgg    60
Ttaaggccaggggaaagaaaaaatataaattaaaacatatagtatgggcaagcagggag   120
Ctagaacgattcgcagttaatcctggcctgttagaaacatcagaaggctgtagacaaata   180
Ctgggacagctacaaccatcccttcagacaggatcagaagaacttagatcattatataat   240
```

-continued

```
Acagtagcaaccctctattgtgtgcatcaaaggatagagataaaagacaccaaggaagct    300
Ttagacaagatagaggaagagcaaaacaaaagtaagaaaaaagcacagcaagcagcagct    360
Gacacaggacacagcaatcaggtcagccaaaattacctcgacaggcctggatccggtggc    420
Ggtcctatgggtggcaagtggtcaaaaagtagtgtggttggatggcctactgtaagggaa    480
Agaatgagacgagctgagccagcagcagatgggtgggagcagcatctcgagacctggaa     540
Aaacatggagcaatcacaagtagcaatacagcagctaccaatgctgcttgtgcctggcta    600
Gaagcacaagaggaggaggaggtgggttttccagtcacacctcaggtacctttaagacca    660
Atgacttacaaggcagctgtagatcttagccactttttaaaagaaaaggggggactggaa    720
Gggctaattcactcccaacgaagacaagatatccttgatctgtggatctaccacacacaa    780
Ggctacttccctgattggcagaactacacaccagggccagggtcagatatccactgacc    840
Tttggatggtgctacaagctagtaccagttgagccagataaggtagaagaggccaataaa    900
Ggagagaacaccagcttgttcaccctgtgagcctgcatggaatggatgaccctgagaga     960
Gaagtgttagagtggaggtttgacagccgcctagcatttcatcacgtggcccgagagctg   1020
Catccggagtacttcaagaactgctaa                                     1047
```

P17-Linker-Nef (PLN)

```
MGARASVLSGGELDRWEKIRLRPGGKKKYKLKHIVWASRELERFAVNPGLLETSEGCRQI     60
LGQLQPSLQTGSEELRSLYNTVATLYCVHQRIEIKDTKEALDKIEEEQNKSKKKAQQAAA    120
DTGHSNQVSQNYLDRWGSGGGPMGGKWSKSSVVGWPTVRERMRRAEPAADGVGAASRDLE    180
KHGAITSSNTAATNAACAWLEAQEEEEVGFPVTPQVPLRPMTYKAAVDLSHFLKEKGGLE    240
GLIHSQRRQDILDLWIYHTQGYFPDWQNYTPGPGVRYPLTFGWCYKLVPVEPDKVEEANK    300
GENTSLLHPVSLHGMDDPEREVLEWRFDSRLAFHHVARELHPEYFKNC                348
[SEQ ID NO:13]
```

Hexapeptide linker
Box: amino-acids introduced by genetic construction.

Comparative Expression of Nef-p17, p17-Nef Fusions, with and w/o Linkers:

The four recombinant strains were induced at 30° C. over 3 hours, in parallel to F4 and Nef producing strains. Crude extracts were prepared and analyzed by Coomassie stained gel and Western blotting.

Western blot analysis:
Reagents:
  rabbit polyclonal anti RT (rabbit PO3L16) (dilution: 1/10,000)
  Alkaline phosphatase-conjugate anti-rabbit antibody (dilution: 1/7500)

Figure 6:
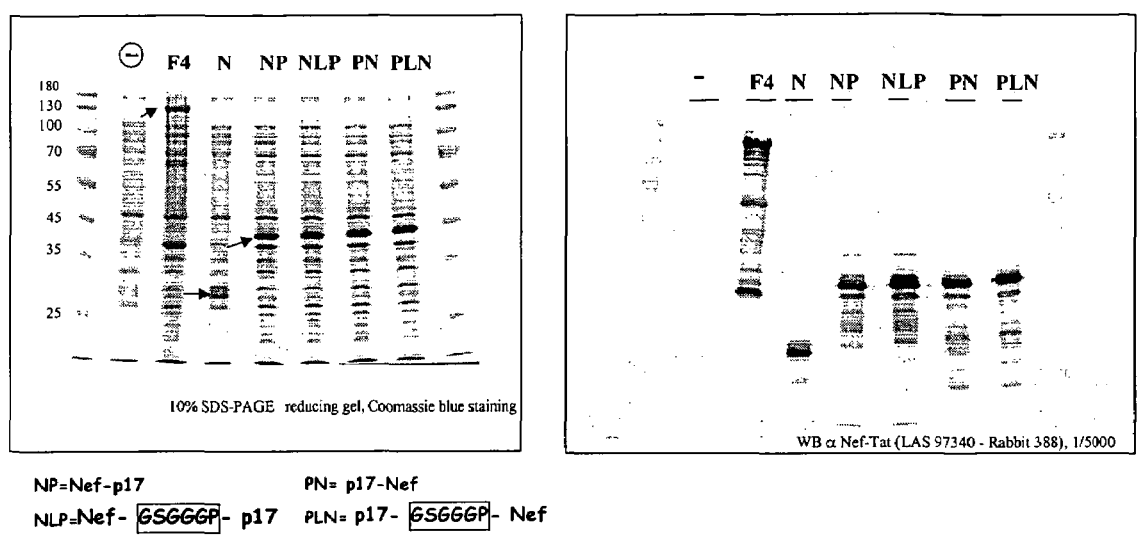
FIG. 6 is images of a Coomassie stained gel (left panel) and western blot (right panel) showing expression of Nef-p17 and p17-Nef fusions.

As illustrated in FIG. 6, Nef-p17 and p17-Nef fusions, with and w/o linker, are expressed at a high level (10% total proteins).

In the Western blot: the four double fusion constructs present a multi-band pattern, but less complex than what was observed for F4. When expressed alone, the Nef and p17 proteins present single band patterns.

Strains expressing Nef-p17 (NP) and p17-Nef (PN) fusions, without linker peptide, were further analysed (solubility assays, see below).

Nef-p17 and p17-Nef Solubility Assay:

Nef-p17 and p17-Nef proteins were induced, in parallel to F4 and Nef producing strains.

Induction condition: cells grown/induced at 30° C. (+1 mM IPTG), over 3 hours.

Breaking buffer: 50 mM Tris/HCl pH: 8, 50 mM NaCl, 1 mM EDTA

Fresh Cellular Extracts:

Cellular extracts were prepared (under non-reducing conditions) and fractions corresponding to crude extracts (T), insoluble pellet (P), and supernatant (S1) were analyzed on Coomassie stained gel and Western blot.

Figure 7:
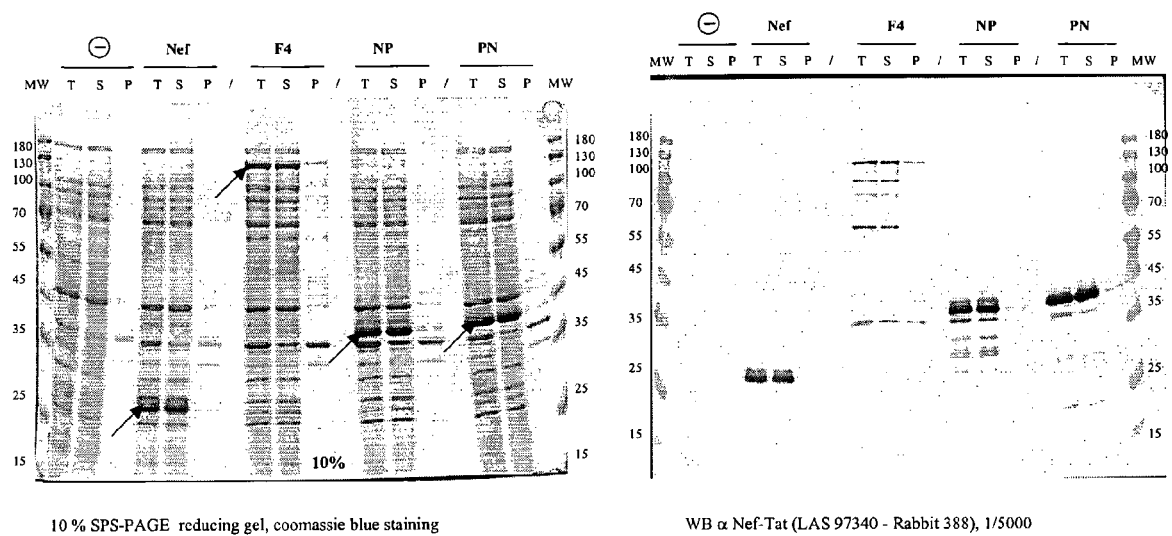
FIG. 7 is images of a Coomassie stained gel (left panel) and western blot (right panel) illustrating solubility of Nef-p17, p17-Nef and Nef proteins.

As illustrated in FIG. 7 on Coomassie stained gel and Western blot, almost all Nef-p17, p17-Nef, as well as Nef proteins are recovered in the soluble fraction (S) of cellular extracts. For F4 construct: 5-10% of recombinant protein already recovered in the pellet fraction.

Conclusions:

All double fusion constructs tested are highly expressed (>10% of total protein). P17-Nef and Nef-p17 fusion proteins are more soluble than F4. Both present a less complex WB pattern.

Example 4

Construction and Expression of p24-RT*-Nef-p17 (F4*)

F4* is a mutated version of the F4 (p24-RT/p66-Nef-p17) fusion where the Methionine at position 592 is replaced by a Lysine. This methionine is a putative internal transcriptional "start" site, as supported by N-terminal sequencing performed on a Q sepharose eluate sample of F4 purification experiment. Indeed, the major F4-related small band at 62 kDa present in the Q eluate sample starts at methionine 592.

Methionine is replaced by a lysine: RMR→RKR. The R KR motif is naturally present in clade A RT sequences.

The impact of this mutation on CD4-CD8 epitopes was evaluated:
-

Amino-Acid Sequence

```
MVIVQNIQGQMVHQAISPRTLNAWVKVVEEKAFSPEVIPMFSALSEGATP      50
QDLNTMLNTVGGHQAAMQMLKETINEEAAEWDRVHPVHAGPIAPGQMREP     100
RGSDIAGTTSTLQEQIGWMTNNPPIPVGEIYKRWIILGLNKIVRMYSPTS     150
ILDIRQGPKEPFRDYVDRFYKTLRAEQASQEVKNWMTETLLVQNANPDCK     200
TILKALGPAATLEEMMTACQGVGGPGHKARVL HM GPISPIETVSVKLKPG   250
MDGPKVKQWPLTEEKIKALVEICTEMEKEGKISKIGPENPYNTPVFAIKK     300
KDSTKWRKLVDFRELNKRTQDFWEVQLGIPHPAGLKKKKSVTVLDVGDAY     350
FSVPLDEDFRKYTAFTIPSINNETPGIRYQYNVLPQGWKGSPAIFQSSMT     400
KILEPFRKQNPDIVIYQYMDDLYVGSDLEIGQHRTKIEELRQHLLRWGLT     450
TPDKKHQKEPPFLKMGYELHPDKWTVQPIVLPEKDSWTVNDIQKLVGKLN     500
WASQIYPGIKVRQLCKLLRGTKALTEVIPLTEEAELELAENREILKEPVH     550
GVYYDPSKDLIAEIQKQGQGQWTYQIYQEPFKNLKTGKYARKRGAHTNDV     600
KQLTEAVQKITTESIVIWGKTPKFKLPIQKETWETWWTEYWQATWIPEWE     650
FVNTPPLVKLWYQLEKEPIVGAETFYVDGAANRETKLGKAGYVTNRGRQK     700
VVTLTDTTNQKTELQAIYLALQDSGLEVNIVTDSQYALGIIQAQPDQSES     750
ELVNQIIEQLIKKEKVYLAWVPAHKGIGGNEQVDKLVSAGIRKV LA MGGK   800
WSKSSVVGWPTVRERMRRAEPAADGVGAASRDLEKHGAITSSNTAATNAA     850
CAWLEAQEEEEVGFPVTPQVPLRPMTYKAAVDLSHFLKEKGGLEGLIHSQ     900
RRQDILDLWIYHTQGYFPDWQNYTPGPGVRYPLTFGWCYKLVPVEPDKVE     950
EANKGENTSLLHPVSLHGMDDPEREVLEWRFDSRLAFHHVARELHPEYFK    1000
NC RF MGARASVLSGGELDRWEKIRLRPGGKKKYKLKHIVWASRELERFAV   1050
NPGLLETSEGCRQILGQLQPSLQTGSEELRSLYNTVATLYCVHQRIEIKD    1100
TKEALDKIEEEQNKSKKKAQQAAADTGHSNQVSQNY                  1136
[SEQ ID NO:15]
```

P24 sequence: amino-acids 1-232 (in bold)
RT sequence: amino-acids 235-795
Nef sequence: amino-acids 798-1002
P17 sequence: amino-acids 1005-1136
Boxes: amino-acids introduced by genetic construction
K (Lysine): instead of Methionine (internal "start" codon)
K (Lysine) K: instead of Tryptophan (W). Mutation
introduced to remover enzyme activity.

F4* Expression in B834(DE3) Cells:

F4* recombinant strain was induced at 22° C. during 18 h, in parallel to F4 non-mutated construct. Crude extracts were prepared and analyzed by Coomassie stained gel and Western blotting.

Figure 8:
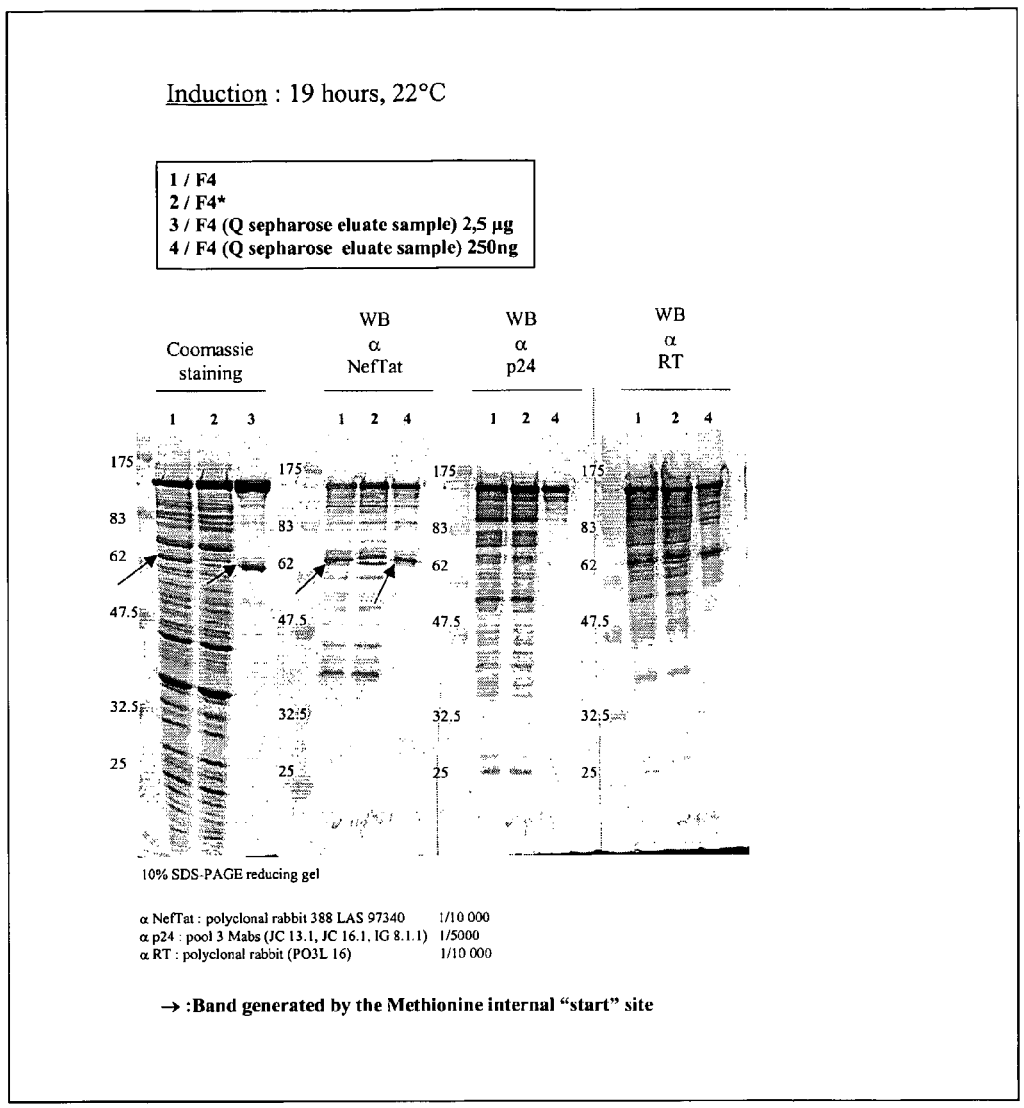
FIG. 8 is images of a Coomassie stained gel (left panel) and western blots (three right panels) showing expression of F4 fusion protein.

As illustrated in FIG. 8, F4* was expressed at a high level (10% total protein), slightly higher compared to F4 and the small 62 kDa band disappeared.

Western blot analysis:

Reagents:

pool 3 Mabs anti p24 (JC13.1, JC16.1, IG8.1.1) (dilution 1/5000)

rabbit polyclonal anti RT (rabbit PO3L16) (dilution: 1/10 000)

rabbit polyclonal anti Nef-Tat (rabbit 388) (dilution 1/10 000)

Alkaline phosphatase-conjugate anti-rabbit antibody (dilution: 1/7500)

Alkaline phosphatase-conjugate anti-mouse antibody (dilution: 1/7500)

Example 5

Construction and Expression of F3 and F3* (Mutated F3)

F3 (p17-p51-Nef) and F3* (p17-p51*-Nef) in which the putative internal Methionine initiation site replaced by Lysine.

F3 and F3* fusions could be used in combination with p24.

Recombinant Plasmids Construction:

F3: The sequence encoding p51 was excized (as ScaI and StuI DNA fragment) from pET29a/p51 expression plasmid and ligated into pET28b/p17-Nef plasmid, at the StuI site (located between p17 and Nef gene), as an in frame fusion with p17 and Nef sequences. The resulting fusion construct p17-p51-Nef is named F3.

F3*: Mutation of the putative internal methionine initiation site was achieved using the "Gene Tailor Site-Directed Mutagenesis system" (Invitrogen), generating F3* construct.

F3 and F3* plasmids were used to transform B834 (DE3) cells.

Recombinant Protein Characteristics:

N-term p17:134a.a. - hinge:2a.a. - p51/p51*:426a.a. - hinge:2a.a. - Nef:206a.a. C-term Length Molecular Weight, Isoelectric Point (IP)
770 AA, 88.5 kDa, IP: 8.58
Nucleotide Sequence (for F3*)

```
atgggtgcgagagcgtcagtattaagcgggggagaattagatcgatgggaaaaaattcgg      60
ttaaggccaggggggaaagaaaaaatataaattaaaacatatagtatgggcaagcagggag    120
ctagaacgattcgcagttaatcctggcctgttagaaacatcagaaggctgtagacaaata    180
ctgggacagctacaaccatcccttcagacaggatcagaagaacttagatcattatataat    240
acagtagcaaccctctattgtgtgcatcaaaggatagagataaaagacaccaaggaagct    300
ttagacaagatagaggaagagcaaaacaaaagtaagaaaaaagcacaagcaagcagcagct    360
gacacaggacacagcaatcaggtcagccaaaattacctcgac aggact GGTCCGATCTCT   420
CCGATAGAAACAGTTTCGGTCAAGCTTAAACCAGGGATGGATGGTCCAAAGGTCAAGCAG    480
TGGCCGCTAACGGAAGAGAAGATTAAGGCGCTCGTAGAGATTTGTACTGAAATGGAGAAG    540
GAAGGCAAGATAAGCAAGATCGGGCCAGAGAACCCGTACAATACACCGGTATTTGCAATA    600
AAGAAGAAGGATTCAACAAAATGGCGAAAGCTTGTAGATTTTAGGGAACTAAACAAGCGA    660
ACCCAAGACTTTTGGGAAGTCCAACTAGGTATCCCACATCCAGCCGGTCTAAAGAAGAAG    720
AAATCGGTCACAGTCCTGGATGTAGGAGACGCATATTTTAGTGTACCGCTTGATGAGGAC    780
TTCCGAAAGTATACTGCGTTTACTATACCGAGCATAAACAATGAAACGCCAGGCATTCGC    840
TATCAGTACAACGTGCTCCCGCAGGGCTGGAAGGGGTCTCCGGCGATATTTCAGAGCTCT    900
ATGACAAAAATACTTGAACCATTCCGAAAGCAGAATCCGGATATTGTAATTTACCAATAC    960
ATGGACGATCTCTATGTGGGCTCGGATCTAGAAATTGGGCAGCATCGCACTAAGATTGAG   1020
GAACTGAGGCAACATCTGCTTCGATGGGGCCTCACTACTCCCGACAAGAAGCACCAGAAG   1080
GAGCCGCCGTTCCTAAAGATGGGCTACGAGCTTCATCCGGACAAGTGGACAGTACAGCCG   1140
ATAGTGCTGCCCGAAAAGGATTCTTGGACCGTAAATGATATTCAGAAACTAGTCGGCAAG   1200
CTTAACTGGGCCTCTCAGATTTACCCAGGCATTAAGGTCCGACAGCTTTGCAAGCTACTG   1260
AGGGGAACTAAGGCTCTAACAGAGGTCATCCCATTAACGGAGGAAGCAGAGCTTGAGCTG   1320
GCAGAGAATCGCGAAATTCTTAAGGAGCCGGGTGCACAGGGTATACTACGACCCCTCCAA   1380
GACCTTATAGCCGAGATCCAGAAGCAGGGCAGGGCCAATGGACGTACCAGATATATCAA   1440
GAACCGTTTAAGAATCTGAAGACTGGGAAGTACGCGCGCAAACGAGGGGCTCATACTAAT   1500
GATGTAAAGCAACTTACGGAAGCAGTACAAAAGATTACTACTGAGTCTATTGTGATATGG   1560
GGCAAGACCCCAAAGTTCAAGCTGCCCCATACAGAAGGAAACATGGGAAACATGGTGGAC   1620
GAATATTGGCAAGCTACCTGGATTCCAGAATGGGAATTTGTCAACACGCCGCCGCTGGTA   1680
AAACTGaggcctATGggtggcaagtggtcaaaaagtagtgtggttggatggcctactgta   1740
agggaaagaatgagacgagctgagccagcagcagatggggtgggagcagcatctcgagac   1800
ctggaaaaacatggagcaatcacaagtagcaatacagcagctaccaatgctgcttgtgcc   1860
tggctagaagcacaagaggaggaggaggtgggttttccagtcacacctcaggtacctta   1920
agaccaatgacttacaaggcagctgtagatcttagccactttttaaaagaaaaggggggga   1980
ctggaagggctaattcactcccaacgaagacaagatatccttgatctgtggatctaccac   2040
acacaaggctacttccctgattggcagaactacacaccagggccagggtcagatatcca   2100
ctgacctttggatggtgctacaagctagtaccagttgagccagataaggtagaagaggcc   2160
aataaaggagagaacaccagcttgttacaccctgtgagcctgcatggaatggatgaccct   2220
gagagagaagtgttagagtggaggtttgacagccgcctagcatttcatcacgtggccga   2280
gagctgcatccggagtacttcaagaactgctaa                              2213
[SEQ ID NO:16]

P17: sequence in bold
P51: sequence in capital letter
Nef: sequence in small letter
Boxes: nucleotides introduced by genetic construction
```

Amino-Acid Sequence (for F3)

```
                                                        [SEQ ID NO:17]
MGARASVLSGGELDRWEKIRLRPGGKKKYKLKHIVWASRELERFAVNPGLLETSEGCRQI    60

LGQLQPSLQTGSEELRSLYNTVATLYCVHQRIEIKDTKEALDKIEEEQNKSKKKAQQAAA   120

DTGHSNQVSQNY LDRT GPISPIETVSVKLKPGMDGPKVKQWPLTEEKIKALVEICTEMEK   180

EGKISKIGPENPYNTPVFAIKKKDSTKWRKLVDFRELNKRTQDFWEVQLGIPHPAGLKKK   240

KSVTVLDVGSAYFSVPLDEDFRKYTAFTIPSINNETPGIRYQYNVLPQGWKGSPAIFQSS   300

MTKILEPFRKQNPDIVIYQYMDDLYVGSDLEIGQHRTKIEELRQHLLRWGLTTPDKHQK   360

EPPFLKMGYELHPDKWTVQPIVLPEKDSWTVNDIQKLVGKLNWASQIYPGIKVRQLCKLL   420

RGTKALTEVIPLTEEAELELAENREILKEPVHGVYYDPSKDLIAEIQKQGQGQWTYQIYQ   480

EPFKNLKTGKYARMRGAHTNDVKQLTEAVQKITTESIVIWGKTPKFKLPIQKETWETWWT   540

EYWQATWIPEWEFVNTPPLVKL RP MGGKWSKSSVVGWPTVRERMRRAEPAADGVGAASRD   600

LEKHGAITSSNTAATNAACAWLEAQEEEEVGFPVTPQVPLRPMTYKAAVDLSHFLKEKGG   660
```

```
-continued
LEGLIHSQRRQDILDLWIYHTQGYFPDWQNYTPGPGVRYPLTFGWCYKLVPVEPDKVEEA    720

NKGENTSLLHPVSLHGMDDPEREVLEWRFDSPLAFHHVARELHPEYFKNC              770
```

P17 sequence: amino-acids 1-134 (in bold)
P51 sequence: amino-acids 137-562
Nef sequence: amino-acids 565-770
Boxes:amino-acids introduced by genetic construction
Methionine 494 replaced by Lysine (K) in F3 * construct K(Lysine)
K:instead of Tryptophan (W). Mutation introduced to remover enzyme activity.

F3 Expression in B834(DE3) Cells:

F3 expression level and recombinant protein solubility were evaluated, in parallel to F4 (p24-p66-Nef-p17) and p17-Nef (F2) production strains.

Induction condition: cells grown at 37° C./induced at 30° C. (+1 mM IPTG), during 3 h.

Breaking buffers: F4: 50 mM Tris/HCl pH: 8.0, 50 mM NaCl, 1 mM EDTA, +/−1 mM DTT F2: 50 mM Tris/HCl pH: 8.0, 50 mM NaCl, 1 mM EDTA, without DTT F3: 50 mM Tris/HCl pH: 7.5, 50 mM NaCl, 1 mM EDTA, +/−1 mM DTT Western blot analysis:

reagents rabbit polyclonal anti RT (rabbit PO3L16) (dilution: 1/10 000)

rabbit polyclonal anti Nef-Tat (rabbit 388) (dilution 1/10 000)

Alkaline phosphatase-conjugate anti-rabbit antibody (dilution: 1/7500)

"Fresh" Cellular Extracts

Figure 9:
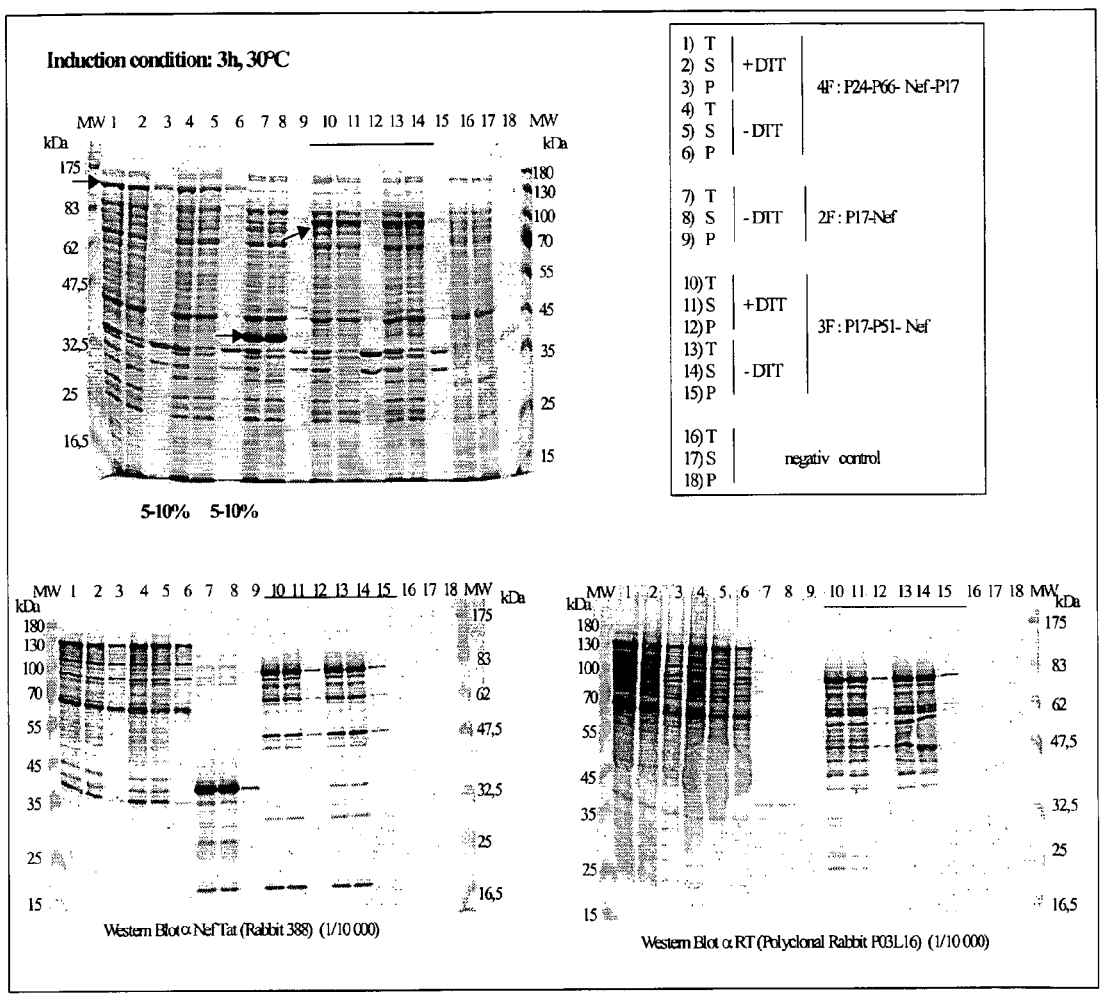
FIG. 9 is images of a Coomassie stained gel (upper panel) and western blots (lower panels) showing expression of F3 fusion proteins.

Cellular fractions corresponding to crude extracts (T), insoluble pellet (P) and supernatant (S) were analyzed on 10% reducing SDS-PAGE. As illustrated in FIG. 9, the F3 fusion protein is expressed at a high level (10% total protein). Almost all F3 is recovered in the soluble fraction (S) of cellular extracts, although 5-10% of F4 product are already associated with the pellet fraction. The WB pattern is simplified compared to F4.

Figure 10:
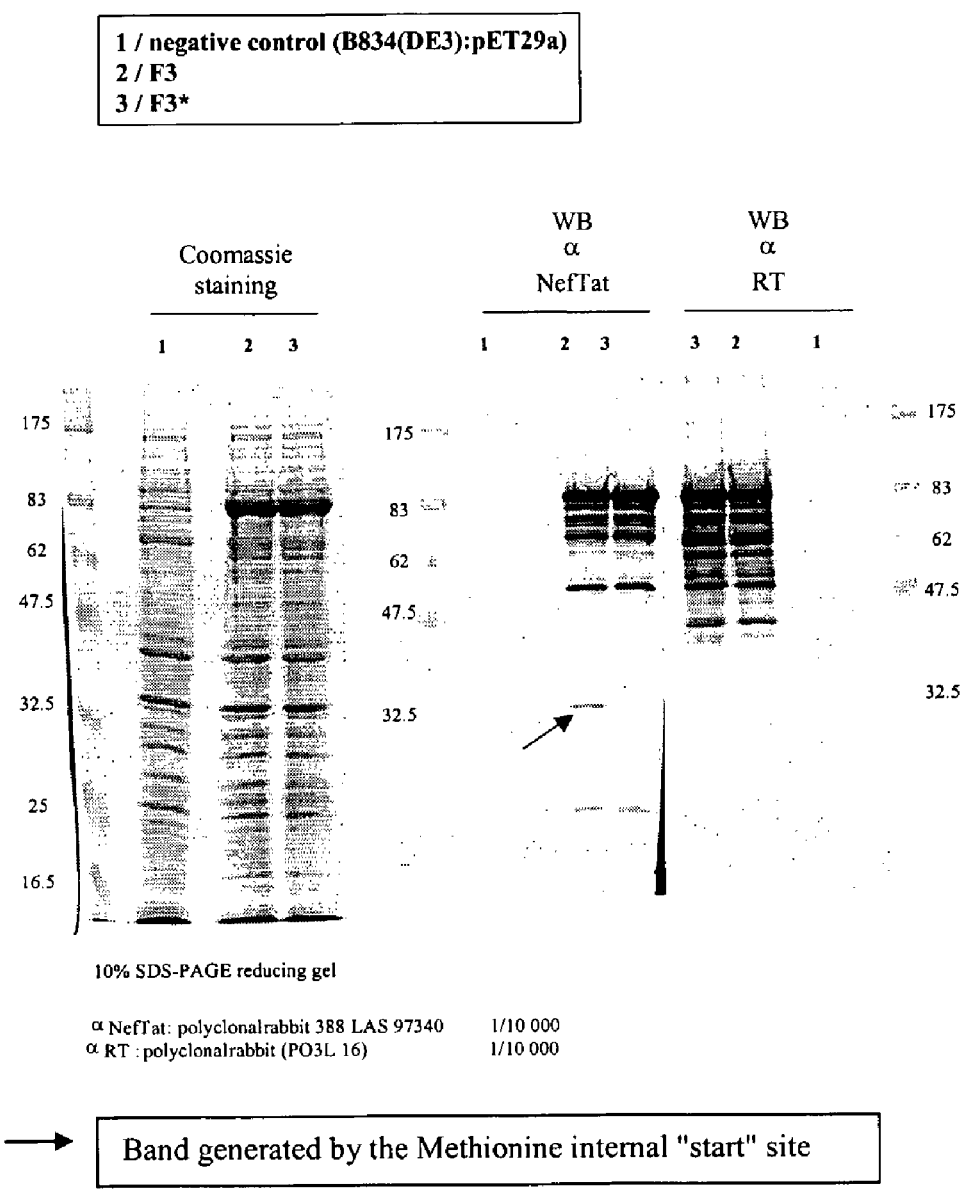
FIG. 10 is images of a Coomassie stained gel (left panel) and western blot (right panel) showing expression of F3* fusion proteins.

F3* Expression in B834(DE3) Cells:

F3* recombinant strain was induced at 37° C. over 3 h, in parallel to F3 non-mutated constructed. Crude cellular extracts were prepared and analyzed by Coomassie stained gel and Western blotting. As illustrated in FIG. 10, the F3* fusion protein is expressed at a very high level (10-20% total protein). There was a simplified WB pattern compared to F3; a very faint band at +/−32 kDa (detected on WB only) had disappeared.

Example 6

Construction and Expression of F4(p51) and F4(p51)*

RT/p51 was used in the F4 fusion construct (in place of RT/p66).

F4(p51)=p24-p51-Nef-p17

F4(p51)*=p24-p51*-Nef-p17—Mutated F4(p51): putative internal Methionine initiation site (present in RT portion) replaced by Lysine, to further simplify the antigen pattern.

Recombinant Plasmids Construction:

F4(p51): The sequence encoding p51 was amplified by PCR from pET29a/p51 expression plasmid. Restriction sites were incorporated into the PCR primers (NdeI and StuI at the 5' end. AvrII at the 3' end of the coding sequence). The PCR product was cloned into pGem-T intermediate plasmid and sequenced. pGem-T/p51 intermediate plasmid was restricted by NdeI and AvrII and the p51 fragment was ligated into pET28b/p24-RT/p66-Nef-p17 expression plasmid restricted by NdeI and NheI (resulting in the excision of RT/p66 sequence). Ligation was performed by combining digestion reactions in appropriate concentrations, in the presence of T4 DNA ligase. Ligation product was used to transform DH5α E. coli cells. Verification of insertion of p51 into the correct translational reading frame (in place of RT/p66 in the f4 fusion) was confirmed by DNA sequencing. The resulting fusion construct p24-RT/p51-Nef-p17 is named F4(p51).

F4(p51)*: Mutation of the putative internal methionine initiation site (present in RT/p51) was achieved with "GeneTailor Site-Directed Mutagenesis system" (Invitrogen), generating F4(p51)* construct.

F4(p51) and F4(p51)* expression plasmids were used to transform B834(DE3) cells.

Recombinant Proteins Characteristics:

N-term |p24:232a.a.| - |hinge:4a.a.| - |p51/51*:426a.a.| - |hinge:3a.a.| -
|Nef:206a.a.| - |hinge:2a.a.| - |p17:132a.a.| - C-term Length, Molecular Weight, Isoelectric Point (IP):
1005 AA, 114.5 kDa, IP: 8.47

Nucleotide Sequence (for F4(p51)*)

```
Atggttatcgtgcagaacatccaggggcaaatggtacatcaggccatatcacctagaact    60
Ttaaatgcatgggtaaaagtagtagaagagaaggctttcagcccagaagtaatacccatg   120
Ttttcagcattatcagaaggagccaccccacaagatttaaacaccatgctaaacacagtg   180
Gggggacatcaagcagccatgcaaatgttaaaagagaccatcaatgaggaagctgcagaa   240
Tgggatagagtacatccagtgcatgcagggcctattgcaccaggccagatgagagaacca   300
Aggggaagtgacatagcaggaactactagtacccttcaggaacaaataggatggatgaca   360
Aataatccacctatcccagtaggagaaatttataaaagatggataatcctgggattaaat   420
Aaaatagtaagaatgtatagccctaccagcattctggacataagacaaggaccaaaagaa   480
Cctttagagactatgtagaccggttctataaaactctaagagccgagcaagcttcacag   540
Gaggtaaaaaattggatgacagaaaccttgttggtccaaaatgcgaacccagattgtaag   600
Actattttaaaagcattgggaccagcggctacactagaagaaatgatgacagcatgtcag   660
Ggagtaggaggacccggccataaggcaagagttttg CATATGaggcct GGTCCGATCTCT    720
CCGATAGAAACAGTTTCGGTCAAGCTTAAACCAGGGATGGATGGTCCAAAGGTCAAGCAG    780
TGGCCGCTAACGGAAGAGAAGATTAAGGCGCTCGTAGAGATTTGTACTGAAATGGAGAAG    840
GAAGGCAAGATAAGCAAGATCGGGCCAGAGAACCCGTACAATACACCGGTATTTGCAATA    900
AAGAAGAAGGATTCAACAAAATGGCGAAACGTTGTAGATTTTAGGGAGACTAAACAAGCGA   960
ACCCAAGACTTTTGGGAAGTCCAACTAGGTATCCCACATCCAGCCGGTCTAAAGAAGAAG   1020
AAATCGGTCACAGTCCTGGATGTAGGAGACGCATATTTTAGTGTACCGCTTGATGAGGAC   1080
TTCCGAAAGTATACTGCGTTTACTATACCGAGCATAAACAATGAAACGCCAGGCATTCGC   1140
TATCAGTACAACGTGCTCCCGCAGGGCTGGAAGGGGTCTCCGGCGATATTTCAGAGCTCT   1200
ATGACAAAAATACTTGAACCATTCCGAAAGCAGAATCCGGATATTGTAATTTACCAATAC   1260
ATGGACGATCTCTATGTGGGCTCGGATCTAGAAATTGGGCAGCATGCGCTAAGATTGAG   1320
GAACTGAGGCAACATCTGCTTCGATGGGGCCTCACTACTCCCGACAAGAAGCACCAGAAG   1380
GAGCCGCCGTTCCTAAAGATGGGCTACGAGCTTCATCCGGACAAGTGGACAGTACAGCCG   1440
ATAGTGCTGCCCGAAAAGGATTCTTGGACCGTAAATGATATTCAGAAACTAGTCGGCAAG   1500
Ggactggaagggctaattcactcccaacgaagacaagatatccttgatctgtggatctac   2340
Cacacacaaggctacttccctgattggcagaactacacaccagggccaggggtcagatat   2400
Ccactgacctttggatggtgctacaagctagtaccagttgagccagataaggtagaagag   2460
Gccaataaaggagagaacaccagcttgttacaccctgtgagccatgcatgaatggatgac   2520
Cctgagagagaagtgttagagtggaggtttgacagccgcctagcatttcatcacgtggcc   2580
CgagagctgcatccggagtacttcaagaactgcAGGCCTATGGGTGCGAGAGCGTCAGTA   2640
TTAAGCGGGGGAGAATTAGATCGATGGGAAAAATTCGGTTAAGGCCAGGGGGAAAGAAA   2700
AAATATAAATTAAAACATATAGTATGGGCAAGCAGGGAGCTAGAACGATTCGCAGTTAAT   2760
CCTGGCCTGTTAGAAACATCAGAAGGCTGTAGACAAATACTGGGACAGCTACAACCATCC   2820
CTTCAGACAGGATCAGAAGAACTTAGATCATTATATAATAACAGTAGCAACCCTCTATTGT   2880
GTGCATCAAAGGATAGAAGAACTTAGATCATTA TATAAT ACAGTAGCAACCCTCTATTGT   2880
GTGCATCAAAGGATAGAGATAAAAGACACCAAGGAAGCTTTAGACAAGATAGAGGAAGAG   2940
CAAAACAAAAGTAAGAAAAACGACAGCAAGCAGCAGCTGACACAGGAAAACAGCAATCAG   3000
GTCAGCCAAAATTACtaa                                            3018
[SEQ ID NO:18]
```
P24: sequence in bold
P51: sequence in capital letter
Nef: sequence in small letter
P17: sequence underlined
Boxes: nucleotides introduced by genetic construction Amino-Acid Sequence (for F4(p51)*)

```
MVIVQNIQGQMVHQAISPRTLNAWVKVVEEKAFSPEVIPMFSALSEGATPQDLNTMLNTV     60
GGHQAAMQMLKETINEEAAEWDRVHPVHAGPIAPGQMREPRGSDIAGTTSTLQEQIGWMT    120
NNPPIPVGEIYKRWIILGLNKIVRMYSPTSILDIRQGPKEPFRDYVDRFYKTLRAEQASQ    180
EVKNWMTETLLVQNANPDCKTILKALGPAATLEEMMTACQGVGGPGHKARVL HMRE GPIS    240
PIETVSVKLKPGMDGPKVKQWPLTEEKIKALVEICTEMEKEGKISKIGPENPYNTPVFAI    300
KKKDSTKWRKLVDFRELNKRTQDFWEVQLGIPHPAGLKKKKSVTVLDVGDAYFSVPLDED    360
FRKYTAFTIPSINNETPGIRYQYNVLPQGWKGSPAIFQSSMTKILEPFRKQNPDIVIYQY    420
MDDLYVGSDLEIGQHRTKIEELRQHLLRWGLTTPDKKHQKEPPFLKMGYELHPDKWTVQP    480
IVLPEKDSWTVNDIQKLVGKLNWASQIYPGIKVRQLCKLLRGTKALTEVIPLTEEAELEL    540
AENREILKEPVHGVYYDPSKDLIAEIQKQGQGQWTYQIYQEPFKNLKTGKYARKRGAHTN    600
DVKQLTEAVQKITTESIVIWGKTPKFKLPIQKETWETWWTEYWQATWIPEWEFVNTPPLV    660
KL ALA MGGKWSKSSVVGWPTVRERMRRAEPAADGVGAASRDLEKHGAITSSNTAATNAAC    720
AWLEAQEEEEVGFPVTPQVPLRPMTYKAAVDLSHFLKEKGGLEGLIHSQRRQDILDLWIY    780
HTQGYFPDWQNYTPGPGVRYPLTFGWCYKLVPVEPDKVEEANKGENTSLLHPVSLHGMDD    840
PEREVLEWRFDSRLAFHHVARELHPEYFKNC EH MGARASVLSGGELDRWEKIRLRPGGKK    900
KYKLKHIVWASRELERFAVNPGLLETSEGCRQILGQLQPSLQTGSEELRSLYNTVATLYC    960
VHQRIEIKDTKEALDKIEEEQNKSKKKAQQAAADTGHSNQVSQNY                 1005
[SEQ ID NO:19]
```
P24: amino-acids 1-232
P51: amino-acids 237-662
Nef: amino-acids 666-871
P17: amino-acids 874-1005
K (Lysine): instead of Methionine (internal "start" codon)
K (Lysine) K: instead of Tryptophan (W). Mutation introduced to remove enzyme activity.

F4(p51) Expression in B834(DE3) Cells:

F4(p51) expression level and recombinant protein solubility were evaluated, in parallel to F4 expressing strain.

Induction condition: cells grown at 37° C./induced at 22° C. (+1 mM IPTG), over 19 h.

Breaking buffer: 50 mM Tris/HCl pH: 7.5, 1 mM EDTA, 1 mM DTT

Western blot analysis:
reagents
—rabbit polyclonal anti RT (rabbit PO3L16) (dilution: 1/10 000)
—rabbit polyclonal anti Nef-Tat (rabbit 388) (dilution 1/10 000)
—Alkaline phosphatase-conjugate anti-rabbit antibody (dilution: 1/7500)

Cellular fractions corresponding to crude extracts (T), insoluble pellet (P) and supernatant (S) were analyzed on 10% reducing SDS-PAGE.

As illustrated in FIG. 11, F4(p51) was expressed at a high level (10% of total protein), similar to F4. Almost all F4(p51) is recovered in the soluble fraction (S) of cellular extracts. Upon detection with an anti-Nef-tat reagent, F4(p51) the WB pattern was shown to be simplified (reduction of truncated products below +/−60 kDa).

Figure 12:
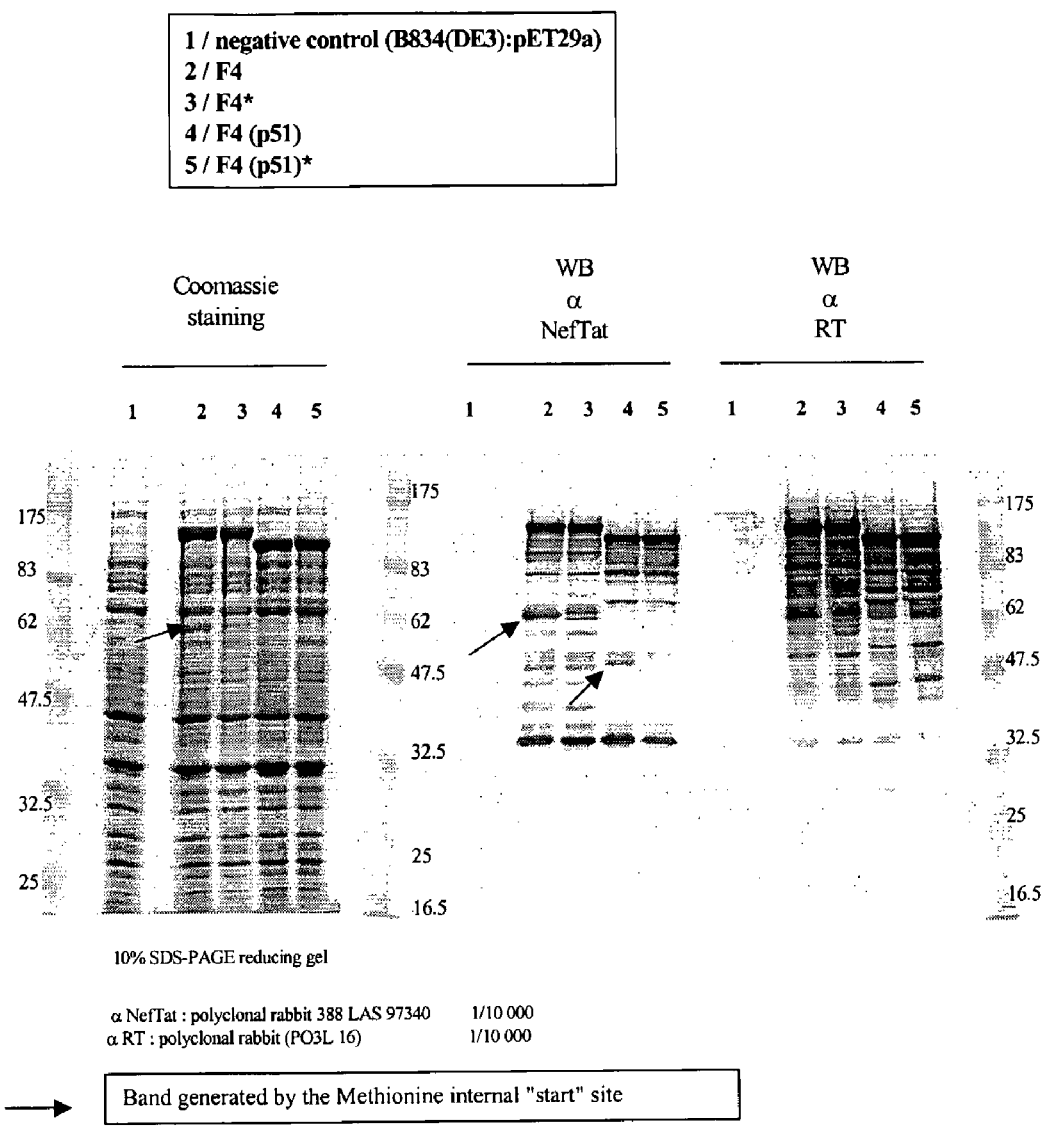
FIG. 12 is images of a Coomassie stained gel (left panel) and western blots (two right panels) showing expression of F4(p51) and F4(p51)* fusion proteins.

F4(p51)* Expression in B834(DE3) Cells:

F4(p51)* recombinant strain was induced at 22° C. over 18 h, in parallel to F4(p51) non-mutated construct, F4 and F4*. Crude cellular extracts were prepared and analyzed by Coomassie stained gel and Western blotting. As illustrated in FIG. 12 high expression of F4(p51) and F4(p51)* fusions was observed, representing at least 10% of total protein. WB pattern: reduction of truncated products below +/−60 kDa. In addition, for F4(p51)* construct, the 47 kDa band (due to internal start site) has disappeared.

Example 7

Purification of F4, F4(p51)* and F4*—Purification Method I

The fusion protein F4, comprising the 4 HIV antigens p24-RT-Nef-p17, was purified from a $E.$ $coli$ cell homogenate according to purification method I, which comprises the following principal steps:
Ammonium sulfate precipitation of F4
SO3 Fractogel cation-exchange chromatography (positive mode)
Octyl sepharose hydrophobic interaction chromatography (positive mode)
Q sepharose FF anion-exchange chromatography (positive mode)
Superdex 200 gel filtration chromatography in presence of SDS
Dialysis and concentration Additionally, the F4(p51)* fusion protein (RT replaced by the codon optimized p51 carrying an additional mutation Met592Lys) and the F4* protein (F4 carrying an additional Met592Lys mutation) were purified using the same purification method I.

Protein Quantification
Total protein was determined using the Lowry assay. Before measuring the protein concentration all samples are dialyzed overnight against PBS, 0.1% SDS to remove interfering substances (urea, DTT). BSA (Pierce) was used as the standard.

SDS-PAGE and Western Blot
Samples were prepared in reducing or non-reducing SDS-PAGE sample buffer (+/−β-mercaptoethanol) and heated for 5 min at 95° C.
Proteins were separated on 4-20% SDS-polyacrylamide gels at 200 V for 75 min using pre-cast Novex Tris-glycine gels or Criterion gels (Bio-Rad), 1 mm thick.
Proteins were visualized with Coomassie-blue R250.
For the western blots (WB), the proteins were transferred from the SDS-gel onto nitrocellulose membranes (Bio-Rad) at 4° C. for 1.5 h at 100 V or overnight at 30 V.
F4 was detected using monoclonal antibodies against the different antigens, anti-p24, anti-Nef-Tat, anti-RT (sometimes a mixture of anti-p24 and anti Nef-Tat was used to detect a maximum number of protein bands).
Alkaline-phosphatase conjugated anti-mouse or anti-rabbit antibodies were bound to the primary antibodies and protein bands were visualized using BCIP and NBT as the substrates.

Anti-$E.$ $coli$ Western Blot
5 µg protein (Lowry) were separated by SDS-PAGE and transferred onto nitrocellulose membranes as above.
Residual host cell proteins were detected using polyclonal anti-$E.$ $coli$ antibodies. Protein bands were visualized with the alkaline-phosphatase reaction as above.

Purification Method I
Method I comprises a precipitation by ammonium sulfate and four chromatographic steps:
$E.$ $coli$ cells were homogenized in 50 mM Tris buffer at pH 8.0 in the presence of 10 mM DTT, 1 mM PMSF, 1 mM EDTA at OD50 (~360 ml). 2 Rannie passages were applied at 1000 bars.
Cells debris and insoluble material were removed by centrifugation at 14400×g for 20 min.
Ammonium sulfate (AS) was added from a 3.8M stock solution to the clarified supernatant to a final concentration of 1.2M. Proteins were precipitated for 2 hours at room temperature (RT) and then pelleted by centrifugation (10 min at 14400×g). The pellet was resuspended in 8M urea, 10 mM DTT in 10 mM phosphate buffer at pH 7.0.
The antigen was captured on a SO3 Fractogel column (Merck) in the presence of 8M urea and 10 mM DTT at pH 7.0 in phosphate buffer. The column was washed to elute non-bound protein followed by a pre-elution step with 170 mM NaCl to remove bound host cell proteins (HCP). F4 was then eluted with 460 mM NaCl, 8M urea, 10 mM DTT in phosphate buffer at pH 7.0.
The SO3 eluate was 2 fold diluted with 10 mM phosphate buffer, pH 7, and loaded onto a Octyl sepharose column (Amersham Biosciences) in the presence of 4M urea, 1 mM DTT, 230 mM NaCl in phosphate buffer at pH 7.0. Following a washing step (equilibration buffer) bound F4 was eluted with 8M urea, 1 mM DTT in 25 mM Tris buffer at pH 8.0.
The Octyl eluate was diluted and adjusted to pH 9.0 and F4 was then bound to an Q sepharose column (Amersham Bioscience) in the presence of 8M urea at pH 9.0 (25 mM Tris). Unbound protein was washed off (8M urea, 25 mM Tris at pH 9.0) and a pre-elution step (90 mM NaCl in 8M urea, 25 mM Tris, pH 9.0) removed HCP and F4-degradation products. F4 was desorped from the column with 200 mM NaCl, 8M urea in Tris buffer at pH 9.0.
An aliquot of the Q eluate was spiked with 1% SDS and dialyzed against PBS buffer containing 0.1% SDS and 1 mM DTT to remove the urea prior to injecting the sample onto the gel filtration column (prep grade Superdex 200, two 16×60 cm columns connected in a row). The relevant fractions were pooled after in-process SDS-PAGE analysis.
Samples were dialyzed twice at RT in dialysis membranes (12-14 kDa cut-off) overnight against 1 10.5M Arginine, 10 mM Tris, 5 mM Glutathione, pH 8.5.

The sequential purification steps are shown in the flowchart below.

Purification Flowsheet

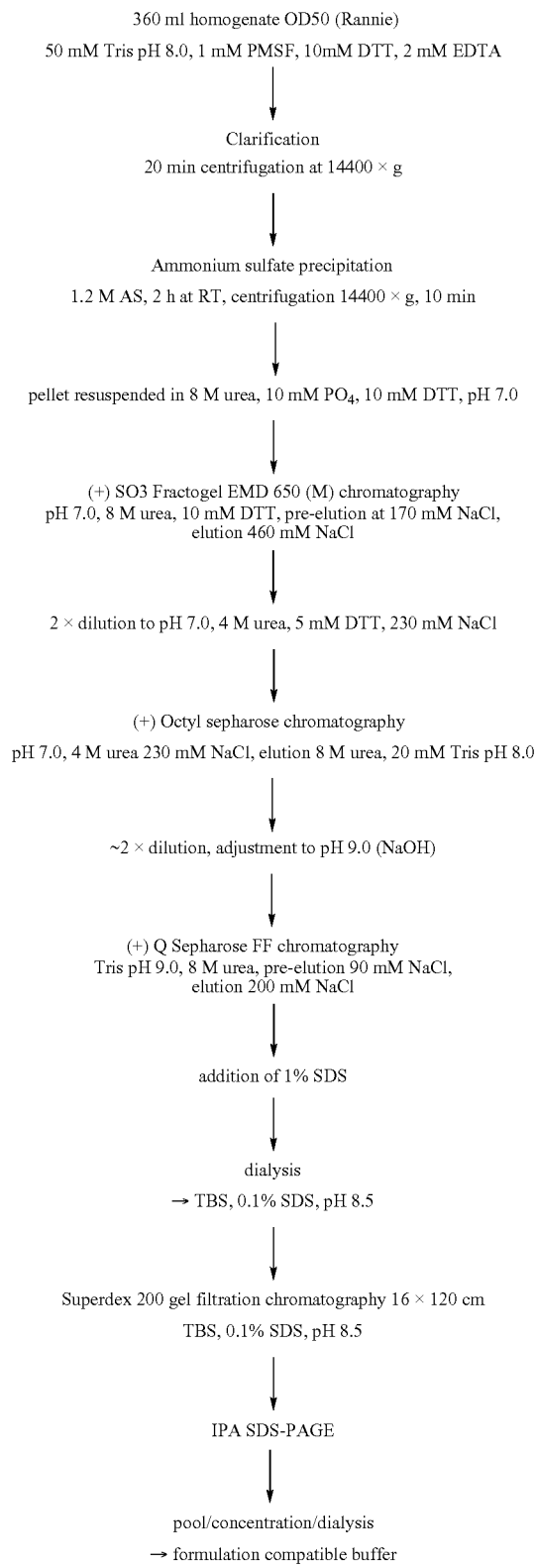

IPA—In Process Analysis

All buffers contain 1 mM DTT if not otherwise specified.

Results Purification of F4

SDS-PAGE/Western Blot Follow-Up of the Purification Process

Figure 13:
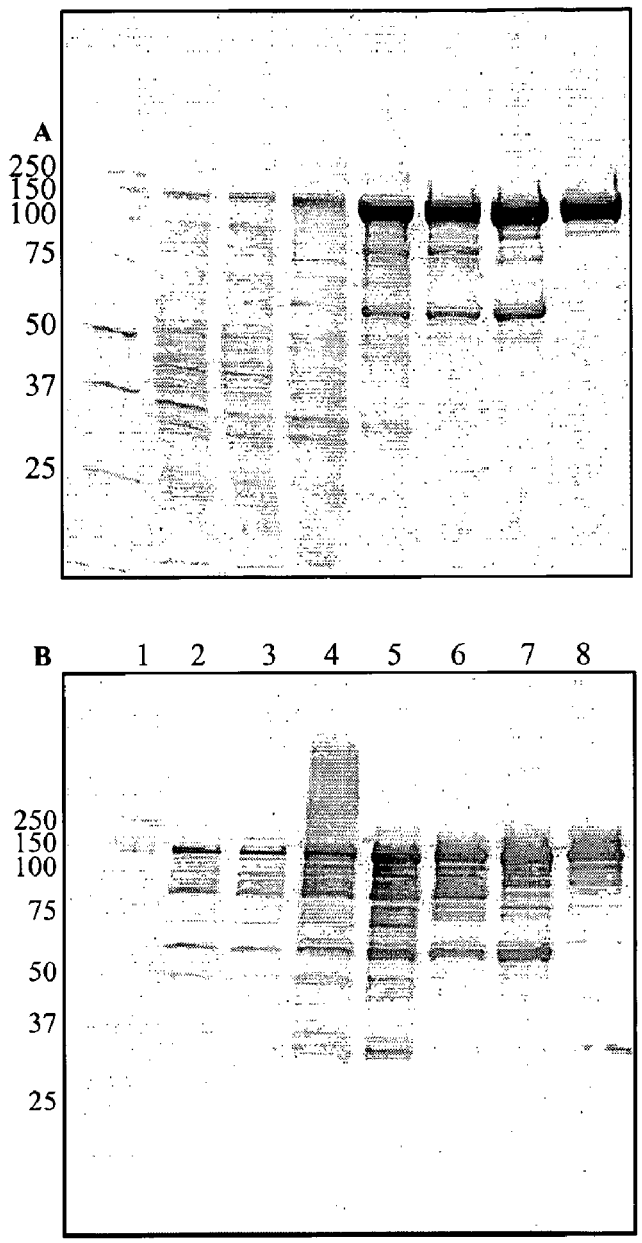
FIGS. 13A and B are images of a Coomassie stained gel (A) and western blot (B) showing purification of F4 fusion protein.

FIG. 13 shows the SDS gel and the anti-p24/anti-Nef-Tat western blot of the F4-containing fractions collected during the purification of F4.

The *E. coli* homogenate is shown in FIG. 13, lane 2, with F4 estimated to represent about 10% of the total proteins (density scans of Coomassie blue stained SDS-gels). After centrifugation, the soluble fraction of F4 was recovered in the clarified supernatant (lane 3). The ammonium sulfate precipitation step eliminated many impurities (lane 4) and reduced the proteic charge for the subsequent chromatographic step. Additionally, the 8M urea used to resuspend the precipitate dissociated complexes of F4 with HCP and allowed both complete capture of F4 by and quantitative elution from the SO3 resin. The SO3 eluate shown in lane 5 was considerably enriched in F4 but the heterogeneous pattern remained principally unchanged. The hydrophobic Octyl sepharose column mainly removed low molecular weight (LMW) HCP and F4-degradation products (lane 6), thereby simplifying the F4 pattern. The Q sepharose chromatography further simplified the F4 pattern and removed many impurities (lane 7). Final purity in terms of *E. coli* impurities was obtained after this step. In fact, no host cell proteins were detected in the Q eluate by anti-*E. coli* western blot analysis. The purified F4 thus produced is referred to as F4Q. The Superdex 200 column separated LMW F4-degradation products from the full length F4 improving F4 homogeneity in the Superdex 200 eluate (lane 8). The term F4S may be used to refer to F4 purified according to the full scheme of method I.

An anti-*E. coli* western blot was done of the same fractions collected during the purification of F4. The absence of visible bands on the anti-*E. coli* western blot indicated HCP contamination below 1% in the Q eluate and in the Superdex eluate.

F4 and Protein Recovery

F4 recovery at each step of the purification process was estimated from SDS-PAGE and western blot analysis. To estimate F4 recovery from SDS-gels, the sample volumes loaded onto the SDS-gels corresponded to the volumes of the different fractions collected during the purification.

Table 1 displays the protein recovery in the F4-containing fractions.

Table 1: Protein recovery in the F4-positive fractions collected during the purification process (360 ml homogenate). The protein concentration was determined with the Lowry assay.

TABLE 1

Protein recovery in the F4-positive fractions collected during the purification process (360 ml homogenate). The protein concentration was determined with the Lowry assay.

| Purification Step | Protein (mg) | Step Recovery (%) | Cum. Recovery (%) |
|---|---|---|---|
| homogenate | 6500 | 100 | 100 |
| clarified homogenate | 4641 | 71 | 71 |
| resuspended AS precipitate | 728 | 16 | 11 |
| SO3 eluate | 247 | 34 | 3.8 |
| Octyl sepharose eluate | 129 | 52 | 2.0 |
| Q sepharose eluate | 74 | 57 | 1.1 |
| Superdex 200 | 36 | 49 | 0.6 |

The table shows the amount of protein in the homogenate and the soluble material, including F4, recovered in the supernatant after the clarification step. The AS-precipitation step removed a great amount of HCP and only a slight loss of F4 was observed on the SDS-gel. The SO3 chromatography additionally removed many impurities and the SDS-gel indicated a high recovery of F4. In contrast, the ~50% protein recovery measured with both the Octyl sepharose and the Q sepharose columns were also accompanied by losses of F4. Protein recovery after the gel filtration chromatography was about 50%. The SDS-gel shows that many LMW-protein bands (F4-degradation bands) were removed, concomitantly reducing F4 recovery.

F4 Yield

Table 1 above shows that about 36 mg purified F4 could be obtained from 360 ml homogenate at OD50. Therefore, 1 l homogenate at OD 50 should yield about 100 mg purified F4. Since ODs of 70-90 were achieved during the fermentation process, the yield per liter fermenter would accordingly be in the range of 140 to 180 mg F4.

Results Purification of F4(p51)*

The F4(p51)* fusion construct was purified using purification method I described above without modifications.

SDS-PAGE/Western Blot Follow-Up of the Purification Process

FIG. 14 shows the SDS gel and the anti-p24/anti-Nef-Tat western blot of the F4(p51)*-containing fractions collected during the purification of F4(p51)*.

The SDS-gel and the western blot demonstrate that the F4(p51)* fusion protein globally behaved similarly to F4 at the ammonium sulfate precipitation step as well as during the chromatographic steps. Purified F4(p51)* had a heterogeneity pattern similar to purified F4.

An anti E. coli western blot indicated that HCP contamination was below 1% in both the Q eluate and the Superdex eluate.

Yield

About 25% of F4(p51)* were lost in the insoluble fraction of the homogenate. Additionally, because the purification method was not adapted to this protein, losses were observed at the chromatographic steps. Therefore the overall recovery of F4(p51)* was reduced to about 25 mg per liter homogenate (OD50). Extrapolated to 1 liter culture at OD 177, the yield would accordingly be in the range of 85 mg F4(p51)*.

Results Purification of F4*

The F4* fusion construct was purified using purification method I described above without modifications.

SDS-PAGE/Western Blot Follow-Up of the Purification Process

Figure 15:
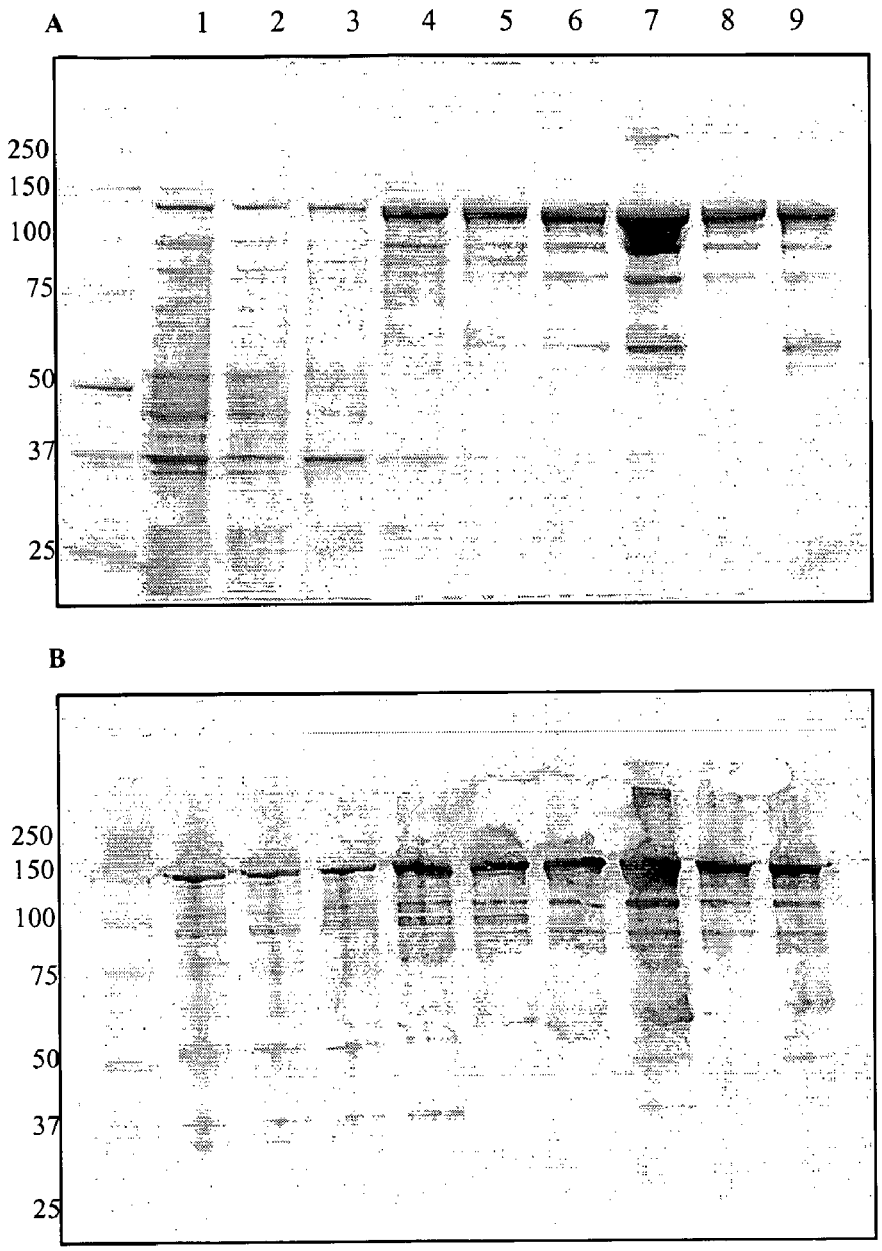
FIGS. 15A and B are images of a Coomassie stained gel (A) and western blot (B) showing purification of F4 fusion protein.

FIG. 15 shows the SDS gel and the anti-p24/anti-Nef-Tat western blot of the F4*-containing fractions collected during the purification of F4*.

As with F4(p51)* it can also be noted that F4* globally behaved quite similarly to F4 during the purification procedure. The protein was recovered in the expected fractions as shown by the SDS-gel and the western blot. An anti-E. coli western blot also demonstrated elimination of most HCP already after the Q sepharose column.

Yield

The global recovery was about 17 mg purified F4* obtained from 465 ml homogenate OD50. Extrapolated to 1 l culture at OD 140, the yield would accordingly be in the range of 100 mg F4*.

Figure 16:
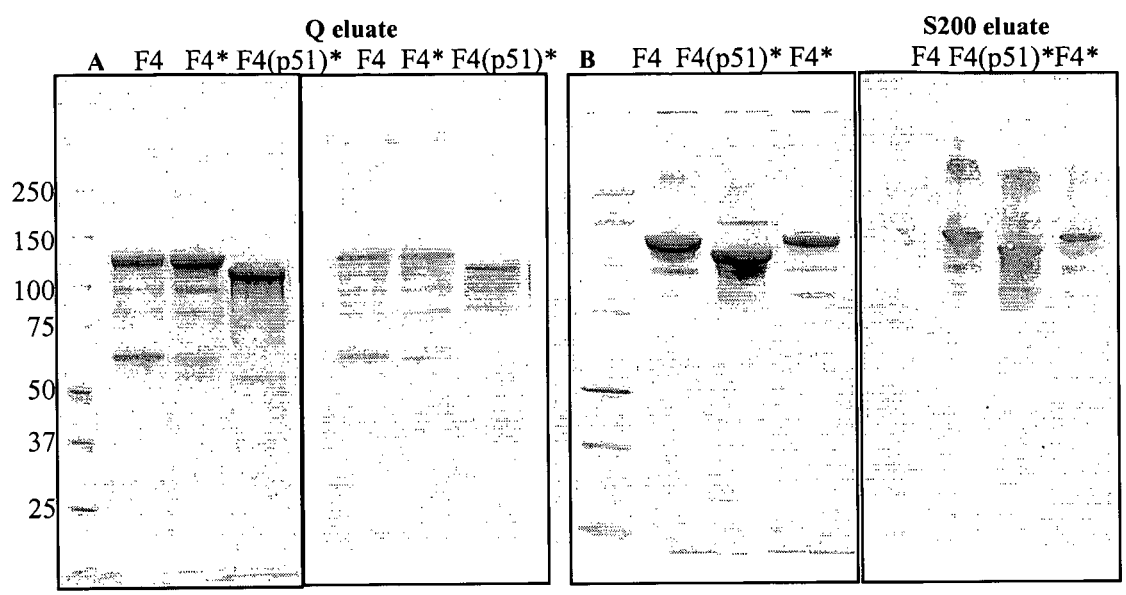
FIGS. 16A and B are images of a Coomassie stained gel (A) and western blot (B) showing a comparison of purity between F4, F4* and F4(p51)* fusion proteins.

In summary, the three fusion proteins F4, F4(p51)* and F4* were purified employing purification method I. The SDS gel in FIG. 16 compares the three purified proteins showing the different level of heterogeneity of the constructs after the Q sepharose step and after elimination of LMW bands by the Superdex 200 column.

Example 8

Purification of F4 and F4co (Codon Optimized)—Purification Method II

Purification Method II

A simplified purification procedure, method II as compared to method I, was also developed. Method II consists of only 2 chromatographic steps and a final dialysis/diafiltration for buffer exchange. Notably, a CM hyperz chromatographic column (BioSepra) was introduced to replace the clarification step, the ammonium sulfate precipitation and the SO3 chromatography of method I (Example 7). Method II was used to purify both F4 and full-codon optimized F4 ("F4co"). For F4co, two different forms of method II were performed, one involving carboxyamidation and one not. The purpose of the carboxyamidation step was to prevent oxidative aggregation of the protein. This carboxyamidation is performed after the $1^{st}$ chromatographic step (CM hyperZ).

E. coli cells (expressing F4 or F4co) were homogenized in 50 mM Tris buffer at pH 8.0 in the presence of 10 mM DTT, at OD90. 2 Rannie passages were applied at 1000 bars.

8M urea were added to the homogenate before application to the CM hyperZ resin (BioSepra) equilibrated with 8M urea in phosphate buffer at pH 7. Antigen capture was done in a batch mode. The resin was then packed in a column, unbound proteins were washed off with the equilibration buffer and bound host cell proteins (HCP) were removed by a pre-elution step with 120 mM NaCl. F4co was then eluted with 360 mM NaCl, 8M urea, 10 mM DTT in phosphate buffer at pH 7.0.

To control oxidative aggregation of the fusion protein, the cysteine groups of F4co can be carboxyamidated with idoacetamide. Therefore, optionally, 50 mM iodoacetamide was added to the CM hyperz eluate and carboxyamidation was done for 30 min at room temperature in the dark.

The CM hyperZ eluate was then adequately diluted (about 5-8 fold) and adjusted to pH 9.0. F4co or F4coca was then bound to a Q sepharose column (Amersham Bioscience) in the presence of 8M urea in Tris buffer at pH 9.0. Unbound protein was washed off with the equilibration buffer and a pre-elution step with 90 mM NaCl (only with non-carboxyamidated protein) in the same buffer removed bound HCP. F4co was desorped from the column with 200 mM NaCl, 8M urea in Tris buffer at pH 9.0.

Samples were dialyzed twice at RT in dialysis membranes (12-14 kDa cut-off) overnight against 1 l 0.5M Arginine, 10 mM Tris buffer, 10 mM Glutathione (only added to the non-carboxyamidated protein), pH 8.5. Alternatively, buffer exchange was accomplished by diafiltration against 10 sample volumes of the same buffer using a tangential-flow membrane with 30 or 50 kDa cut-off.

Finally, the dialyzed product was sterile filtered through a 0.22 μm membrane.

The sequential purification steps are shown in the flowchart below.

Purification Flowsheet

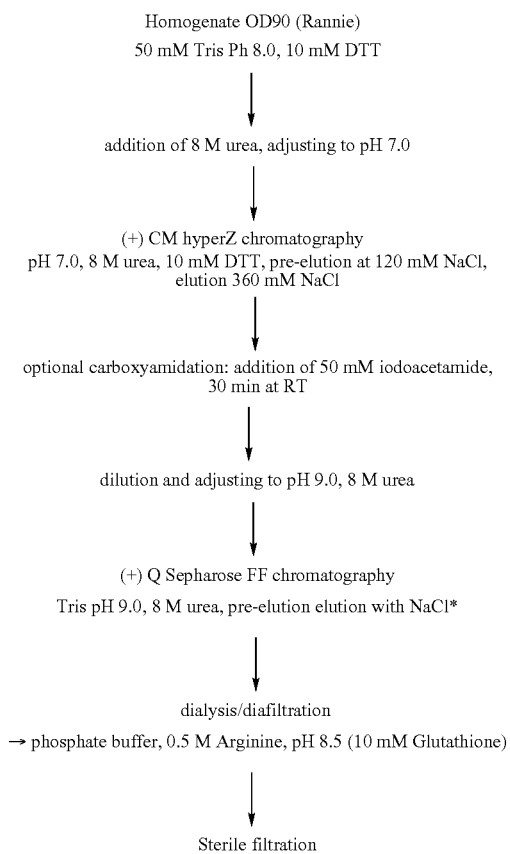

All buffers contained DTT if F4co was not carboxyamidated and Glutathione in the purified bulk. Reducing agents were omitted once the protein was carboxyamidated. *NaCl—for F4co this was 200 mM NaCl, for F4coca elution was by gradient of NaCl. This step can be further optimized for F4coca by pre-eluting with 60 mM NaCl and eluting with 100 mM NaC; and for F4co by eluting with 100 mM NaCl (no pre-elution step needed).

Results: Purification of F4co

Figure 17:
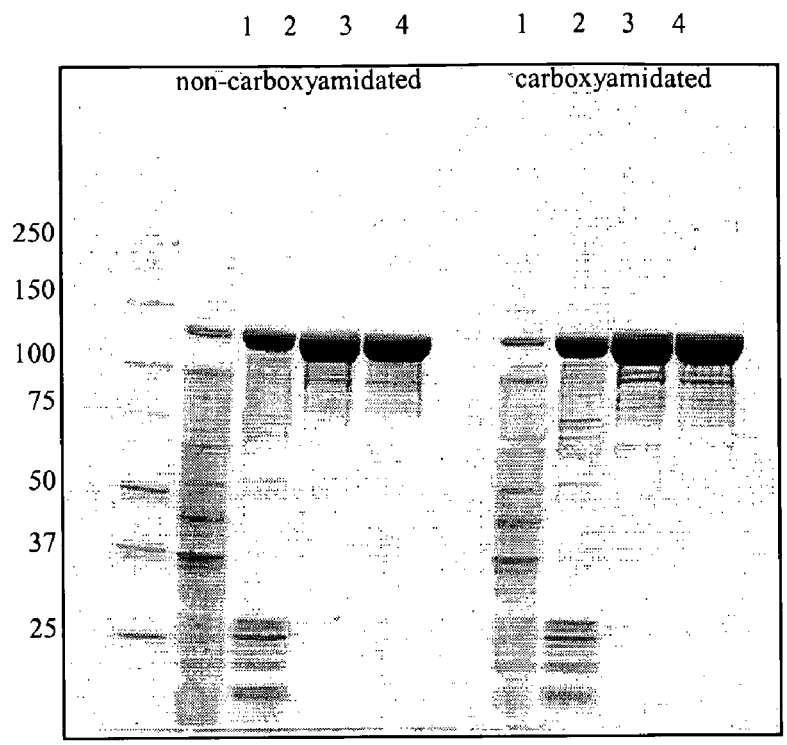
FIG. 17 is an image of a Coomassie stained gel following purification of F4co and carboxyamidated F4co.

FIG. 17 shows a SDS gel of the F4-containing fractions collected during the purification of F4co and the purification of carboxyamidated F4co ("F4coca").

The CM hyperZ resin completely captured F4co from the crude homogenate (lane 1) in the presence of 8M urea and quantitative elution was achieved with 360 mM NaCl. The CM hyperZ eluate shown in lane 2 was considerably enriched in F4co. After appropriate dilution and adjustment of the sample to pH 9, F4co or F4coca was bound to a Q sepharose column. F4co or F4coca was then specifically eluted with 200 mM NaCl as shown in lane 3. This chromatography not only removed remaining host cell proteins but also DNA and endotoxins. To bring the purified material in a formulation-compatible buffer, the Q sepharose eluate was dialyzed against 10 mM Tris buffer, 0.5M Arginine, 10 mM Glutathione pH 8.5 in a dialysis membrane with 12-14 kDa cut-off. Glutathione was omitted with the carboxyamidated protein.

Purification of both F4co and F4coca yielded about 500 mg purified material per L of culture OD130. This was in a similar range as observed before with the non-codon-optimized F4.

Figure 18:
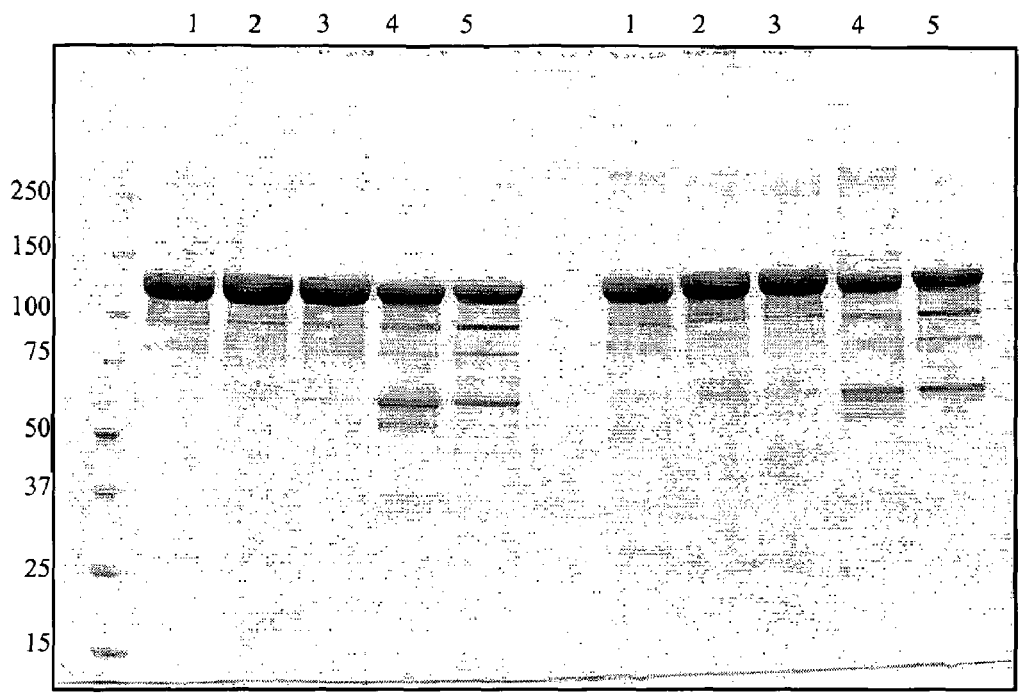
FIG. 18 is an image of a Coomassie stained gel following purification of F4, F4co and F4coca.

As described above, two different purification methods (I and II) have been developed to purify the different F4 constructs. FIG. 18 compares the different purified bulks that were obtained.

The SDS gel in FIG. 18 clearly illustrates the distinct pattern of the two different proteins, F4 and F4co. Whereas F4 presented several strong low molecular weight (LMW) bands, only faint bands were visible with the codon-optimized F4co. Method I and method II produce a very similar F4co pattern. Anti-*E. coli* western blot analysis confirmed the purity of the purified proteins indicating host cell protein contamination below 1% in all the preparations.

Example 9

Immunogenicity of F4 in Mice

Formulation:

Adjuvant Formulation 1B:

To prepare Adjuvant formulation 1 B, A mixture of lipid (such as phosphatidylcholine either from egg-yolk or synthetic) and cholesterol and 3 D-MPL in organic solvent, is dried down under vacuum (or alternatively under a stream of inert gas). An aqueous solution (such as phosphate buffered saline) is then added, and the vessel agitated until all the lipid is in suspension. This suspension is then microfluidised until the liposome size is reduced to about 100 nm, and then sterile filtered through a 0.2 μm filter. Extrusion or sonication could replace this step.

Typically the cholesterol:phosphatidylcholine ratio is 1:4 (w/w), and the aqueous solution is added to give a final cholesterol concentration of 5 to 50 mg/ml.

The liposomes have a defined size of 100 nm and are referred to as SUV (for small unilamelar vesicles). If this solution is repeatedly frozen and thawed the vesicles fuse to form large multilamellar structures (MLV) of size ranging from 500 nm to 15 μm.

The liposomes by themselves are stable over time and have no fusogenic capacity. QS21 in aqueous solution is added to the liposomes to reach a final 3 D-MPL and QS21 concentrations of 100 □g/ml.

Formulation 2A: 3 De acylated monophoshphoryl lipid A and QS21 in an oil in water emulsion;

Preparation of oil in water emulsion can be made by following the protocol as set forth in WO 95/17210. In detail the emulsion contains: 5% Squalene 5% tocopherol 2.0% tween 80; the particle size is 180 nm.

Preparation of Oil in Water Emulsion (2 Fold Concentrate)

Tween 80 is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S microfluidics machine. The resulting oil droplets have a size of approximately 180 nm.

Sterile bulk emulsion is added to PBS to reach a final concentration of 500 □l of emulsion per ml (v/v). 3 D-MPL is then added to reach a final concentration of 100 μg. QS21 is then added to reach a final concentration of 100 μg per ml. Between each addition of component, the intermediate product is stirred for 5 minutes F4Q not codon optimized, purified according to purification method I, was diluted in a phosphate/Arginine buffer pH 6.8. The dilution was mixed with two different concentrated adjuvants (adjuvants 2A and 1B) in order to obtain a final formulation of 40 μg/dose of 500 μl of F4 in presence of 290 (for adjuvant 2A)-300 (for adjuvant 1B) mM Argnine, 50 μg MPL and 50 μg QS21. 100 μl of each formulation were injected in mice.

Mouse immunogenicity studies were performed to evaluate the cellular and humoral immune responses to the four antigens found within F4 (p24, p17, RT and Nef).

Due to the complexity of the F4 antigen, eight strains of mice, each with a different genetic background, were immunised twice at day 0 and day 21 with 8 □g of adjuvanted F4 protein prepared as described above, in a 100 μl volume. Serum and spleen samples were collected 14 days following the last immunisation (day 35) for analysis of the humoral and cellular responses to each of the four components of F4 (p24, p17, RT and Nef), as well as F4.

Total antibody responses were characterised by ELISAs specific for p24, p17, RT, Nef and F4. The following table, Table 2, summarises where antigen specific humoral responses were observed in each strain. The results indicate the presence or absence of antibodies compared to control animals immunized with adjuant alone. The results presented are a compilation from two separate but identical experiments. In the table, 2A refers to antigen formulated with 3D-MPL and QS21 in an oil in water emulsion and 1B refers to antigen formulated with 3D-MPL, QS21 and cholesterol containing liposomes.

TABLE 2

| mouse strain | p17 | p24 | Nef | RT | F4 |
|---|---|---|---|---|---|
| CB6F1 | +/−<br>+2A −1B | + | + | + | + |
| Balb/c | −<br>+/−2A −1B | + | + | + | + |
| C3H | − | − | − | − | − |
| DBA | − | + | + | + | + |
| CBA | − | − | +/−<br>+2A −1B | +<br>+2A +/−1B | + |
| 129Sv | − | + | + | + | + |
| B6D2F1 | +/−<br>+2A −1B | + | + | + | + |
| OF1 | + | + | + | + | + |

+ = presence of antibodies
− = absence of antibodies

Figure 19:
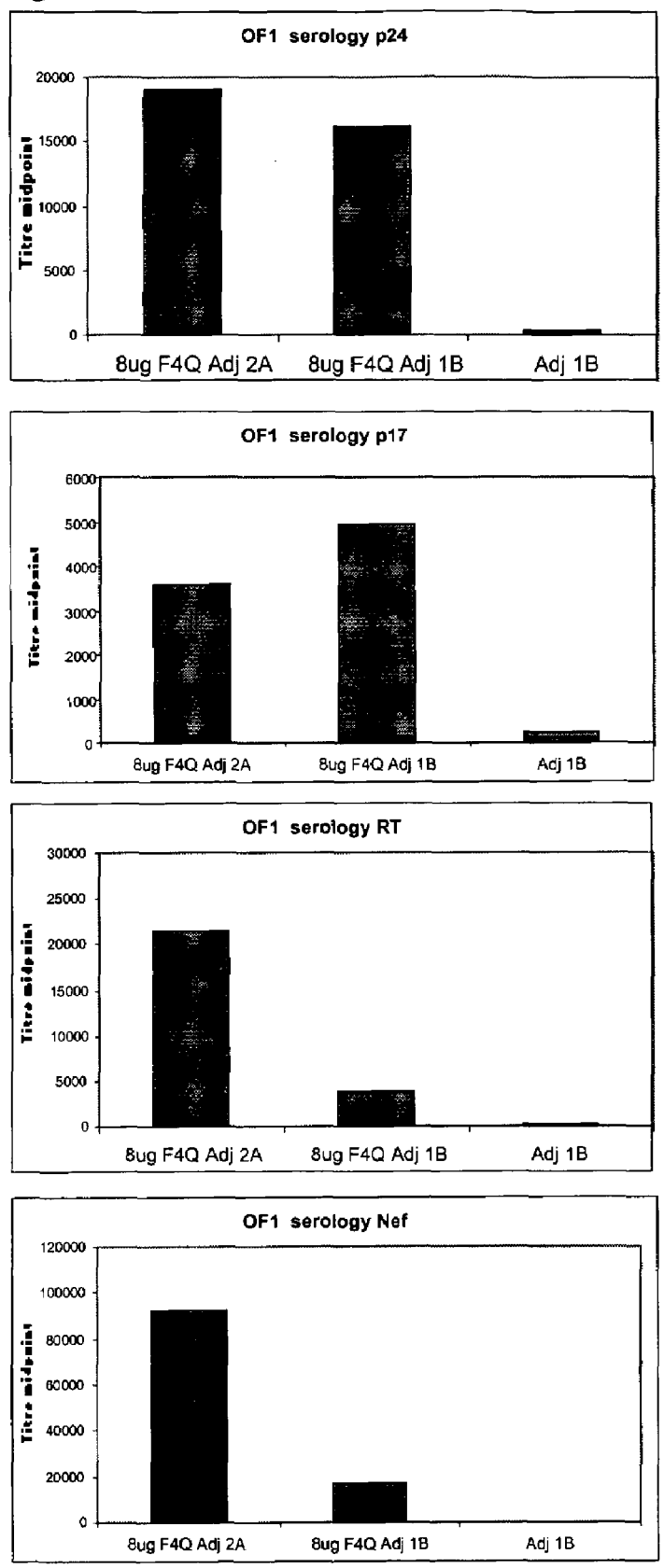
FIG. 19 is a series of bar graphs showing immunogenicity in mice.

OF1 mice mounted antibody responses to all four F4 components. The responses observed are shown in FIG. 19. +/− indicates that the response observed was weak or only observed with one of the two adjuvant. For example, B6D2F1 mice p17 responses: +/− overall with a +2A and −1B means that there was a response with 2A (not weak) and none with 1B. Balb/c mice p17 responses: −overall, with a +/−2A and a −1B, here the +/− means that the response with adjuvant 2A was weak.

Cellular responses were characterised by flow cytometry staining for CD4 and CD8, IFN□ and IL-2 expression (intracellular cytokine staining for IFN□ and IL-2 expression), following restimulation of spleen cells with p24, p17, RT or Nef specific peptides, using peptide library pools of 15 mers with 11 mer overlap. CD4 responses were the dominant cellular response observed. The following table, Table 3, summarises where antigen specific CD4+IL-2+ responses were observed for each mouse strain. Again, this is shown as presence or absence of a response.

TABLE 3

| mouse strain | p17 | p24 | Nef | RT |
|---|---|---|---|---|
| CB6F1 | −<br>+/−2A − 1B | + | + | + |
| Balb/c | − | +/−<br>weak | +/−<br>weak | + |
| C3H | + | + | − | + |
| DBA | + | + | + | + |
| CBA | + | +<br>−2A + 1B | − | + |
| 129Sv | + | + | − | + |
| B6D2F1 | − | + | + | + |
| OF1 | − | − | − | + |

+ = presence of CD4+IL-2+
− = absence of CD4+IL-2+

Figure 20:
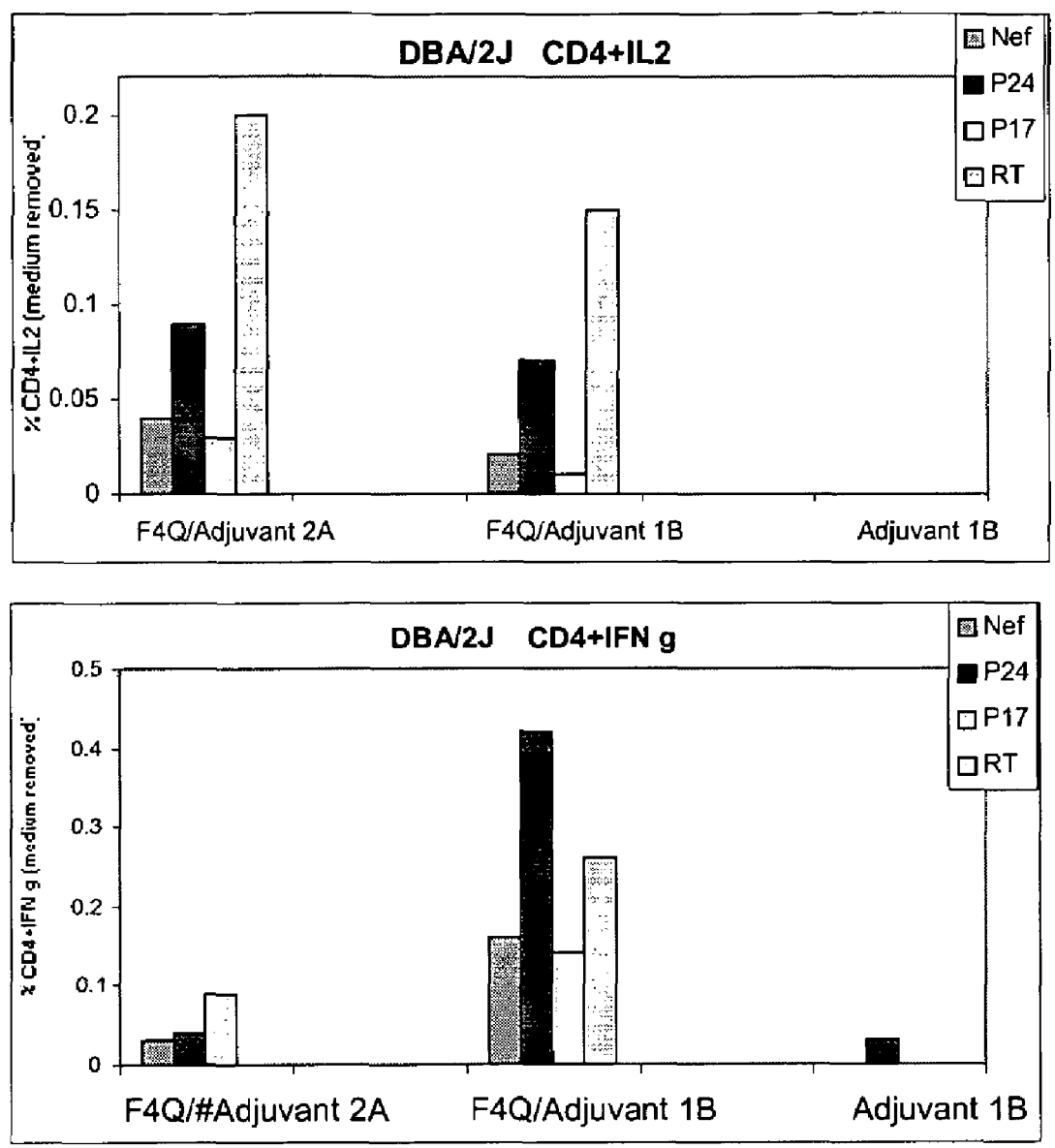
FIG. 20 is two bar graphs showing immunogenicity in mice.

DBA mice mounted CD4 responses to all four F4 components. The CD4+IL-2+ and CD4+IFN□+ responses observed for this mouse strain are shown in FIG. 20.

In summary, F4 formulated in either of the two adjuvant formulations is able to promote humoral and cellular responses to p24, p17, RT and Nef. This shows that each region of F4 is immunogenic in an in vivo situation.

The invention claimed is:

1. A fusion polypeptide comprising a Nef polypeptide, a reverse transcriptase (RT) polypeptide, a p17 Gag polypeptide, and a p24 Gag polypeptide, wherein there is at least one HIV antigen between the p17 Gag polypeptide and the p24 Gag polypeptide.

2. The fusion polypeptide of claim 1, wherein the RT polypeptide is p66.

3. The fusion polypeptide of claim 1, wherein the RT polypeptide is truncated at the C terminus such that it lacks the carboxy terminal RNase H domain.

4. The fusion polypeptide of claim 1, wherein the RT polypeptide is p51.

5. The fusion polypeptide of claim 1, wherein the RT polypeptide comprises a mutation at the amino acid position corresponding to position 592 in SEQ ID NO:2 where methionine is replaced by another amino acid residue.

6. The fusion polypeptide of claim 1, comprising from N-terminal to C-terminal: p24-RT-Nef-p17.

7. A process for purifying the fusion polypeptide of claim 1, the process comprising:
   i). providing a composition comprising the unpurified fusion polypeptide;
   ii). subjecting the composition to at least two chromatographic steps;
   iii). optionally carboxyamidating the fusion polypeptide; and
   iv) performing a buffer exchange step to provide the fusion polypeptide in a suitable buffer for a pharmaceutical formulation.

8. The process of claim 7, wherein there are no more than two chromatographic steps.

9. The process of claim 7, wherein the fusion polypeptide is carboxyamidated, and the carboxyamidation is performed between the at least two chromatographic steps.

10. The fusion polypeptide of claim 5, wherein methionine is replaced by lysine.

11. A pharmaceutical composition comprising the fusion polypeptide of claim 1.

12. The pharmaceutical composition of claim 11, further comprising a Th1 inducing adjuvant.

13. The pharmaceutical composition of claim 12, wherein the TH1 inducing adjuvant comprises QS21, 3D-MPL, or a combination of QS21 and 3D-MPL.

14. A pharmaceutical kit comprising:
   a) a pharmaceutical composition comprising the fusion polypeptide of claim 1; and
   b) a second pharmaceutical composition comprising a polynucleotide encoding at least one of a Nef epitope and a Gag epitope, wherein the at least one Nef epitope and Gag epitope are present in the polypeptide of a).

15. The pharmaceutical composition of claim 14, wherein the RT polypeptide is selected from the group consisting of: full length RT and RT truncated at the C terminus such that it lacks the carboxy terminal RNase H domain.

16. A pharmaceutical kit comprising:
   a) a pharmaceutical composition comprising a polynucleotide encoding the fusion polypeptide of claim 1; and
   b) a second pharmaceutical composition comprising a polypeptide comprising at least one of a Nef epitope and a Gag epitope, wherein the at least one Nef epitope and Gag epitope are present in the polypeptide of a).

17. The pharmaceutical composition of claim 16, wherein the RT polypeptide is selected from the group consisting of: full length RT and RT truncated at the C terminus such that it lacks the carboxy terminal RNase H domain.

18. The fusion polypeptide of claim 1, comprising from N-terminal to C-terminal: p24-RT-Nef-p17, wherein the amino acid at the position corresponding to position 592 in SEQ ID NO:2 is not methionine.

19. The fusion polypeptide of claim 18 where said amino acid is lysine.

20. The fusion polypeptide of claim 1, comprising from N-terminal to C-terminal: p24-p51RT-Nef-p17.

21. The fusion polypeptide of claim 1, comprising from N-terminal to C-terminal: p22-p51RT-Nef-p17, wherein the amino acid at the position corresponding to position 592 in SEQ ID NO:2 is not methionine.

22. The fusion polypeptide of claim 21 where said amino acid is lysine.

23. The fusion polypeptide of claim 1, comprising SEQ ID NO:2.

24. The fusion polypeptide of claim 1, comprising SEQ ID NO:15.

25. The fusion polypeptide of claim 1, comprising SEQ ID NO:19.

26. The fusion polypeptide of claim 1, where said RT polypeptide comprises a point mutation that removes reverse transcriptase enzyme activity, wherein said point mutation is the substitution of lysine for tryptophan at the amino acid position corresponding to position 464 in SEQ ID NO:2.

* * * * *

SEQUENCE LISTING

<160> NUMBER OF SEQ ID NOS: 20

<210> SEQ ID NO 1
<211> LENGTH: 3411
<212> TYPE: DNA
<213> ORGANISM: Artificial Sequence
<220> FEATURE:
<223> OTHER INFORMATION: p24-RT-Nef-p17 fusion

<400> SEQUENCE: 1

```
atggttatcg tgcagaacat ccaggggcaa atggtacatc aggccatatc acctagaact      60
ttaaatgcat gggtaaaagt agtagaagag aaggctttca gcccagaagt aatacccatg     120
ttttcagcat tatcagaagg agccacccca caagatttaa acaccatgct aaacacagtg     180
```

-continued

```
ggggggacatc aagcagccat gcaaatgtta aaagagacca tcaatgagga agctgcagaa    240
tgggatagag tacatccagt gcatgcaggg cctattgcac caggccagat gagagaacca    300
aggggaagtg acatagcagg aactactagt acccttcagg aacaaatagg atggatgaca    360
aataatccac ctatcccagt aggagaaatt tataaagat ggataatcct gggattaaat     420
aaaatagtaa gaatgtatag ccctaccagc attctggaca taagacaagg accaaaagaa    480
ccttttagag actatgtaga ccggttctat aaaactctaa gagccgagca agcttacag     540
gaggtaaaaa attggatgac agaaaccttg ttggtccaaa atgcgaaccc agattgtaag    600
actattttaa aagcattggg accagcggct acactagaag aaatgatgac agcatgtcag    660
ggagtaggag gacccggcca taaggcaaga gttttgcata tgggccccat tagccctatt    720
gagactgtgt cagtaaaatt aaagccagga atggatggcc caaagttaa acaatggcca    780
ttgacagaag aaaaaataaa agcattagta gaaatttgta cagagatgga aaaggaaggg   840
aaaatttcaa aaattgggcc tgaaaatcca tacaatactc cagtatttgc cataaagaaa    900
aaagacagta ctaatggag aaaattagta gatttcagag aacttaataa gagaactcaa    960
gacttctggg aagttcaatt aggaatacca catcccgcag ggttaaaaaa gaaaaaatca   1020
gtaacagtac tggatgtggg tgatgcatat ttttcagttc ccttagatga agacttcagg   1080
aaatatactg catttaccat acctagtata aacaatgaga caccagggat tagatatcag   1140
tacaatgtgc ttccacaggg atggaaagga tcaccagcaa tattccaaag tagcatgaca   1200
aaaatcttag agccttttag aaaacaaaat ccagacatag ttatctatca atacatggat   1260
gatttgtatg taggatctga cttagaaata gggcagcata gaacaaaaat agaggagctg   1320
agacaacatc tgttgaggtg gggacttacc acaccagaca aaaaacatca gaaagaacct   1380
ccattcctta aatgggtta tgaactccat cctgataaat ggacagtaca gcctatagtg   1440
ctgccagaaa aagacagctg gactgtcaat gacatacaga agttagtggg gaaattgaat   1500
tgggcaagtc agatttaccc agggattaaa gtaaggcaat tatgtaaact ccttagagga   1560
accaaagcac taacagaagt aataccacta acagaagaag cagagctaga actggcagaa   1620
aacagagaga ttctaaaaga accagtacat ggagtgtatt atgacccatc aaaagactta   1680
atagcagaaa tacagaagca ggggcaaggc caatggacat atcaaattta tcaagagcca   1740
tttaaaaatc tgaaaacagg aaaatatgca agaatgaggg gtgcccacac taatgatgta   1800
aaacaattaa cagaggcagt gcaaaaaata accacagaaa gcatagtaat atggggaaag   1860
actcctaaat ttaaactgcc catacaaaag gaaacatggg aaacatggtg gacagagtat   1920
tggcaagcca cctggattcc tgagtgggag tttgttaata cccctccttt agtgaaatta   1980
tggtaccagt tagagaaaga acccatagta ggagcagaaa ccttctatgt agatggggca   2040
gctaacaggg agactaaatt aggaaaagca ggatatgtta ctaatagagg aagacaaaaa   2100
gttgtcaccc taactgacac aacaaatcag aagactgagt tacaagcaat ttatctagct   2160
ttgcaggatt cgggattaga agtaaacata gtaacagact cacaatatgc attaggaatc   2220
attcaagcac aaccagatca aagtgaatca gagttagtca atcaaataat agagcagtta   2280
ataaaaaagg aaaaggtcta tctggcatgg gtaccagcac acaaaggaat tggaggaaat   2340
gaacaagtag ataaattagt cagtgctgga atcaggaaag tgctagctat gggtggcaag   2400
tggtcaaaaa gtagtgtggt tggatggcct actgtaaggg aaagaatgag acgagctgag   2460
ccagcagcag atggggtggg agcagcatct cgagacctgg aaaaacatgg agcaatcaca   2520
```

```
agtagcaata cagcagctac caatgctgct tgtgcctggc tagaagcaca agaggaggag    2580
gaggtgggtt ttccagtcac acctcaggta ccttttaagac caatgactta caaggcagct   2640
gtagatctta gccactttt aaaagaaaag gggggactgg aagggctaat tcactcccaa     2700
cgaagacaag atatccttga tctgtggatc taccacacac aaggctactt ccctgattgg    2760
cagaactaca caccagggcc agggtcaga tatccactga cctttggatg gtgctacaag     2820
ctagtaccag ttgagccaga taaggtagaa gaggccaata aggagagaa caccagcttg     2880 ttacaccctg tgagcctgca tggaatggat gaccctgaga gagaagtgtt agagtggagg    2940
tttgacagcc gcctagcatt tcatcacgtg gcccgagagc tgcatccgga gtacttcaag   3000
aactgcaggc ctatgggtgc gagagcgtca gtattaagcg ggggagaatt agatcgatgg   3060
gaaaaaattc ggttaaggcc agggggaaag aaaaaatata aattaaaaca tatagtatgg   3120
gcaagcaggg agctagaacg attcgcagtt aatcctggcc tgttagaaac atcagaaggc   3180
tgtagacaaa tactgggaca gctacaacca tcccttcaga caggatcaga gaacttaga   3240 tcattatata atacagtagc aaccctctat tgtgtgcatc aaaggataga gataaaagac   3300
accaaggaag ctttagacaa gatagaggaa gagcaaaaca aagtaagaa aaaagcacag   3360 caagcagcag ctgacacagg acacagcaat caggtcagcc aaaattacta a              3411

<210> SEQ ID NO 2
<211> LENGTH: 1136
<212> TYPE: PRT
<213> ORGANISM: Artificial Sequence
<220> FEATURE:
<223> OTHER INFORMATION: p24-RT-Nef-p17 fusion

<400> SEQUENCE: 2

Met Val Ile Val Gln Asn Ile Gln Gly Gln Met Val His Gln Ala Ile
1               5                   10                  15

Ser Pro Arg Thr Leu Asn Ala Trp Val Lys Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80

Trp Asp Arg Val His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205
```

```
Ala Ala Thr Leu Glu Glu Met Met Thr Ala Cys Gln Gly Val Gly Gly
        210                 215                 220
Pro Gly His Lys Ala Arg Val Leu His Met Gly Pro Ile Ser Pro Ile
225                 230                 235                 240
Glu Thr Val Ser Val Lys Leu Lys Pro Gly Met Asp Gly Pro Lys Val
                245                 250                 255
Lys Gln Trp Pro Leu Thr Glu Glu Lys Ile Lys Ala Leu Val Glu Ile
                260                 265                 270
Cys Thr Glu Met Glu Lys Glu Gly Lys Ile Ser Lys Ile Gly Pro Glu
            275                 280                 285
Asn Pro Tyr Asn Thr Pro Val Phe Ala Ile Lys Lys Lys Asp Ser Thr
290                 295                 300
Lys Trp Arg Lys Leu Val Asp Phe Arg Glu Leu Asn Lys Arg Thr Gln
305                 310                 315                 320
Asp Phe Trp Glu Val Gln Leu Gly Ile Pro His Pro Ala Gly Leu Lys
                325                 330                 335
Lys Lys Lys Ser Val Thr Val Leu Asp Val Gly Asp Ala Tyr Phe Ser
                340                 345                 350
Val Pro Leu Asp Glu Asp Phe Arg Lys Tyr Thr Ala Phe Thr Ile Pro
                355                 360                 365
Ser Ile Asn Asn Glu Thr Pro Gly Ile Arg Tyr Gln Tyr Asn Val Leu
370                 375                 380
Pro Gln Gly Trp Lys Gly Ser Pro Ala Ile Phe Gln Ser Ser Met Thr
385                 390                 395                 400
Lys Ile Leu Glu Pro Phe Arg Lys Gln Asn Pro Asp Ile Val Ile Tyr
                405                 410                 415
Gln Tyr Met Asp Asp Leu Tyr Val Gly Ser Asp Leu Glu Ile Gly Gln
                420                 425                 430
His Arg Thr Lys Ile Glu Glu Leu Arg Gln His Leu Leu Arg Trp Gly
                435                 440                 445
Leu Thr Thr Pro Asp Lys Lys His Gln Lys Glu Pro Pro Phe Leu Lys
        450                 455                 460
Met Gly Tyr Glu Leu His Pro Asp Lys Trp Thr Val Gln Pro Ile Val
465                 470                 475                 480
Leu Pro Glu Lys Asp Ser Trp Thr Val Asn Asp Ile Gln Lys Leu Val
                485                 490                 495
Gly Lys Leu Asn Trp Ala Ser Gln Ile Tyr Pro Gly Ile Lys Val Arg
                500                 505                 510
Gln Leu Cys Lys Leu Leu Arg Gly Thr Lys Ala Leu Thr Glu Val Ile
            515                 520                 525
Pro Leu Thr Glu Glu Ala Glu Leu Glu Leu Ala Glu Asn Arg Glu Ile
        530                 535                 540
Leu Lys Glu Pro Val His Gly Val Tyr Tyr Asp Pro Ser Lys Asp Leu
545                 550                 555                 560
Ile Ala Glu Ile Gln Lys Gln Gly Gln Gly Gln Trp Thr Tyr Gln Ile
                565                 570                 575
Tyr Gln Glu Pro Phe Lys Asn Leu Lys Thr Gly Lys Tyr Ala Arg Met
                580                 585                 590
Arg Gly Ala His Thr Asn Asp Val Lys Gln Leu Thr Glu Ala Val Gln
            595                 600                 605
Lys Ile Thr Thr Glu Ser Ile Val Ile Trp Gly Lys Thr Pro Lys Phe
        610                 615                 620
Lys Leu Pro Ile Gln Lys Glu Thr Trp Glu Thr Trp Trp Thr Glu Tyr
```

```
                625                 630                 635                 640
Trp Gln Ala Thr Trp Ile Pro Glu Trp Glu Phe Val Asn Thr Pro Pro
                645                 650                 655
Leu Val Lys Leu Trp Tyr Gln Leu Glu Lys Glu Pro Ile Val Gly Ala
                660                 665                 670
Glu Thr Phe Tyr Val Asp Gly Ala Ala Asn Arg Glu Thr Lys Leu Gly
                675                 680                 685
Lys Ala Gly Tyr Val Thr Asn Arg Gly Arg Gln Lys Val Val Thr Leu
                690                 695                 700
Thr Asp Thr Thr Asn Gln Lys Thr Glu Leu Gln Ala Ile Tyr Leu Ala
705                 710                 715                 720
Leu Gln Asp Ser Gly Leu Glu Val Asn Ile Val Thr Asp Ser Gln Tyr
                725                 730                 735
Ala Leu Gly Ile Ile Gln Ala Gln Pro Asp Gln Ser Glu Ser Glu Leu
                740                 745                 750
Val Asn Gln Ile Ile Glu Gln Leu Ile Lys Lys Glu Lys Val Tyr Leu
                755                 760                 765
Ala Trp Val Pro Ala His Lys Gly Ile Gly Gly Asn Glu Gln Val Asp
                770                 775                 780
Lys Leu Val Ser Ala Gly Ile Arg Lys Val Leu Ala Met Gly Gly Lys
785                 790                 795                 800
Trp Ser Lys Ser Ser Val Val Gly Trp Pro Thr Val Arg Glu Arg Met
                805                 810                 815
Arg Arg Ala Glu Pro Ala Ala Asp Gly Val Gly Ala Ala Ser Arg Asp
                820                 825                 830
Leu Glu Lys His Gly Ala Ile Thr Ser Ser Asn Thr Ala Ala Thr Asn
                835                 840                 845
Ala Ala Cys Ala Trp Leu Glu Ala Gln Glu Glu Glu Val Gly Phe
850                 855                 860
Pro Val Thr Pro Gln Val Pro Leu Arg Pro Met Thr Tyr Lys Ala Ala
865                 870                 875                 880
Val Asp Leu Ser His Phe Leu Lys Glu Lys Gly Gly Leu Glu Gly Leu
                885                 890                 895
Ile His Ser Gln Arg Arg Gln Asp Ile Leu Asp Leu Trp Ile Tyr His
                900                 905                 910
Thr Gln Gly Tyr Phe Pro Asp Trp Gln Asn Tyr Thr Pro Gly Pro Gly
                915                 920                 925
Val Arg Tyr Pro Leu Thr Phe Gly Trp Cys Tyr Lys Leu Val Pro Val
                930                 935                 940
Glu Pro Asp Lys Val Glu Glu Ala Asn Lys Gly Glu Asn Thr Ser Leu
945                 950                 955                 960
Leu His Pro Val Ser Leu His Gly Met Asp Asp Pro Glu Arg Glu Val
                965                 970                 975
Leu Glu Trp Arg Phe Asp Ser Arg Leu Ala Phe His His Val Ala Arg
                980                 985                 990
Glu Leu His Pro Glu Tyr Phe Lys Asn Cys Arg Pro Met Gly Ala Arg
                995                 1000                1005
Ala Ser Val Leu Ser Gly Gly Glu Leu Asp Arg Trp Glu Lys Ile Arg
                1010                1015                1020
Leu Arg Pro Gly Gly Lys Lys Lys Tyr Lys Leu Lys His Ile Val Trp
1025                1030                1035                1040
Ala Ser Arg Glu Leu Glu Arg Phe Ala Val Asn Pro Gly Leu Leu Glu
                1045                1050                1055
```

-continued

```
Thr Ser Glu Gly Cys Arg Gln Ile Leu Gly Gln Leu Gln Pro Ser Leu
        1060                1065                1070

Gln Thr Gly Ser Glu Glu Leu Arg Ser Leu Tyr Asn Thr Val Ala Thr
    1075                1080                1085

Leu Tyr Cys Val His Gln Arg Ile Glu Ile Lys Asp Thr Lys Glu Ala
    1090                1095                1100

Leu Asp Lys Ile Glu Glu Glu Gln Asn Lys Ser Lys Lys Lys Ala Gln
1105                1110                1115                1120

Gln Ala Ala Ala Asp Thr Gly His Ser Asn Gln Val Ser Gln Asn Tyr
                1125                1130                1135

<210> SEQ ID NO 3
<211> LENGTH: 3411
<212> TYPE: DNA
<213> ORGANISM: Artificial Sequence
<220> FEATURE:
<223> OTHER INFORMATION: F4co

<400> SEQUENCE: 3
```

| | | | | | |
|---|---|---|---|---|---|
| atggtcattg | ttcagaacat | acagggccaa | atggtccacc | aggcaattag | tccgcgaact | 60 |
| cttaatgcat | gggtgaaggt | cgtggaggaa | aaggcattct | ccccggaggt | cattccgatg | 120 |
| ttttctgcgc | tatctgaggg | cgcaacgccg | caagacctta | taccatgcta | acacggta | 180 |
| ggcgggcacc | aagccgctat | gcaaatgcta | aaagagacta | aaacgaaga | ggccgccgaa | 240 |
| tgggatcgag | tgcacccggt | gcacgccggc | ccaattgcac | caggccagat | gcgcgagccg | 300 |
| cgcgggtctg | atattgcagg | aactacgtct | acccttcagg | agcagattgg | gtggatgact | 360 |
| aacaatccac | caatcccggt | cggagagatc | tataagaggt | ggatcatact | gggactaaac | 420 |
| aagatagtcc | gcatgtattc | tccgacttct | atactggata | tacgccaagg | cccaaaggag | 480 |
| ccgttcaggg | actatgtcga | ccgattctat | aagacccttc | gcgcagagca | ggcatcccag | 540 |
| gaggtcaaaa | attggatgac | agaaactctt | ttggtgcaga | atgcgaatcc | ggattgtaaa | 600 |
| acaattttaa | aggctctagg | accggccgca | acgctagaag | agatgatgac | ggcttgtcag | 660 |
| ggagtcggtg | gaccggggca | taagcccgc | gtcttacaca | tgggcccgat | atctccgata | 720 |
| gaaacagttt | cggtcaagct | taaaccaggg | atggatggtc | caaaggtcaa | gcagtggccg | 780 |
| ctaacggaag | agaagattaa | ggcgctcgta | gagatttgta | ctgaaatgga | gaaggaaggc | 840 |
| aagataagca | agatcgggcc | agagaacccg | tacaatacac | cggtatttgc | aataaagaaa | 900 |
| aaggattcaa | caaaatggcg | aaagcttgta | gattttaggg | aactaaacaa | gcgaacccaa | 960 |
| gacttttggg | aagtccaact | agggatccca | catccagccg | gtctaaagaa | gaagaaatcg | 1020 |
| gtcacagtcc | tggatgtagg | agacgcatat | tttagtgtac | gcttgatga | ggacttccga | 1080 |
| aagtatactg | cgtttactat | accgagcata | aacaatgaaa | cgccaggcat | tcgctatcag | 1140 |
| tacaacgtgc | tcccgcaggg | ctggaagggg | tctccggcga | tatttcagag | ctgtatgaca | 1200 |
| aaaatacttg | aaccattccg | aaagcagaat | ccggatattg | taatttacca | atacatggac | 1260 |
| gatctctatg | tgggctcgga | tctagaaatt | gggcagcatc | gcactaagat | tgaggaactg | 1320 |
| aggcaacatc | tgcttcgatg | gggcctcact | actcccgaca | agaagcacca | gaaggagccg | 1380 |
| ccgttcctaa | agatgggcta | cgagcttcat | ccggacaagt | ggacagtaca | gccgatagtg | 1440 |
| ctgcccgaaa | aggattcttg | gaccgtaaat | gatattcaga | aactagtcgg | caagcttaac | 1500 |
| tgggcctctc | agatttaccc | aggcattaag | gtccgacagc | tttgcaagct | actgaggga | 1560 |
| actaaggctc | taacagaggt | catccccatta | acggaggaag | cagagcttga | gctggcagag | 1620 |

```
aatcgcgaaa ttcttaagga gccggtgcac ggggtatact acgacccctc caaggacctt    1680
atagccgaga tccagaagca ggggcagggc caatggacgt accagatata tcaagaaccg    1740
tttaagaatc tgaagactgg gaagtacgcg cgcatgcgag gggctcatac taatgatgta    1800
aagcaactta cggaagcagt acaaaagatt actactgagt ctattgtgat atggggcaag    1860
accccaaagt tcaagctgcc catacagaag gaaacatggg aaacatggtg gactgaatat    1920
tggcaagcta cctggattcc agaatgggaa tttgtcaaca cgccgccact tgttaagctt    1980
tggtaccagc ttgaaaagga gccgatagta ggggcagaga ccttctatgt cgatggcgcc    2040
gcgaatcgcg aaacgaagct aggcaaggcg ggatacgtga ctaataggggg ccgccaaaag   2100 gtcgtaaccc ttacggatac caccaatcag aagactgaac tacaagcgat ttaccttgca    2160
cttcaggata gtggcctaga ggtcaacata gtcacggact ctcaatatgc gcttggcatt    2220
attcaagcgc agccagatca aagcgaaagc gagcttgtaa accaaataat agaacagctt    2280
ataaagaaag agaaggtata tctggcctgg gtccccgctc acaagggaat tggcggcaat    2340
gagcaagtgg acaagctagt cagcgctggg attcgcaagg ttcttgcgat ggggggtaag    2400
tggtctaagt ctagcgtagt cggctggccg acagtccgcg agcgcatgcg acgcgccgaa    2460
ccagccgcag atggcgtggg ggcagcgtct agggatctgg agaagcacgg ggctataact    2520
tccagtaaca cggcggcgac gaacgccgca tgcgcatggt tagaagccca agaagaggaa    2580
gaagtagggt ttccggtaac tccccaggtg ccgttaaggc cgatgaccta taaggcagcg    2640
gtggatcttt ctcacttcct taaggagaaa gggggggctgg agggcttaat tcacagccag   2700
aggcgacagg atattcttga tctgtggatt taccataccc aggggtactt tccggactgg    2760
cagaattaca ccccgggggcc aggcgtgcgc tatcccctga ctttcgggtg gtgctacaaa   2820
ctagtcccag tggaacccga caaggtcgaa gaggctaata agggcgagaa cacttctctt    2880
cttcacccgg taagcctgca cgggatggat gacccagaac gagaggttct agaatggagg    2940
ttcgactctc gacttgcgtt ccatcacgta gcacgcgagc tgcatccaga atatttcaag    3000
aactgccgcc caatgggcgc cagggccagt gtacttagtg gcggagaact agatcgatgg    3060
gaaaagatac gcctacgccc ggggggcaag aagaagtaca agcttaagca cattgtgtgg    3120
gcctctcgcg aacttgagcg attcgcagtg aatccaggcc tgcttgagac gagtgaaggc    3180
tgtaggcaaa ttctggggca gctacagccg agcctacaga ctggcagcga ggagcttcgt    3240
agtctttata ataccgtcgc gactctctac tgcgttcatc aacgaattga aataaaggat    3300
actaaagagg cccttgataa aattgaggag gaacagaata agtcgaaaaa gaaggcccag    3360
caggccgccg ccgacaccgg gcacagcaac caggtgtccc aaaactacta a             3411
```

<210> SEQ ID NO 4
<211> LENGTH: 1302
<212> TYPE: DNA
<213> ORGANISM: Artificial Sequence
<220> FEATURE:
<223> OTHER INFORMATION: p51 RT
<400> SEQUENCE: 4

```
atgagtactg gtccgatctc tccgatagaa acagtttcgg tcaagcttaa accagggatg     60
gatggtccaa aggtcaagca gtggccgcta acggaagaga agattaaggc gctcgtagag    120
atttgtactg aaatggagaa ggaaggcaag ataagcaaga tcgggccaga gaacccgtac    180
aatacaccgg tatttgcaat aaagaagaag gattcaacaa aatggcgaaa gcttgtagat    240
```

-continued

```
tttagggaac taaacaagcg aacccaagac ttttgggaag tccaactagg tatcccacat    300
ccagccggtc taaagaagaa gaaatcggtc acagtcctgg atgtaggaga cgcatatttt    360
agtgtaccgc ttgatgagga cttccgaaag tatactgcgt ttactatacc gagcataaac    420
aatgaaacgc caggcattcg ctatcagtac aacgtgctcc cgcagggctg aagggggtct    480
ccggcgatat ttcagagctc tatgacaaaa atacttgaac cattccgaaa gcagaatccg    540
gatattgtaa tttaccaata catggacgat ctctatgtgg gctcggatct agaaattggg    600
cagcatcgca ctaagattga ggaactgagg caacatctgc ttcgatgggg cctcactact    660
cccgacaaga agcaccagaa ggagccgccg ttcctaaaga tgggctacga gcttcatccg    720
gacaagtgga cagtacagcc gatagtgctg cccgaaaagg attcttggac cgtaaatgat    780
attcagaaac tagtcggcaa gcttaactgg gcctctcaga tttacccagg cattaaggtc    840
cgacagcttt gcaagctact gaggggaact aaggctctaa cagaggtcat cccattaacg    900
gaggaagcag agcttgagct ggcagagaat cgcgaaattc ttaaggagcc ggtgcacggg    960
gtatactacg accccctcca ggaccttata gccgagatcc agaagcaggg gcagggccaa   1020
tggacgtacc agatatatca agaaccgttt aagaatctga agactgggaa gtacgcgcgc   1080
atgcgagggg ctcatactaa tgatgtaaag caacttacgg aagcagtaca aaagattact   1140
actgagtcta ttgtgatatg gggcaagacc ccaaagttca agctgcccat acagaaggaa   1200
acatgggaaa catggtggac tgaatattgg caagctacct ggattccaga atgggaattt   1260
gtcaacacgc cgccgctggt aaaactgagg cctgctagct aa                      1302
```

<210> SEQ ID NO 5
<211> LENGTH: 433
<212> TYPE: PRT
<213> ORGANISM: Artificial Sequence
<220> FEATURE:
<223> OTHER INFORMATION: p51 RT

<400> SEQUENCE: 5

```
Met Ser Thr Gly Pro Ile Ser Pro Ile Glu Thr Val Ser Val Lys Leu
  1               5                  10                  15

Lys Pro Gly Met Asp Gly Pro Lys Val Lys Gln Trp Pro Leu Thr Glu
             20                  25                  30

Glu Lys Ile Lys Ala Leu Val Glu Ile Cys Thr Glu Met Glu Lys Glu
         35                  40                  45

Gly Lys Ile Ser Lys Ile Gly Pro Glu Asn Pro Tyr Asn Thr Pro Val
     50                  55                  60

Phe Ala Ile Lys Lys Lys Asp Ser Thr Lys Trp Arg Lys Leu Val Asp
 65                  70                  75                  80

Phe Arg Glu Leu Asn Lys Arg Thr Gln Asp Phe Trp Glu Val Gln Leu
                 85                  90                  95

Gly Ile Pro His Pro Ala Gly Leu Lys Lys Lys Ser Val Thr Val
            100                 105                 110

Leu Asp Val Gly Asp Ala Tyr Phe Ser Val Pro Leu Asp Glu Asp Phe
        115                 120                 125

Arg Lys Tyr Thr Ala Phe Thr Ile Pro Ser Ile Asn Asn Glu Thr Pro
    130                 135                 140

Gly Ile Arg Tyr Gln Tyr Asn Val Leu Pro Gln Gly Trp Lys Gly Ser
145                 150                 155                 160

Pro Ala Ile Phe Gln Ser Ser Met Thr Lys Ile Leu Glu Pro Phe Arg
                165                 170                 175
```

```
Lys Gln Asn Pro Asp Ile Val Ile Tyr Gln Tyr Met Asp Asp Leu Tyr
                180                 185                 190
Val Gly Ser Asp Leu Glu Ile Gly Gln His Arg Thr Lys Ile Glu Glu
            195                 200                 205
Leu Arg Gln His Leu Leu Arg Trp Gly Leu Thr Thr Pro Asp Lys Lys
        210                 215                 220
His Gln Lys Glu Pro Pro Phe Leu Lys Met Gly Tyr Glu Leu His Pro
225                 230                 235                 240
Asp Lys Trp Thr Val Gln Pro Ile Val Leu Pro Glu Lys Asp Ser Trp
                245                 250                 255
Thr Val Asn Asp Ile Gln Lys Leu Val Gly Lys Leu Asn Trp Ala Ser
            260                 265                 270
Gln Ile Tyr Pro Gly Ile Lys Val Arg Gln Leu Cys Lys Leu Leu Arg
        275                 280                 285
Gly Thr Lys Ala Leu Thr Glu Val Ile Pro Leu Thr Glu Glu Ala Glu
    290                 295                 300
Leu Glu Leu Ala Glu Asn Arg Glu Ile Leu Lys Glu Pro Val His Gly
305                 310                 315                 320
Val Tyr Tyr Asp Pro Ser Lys Asp Leu Ile Ala Glu Ile Gln Lys Gln
                325                 330                 335
Gly Gln Gly Gln Trp Thr Tyr Gln Ile Tyr Gln Glu Pro Phe Lys Asn
            340                 345                 350
Leu Lys Thr Gly Lys Tyr Ala Arg Met Arg Gly Ala His Thr Asn Asp
        355                 360                 365
Val Lys Gln Leu Thr Glu Ala Val Gln Lys Ile Thr Thr Glu Ser Ile
    370                 375                 380
Val Ile Trp Gly Lys Thr Pro Lys Phe Lys Leu Pro Ile Gln Lys Glu
385                 390                 395                 400
Thr Trp Glu Thr Trp Trp Thr Glu Tyr Trp Gln Ala Thr Trp Ile Pro
                405                 410                 415
Glu Trp Glu Phe Val Asn Thr Pro Pro Leu Val Lys Leu Arg Pro Ala
            420                 425                 430
Ser

<210> SEQ ID NO 6
<211> LENGTH: 1023
<212> TYPE: DNA
<213> ORGANISM: Artificial Sequence
<220> FEATURE:
<223> OTHER INFORMATION: Nef p17

<400> SEQUENCE: 6
atgggtggca agtggtcaaa aagtagtgtg gttggatggc ctactgtaag ggaaagaatg      60
agacgagctg agccagcagc agatgggtg ggagcagcat ctcgagacct ggaaaaacat     120
ggagcaatca caagtagcaa tacagcagct accaatgctg cttgtgcctg gctagaagca     180
caagaggagg aggaggtggg ttttccagtc acacctcagg tacctttaag accaatgact     240
tacaaggcag ctgtagatct tagccacttt ttaaaagaaa aggggggact ggaagggcta     300
attcactccc aacgaagaca agatatcctt gatctgtgga tctaccacac acaaggctac     360
ttccctgatt ggcagaacta cacaccaggg ccagggtca gatatccact gacctttgga     420
tggtgctaca agctagtacc agttgagcca gataaggtag aagaggccaa taaggagag      480 aacaccagct tgttacaccc tgtgagcctg catggaatgg atgacccga gagaagtg       540 ttagagtgga ggtttgacag ccgcctagca tttcatcacg tggcccgaga gctgcatccg     600
```

```
gagtacttca agaactgcag gcctatgggt gcgagagcgt cagtattaag cgggggagaa      660
ttagatcgat gggaaaaaat tcggttaagg ccagggggaa agaaaaaata taaattaaaa      720
catatagtat gggcaagcag ggagctagaa cgattcgcag ttaatcctgg cctgttagaa      780
acatcagaag gctgtagaca aatactggga cagctacaac catcccttca gacaggatca      840
gaagaactta gatcattata taatacagta gcaaccctct attgtgtgca tcaaaggata      900
gagataaaag acaccaagga agctttagac aagatagagg aagagcaaaa caaaagtaag      960
aaaaaagcac agcaagcagc agctgacaca ggacacagca atcaggtcag ccaaaattac     1020
taa                                                                   1023
```

<210> SEQ ID NO 7
<211> LENGTH: 340
<212> TYPE: PRT
<213> ORGANISM: Artificial Sequence
<220> FEATURE:
<223> OTHER INFORMATION: Nef p17 (NP)

<400> SEQUENCE: 7

```
Met Gly Gly Lys Trp Ser Lys Ser Ser Val Val Gly Trp Pro Thr Val
  1               5                  10                  15

Arg Glu Arg Met Arg Arg Ala Glu Pro Ala Ala Asp Gly Val Gly Ala
             20                  25                  30

Ala Ser Arg Asp Leu Glu Lys His Gly Ala Ile Thr Ser Ser Asn Thr
         35                  40                  45

Ala Ala Thr Asn Ala Ala Cys Ala Trp Leu Glu Ala Gln Glu Glu Glu
     50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys Arg Pro
        195                 200                 205

Met Gly Ala Arg Ala Ser Val Leu Ser Gly Gly Glu Leu Asp Arg Trp
    210                 215                 220

Glu Lys Ile Arg Leu Arg Pro Gly Gly Lys Lys Tyr Lys Leu Lys
225                 230                 235                 240

His Ile Val Trp Ala Ser Arg Glu Leu Glu Arg Phe Ala Val Asn Pro
                245                 250                 255

Gly Leu Leu Glu Thr Ser Glu Gly Cys Arg Gln Ile Leu Gly Gln Leu
            260                 265                 270

Gln Pro Ser Leu Gln Thr Gly Ser Glu Glu Leu Arg Ser Leu Tyr Asn
```

-continued

```
                      275                 280                 285
Thr Val Ala Thr Leu Tyr Cys Val His Gln Arg Ile Glu Ile Lys Asp
        290                 295                 300

Thr Lys Glu Ala Leu Asp Lys Ile Glu Glu Gln Asn Lys Ser Lys
305                 310                 315                 320

Lys Lys Ala Gln Gln Ala Ala Ala Asp Thr Gly His Ser Asn Gln Val
                325                 330                 335

Ser Gln Asn Tyr
        340

<210> SEQ ID NO 8
<211> LENGTH: 1029
<212> TYPE: DNA
<213> ORGANISM: Artificial Sequence
<220> FEATURE:
<223> OTHER INFORMATION: p17 Nef

<400> SEQUENCE: 8
```

| | | | | | |
|---|---|---|---|---|---|
| atgggtgcga | gagcgtcagt | attaagcggg | ggagaattag | atcgatggga | aaaaattcgg     60 |
| ttaaggccag | ggggaaagaa | aaatataaa | ttaaaacata | tagtatgggc | aagcagggag    120 |
| ctagaacgat | tcgcagttaa | tcctggcctg | ttagaaacat | cagaaggctg | tagacaaata    180 |
| ctgggacagc | tacaaccatc | ccttcagaca | ggatcagaag | aacttagatc | attatataat    240 |
| acagtagcaa | ccctctattg | tgtgcatcaa | aggatagaga | taaaagacac | caaggaagct    300 |
| ttagacaaga | tagaggaaga | gcaaaacaaa | agtaagaaaa | agcacagca | agcagcagct    360 |
| gacacaggac | acagcaatca | ggtcagccaa | aattaccctcg | acaggcctat | gggtggcaag    420 |
| tggtcaaaaa | gtagtgtggt | tggatggcct | actgtaaggg | aaagaatgag | acgagctgag    480 |
| ccagcagcag | atggggtggg | agcagcatct | cgagacctgg | aaaaacatgg | agcaatcaca    540 |
| agtagcaata | cagcagctac | caatgctgct | tgtgcctggc | tagaagcaca | agaggaggag    600 |
| gaggtgggtt | ttccagtcac | acctcaggta | cctttaagac | caatgactta | caaggcagct    660 |
| gtagatctta | gccacttttt | aaaagaaaag | gggggactgg | aagggctaat | tcactcccaa    720 |
| cgaagacaag | atatccttga | tctgtggatc | taccacacac | aaggctactt | ccctgattgg    780 |
| cagaactaca | caccagggcc | aggggtcaga | tatccactga | cctttggatg | gtgctacaag    840 |
| ctagtaccag | ttgagccaga | taaggtagaa | gaggccaata | aggagagaa | caccagcttg    900 |
| ttacaccctg | tgagcctgca | tggaatggat | gaccctgaga | gagaagtgtt | agagtggagg    960 |
| tttgacagcc | gcctagcatt | tcatcacgtg | gcccgagagc | tgcatccgga | gtacttcaag   1020 |
| aactgctaa | | | | |                                                           1029 |

```
<210> SEQ ID NO 9
<211> LENGTH: 342
<212> TYPE: PRT
<213> ORGANISM: Artificial Sequence
<220> FEATURE:
<223> OTHER INFORMATION: p17 Nef (PN)

<400> SEQUENCE: 9

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45
```

```
Gly Leu Leu Glu Thr Ser Glu Gly Cys Arg Gln Ile Leu Gly Gln Leu
 50                  55                  60
Gln Pro Ser Leu Gln Thr Gly Ser Glu Glu Leu Arg Ser Leu Tyr Asn
 65                  70                  75                  80
Thr Val Ala Thr Leu Tyr Cys Val His Gln Arg Ile Glu Ile Lys Asp
                 85                  90                  95
Thr Lys Glu Ala Leu Asp Lys Ile Glu Glu Gln Asn Lys Ser Lys
            100                 105                 110
Lys Lys Ala Gln Gln Ala Ala Ala Asp Thr Gly His Ser Asn Gln Val
            115                 120                 125
Ser Gln Asn Tyr Leu Asp Arg Pro Met Gly Gly Lys Trp Ser Lys Ser
130                 135                 140
Ser Val Gly Trp Pro Thr Val Arg Glu Arg Met Arg Arg Ala Glu
145                 150                 155                 160
Pro Ala Ala Asp Gly Val Gly Ala Ala Ser Arg Asp Leu Glu Lys His
                165                 170                 175
Gly Ala Ile Thr Ser Ser Asn Thr Ala Ala Thr Asn Ala Ala Cys Ala
                180                 185                 190
Trp Leu Glu Ala Gln Glu Glu Glu Val Gly Phe Pro Val Thr Pro
            195                 200                 205
Gln Val Pro Leu Arg Pro Met Thr Tyr Lys Ala Ala Val Asp Leu Ser
210                 215                 220
His Phe Leu Lys Glu Lys Gly Gly Leu Glu Gly Leu Ile His Ser Gln
225                 230                 235                 240
Arg Arg Gln Asp Ile Leu Asp Leu Trp Ile Tyr His Thr Gln Gly Tyr
                245                 250                 255
Phe Pro Asp Trp Gln Asn Tyr Thr Pro Gly Pro Gly Val Arg Tyr Pro
            260                 265                 270
Leu Thr Phe Gly Trp Cys Tyr Lys Leu Val Pro Val Glu Pro Asp Lys
            275                 280                 285
Val Glu Glu Ala Asn Lys Gly Glu Asn Thr Ser Leu Leu His Pro Val
290                 295                 300
Ser Leu His Gly Met Asp Asp Pro Glu Arg Glu Val Leu Glu Trp Arg
305                 310                 315                 320
Phe Asp Ser Arg Leu Ala Phe His His Val Ala Arg Glu Leu His Pro
                325                 330                 335
Glu Tyr Phe Lys Asn Cys
            340

<210> SEQ ID NO 10
<211> LENGTH: 1041
<212> TYPE: DNA
<213> ORGANISM: Artificial Sequence
<220> FEATURE:
<223> OTHER INFORMATION: Nef-linker-p17

<400> SEQUENCE: 10
atgggtggca agtggtcaaa aagtagtgtg gttggatggc ctactgtaag ggaaagaatg    60
agacgagctg agccagcagc agatgggggtg ggagcagcat ctcgagacct ggaaaaacat   120
ggagcaatca aagtagcaa tacagcagct accaatgctg cttgtgcctg gctagaagca   180
caagaggagg aggaggtggg ttttccagtc acacctcagg tacctttaag accaatgact   240
tacaaggcag ctgtagatct tagccacttt ttaaaagaaa agggggggact ggaagggcta   300 attcactccc aacgaagaca agatatcctt gatctgtgga tctaccacac acaaggctac   360
```

-continued

```
ttccctgatt ggcagaacta cacaccaggg ccaggggtca gatatccact gacctttgga      420
tggtgctaca agctagtacc agttgagcca gataaggtag aagaggccaa taaaggagag      480
aacaccagct tgttcaccc tgtgagcctg catggaatgg atgaccctga gagaagtg         540 ttagagtgga ggtttgacag ccgcctagca tttcatcacg tggcccgaga gctgcatccg      600
gagtacttca gaactgcag gcctggatcc ggtggcggcc ctatgggtgc gagagcgtca       660
gtattaagcg ggggagaatt agatcgatgg gaaaaaattc ggttaaggcc aggggggaaag    720 aaaaaatata aattaaaaca tatagtatgg gcaagcaggg agctagaacg attcgcagtt     780
aatcctggcc tgttagaaac atcagaaggc tgtagacaaa tactgggaca gctacaacca     840
tcccttcaga caggatcaga agaacttaga tcattatata atacagtagc aaccctctat     900
tgtgtgcatc aaaggataga gataaaagac accaaggaag ctttagacaa gatagaggaa     960
gagcaaaaca aaagtaagaa aaaagcacag caagcagcag ctgacacagg acacagcaat    1020
caggtcagcc aaaattacta a                                              1041
```

<210> SEQ ID NO 11
<211> LENGTH: 346
<212> TYPE: PRT
<213> ORGANISM: Artificial Sequence
<220> FEATURE:
<223> OTHER INFORMATION: Nef-linker-p17 (NLP)

<400> SEQUENCE: 11

```
Met Gly Gly Lys Trp Ser Lys Ser Ser Val Val Gly Trp Pro Thr Val
 1               5                  10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys Arg Pro
        195                 200                 205

Gly Ser Gly Gly Gly Pro Met Gly Ala Arg Ala Ser Val Leu Ser Gly
    210                 215                 220

Gly Glu Leu Asp Arg Trp Glu Lys Ile Arg Leu Arg Pro Gly Gly Lys
225                 230                 235                 240
```

```
Lys Lys Tyr Lys Leu Lys His Ile Val Trp Ala Ser Arg Glu Leu Glu
            245                 250                 255

Arg Phe Ala Val Asn Pro Gly Leu Leu Glu Thr Ser Glu Gly Cys Arg
        260                 265                 270

Gln Ile Leu Gly Gln Leu Gln Pro Ser Leu Gln Thr Gly Ser Glu Glu
            275                 280                 285

Leu Arg Ser Leu Tyr Asn Thr Val Ala Thr Leu Tyr Cys Val His Gln
        290                 295                 300

Arg Ile Glu Ile Lys Asp Thr Lys Glu Ala Leu Asp Lys Ile Glu Glu
305                 310                 315                 320

Glu Gln Asn Lys Ser Lys Lys Lys Ala Gln Gln Ala Ala Ala Asp Thr
                325                 330                 335

Gly His Ser Asn Gln Val Ser Gln Asn Tyr
            340                 345

<210> SEQ ID NO 12
<211> LENGTH: 1047
<212> TYPE: DNA
<213> ORGANISM: Artificial Sequence
<220> FEATURE:
<223> OTHER INFORMATION: p17-linker-Nef

<400> SEQUENCE: 12
atgggtgcga gagcgtcagt attaagcggg ggagaattag atcgatggga aaaaattcgg        60
ttaaggccag ggggaaagaa aaatataaa ttaaaacata tagtatgggc aagcagggag       120
ctagaacgat tcgcagttaa tcctggcctg ttagaaacat cagaaggctg tagacaaata       180
ctgggacagc tacaaccatc ccttcagaca ggatcagaag aacttagatc attatataat       240
acagtagcaa ccctctattg tgtgcatcaa aggatagaga taaaagacac caaggaagct       300
ttagacaaga tagaggaaga gcaaaacaaa agtaagaaaa agcacagca agcagcagct       360 gacacaggac acagcaatca ggtcagccaa aattacctcg acaggcctgg atccggtggc       420
ggtcctatgg gtggcaagtg gtcaaaaagt agtgtggttg gatggcctac tgtaagggaa       480
agaatgagac gagctgagcc agcagcagat ggggtgggag cagcatctcg agacctggaa       540
aaacatggag caatcacaag tagcaataca gcagctacca atgctgcttg tgcctggcta       600
gaagcacaag aggaggagga ggtgggtttt ccagtcacac ctcaggtacc tttaagacca       660
atgacttaca aggcagctgt agatcttagc cacttttaa aagaaaaggg gggactggaa       720
gggctaattc actcccaacg aagacaagat atccttgatc tgtggatcta ccacacacaa       780
ggctacttcc ctgattggca gaactacaca ccagggccag ggtcagata tccactgacc       840 tttggatggt gctacaagct agtaccagtt gagccagata aggtagaaga ggccaataaa       900
ggagagaaca ccagcttgtt acaccctgtg agcctgcatg gaatggatga ccctgagaga       960
gaagtgttag agtggaggtt tgacagccgc ctagcatttc atcacgtggc ccgagagctg      1020
catccggagt acttcaagaa ctgctaa                                          1047

<210> SEQ ID NO 13
<211> LENGTH: 348
<212> TYPE: PRT
<213> ORGANISM: Artificial Sequence
<220> FEATURE:
<223> OTHER INFORMATION: p17-linker-Nef (PLN)

<400> SEQUENCE: 13

Met Gly Ala Arg Ala Ser Val Leu Ser Gly Gly Glu Leu Asp Arg Trp
1               5                   10                  15
```

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
        50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Leu Asp Arg Pro Gly Ser Gly Gly Pro Met Gly
    130                 135                 140

Gly Lys Trp Ser Lys Ser Ser Val Val Gly Trp Pro Thr Val Arg Glu
145                 150                 155                 160

Arg Met Arg Arg Ala Glu Pro Ala Ala Asp Gly Val Gly Ala Ala Ser
                165                 170                 175

Arg Asp Leu Glu Lys His Gly Ala Ile Thr Ser Ser Asn Thr Ala Ala
            180                 185                 190

Thr Asn Ala Ala Cys Ala Trp Leu Glu Ala Gln Glu Glu Glu Glu Val
        195                 200                 205

Gly Phe Pro Val Thr Pro Gln Val Pro Leu Arg Pro Met Thr Tyr Lys
    210                 215                 220

Ala Ala Val Asp Leu Ser His Phe Leu Lys Glu Lys Gly Gly Leu Glu
225                 230                 235                 240

Gly Leu Ile His Ser Gln Arg Arg Gln Asp Ile Leu Asp Leu Trp Ile
                245                 250                 255

Tyr His Thr Gln Gly Tyr Phe Pro Asp Trp Gln Asn Tyr Thr Pro Gly
            260                 265                 270

Pro Gly Val Arg Tyr Pro Leu Thr Phe Gly Trp Cys Tyr Lys Leu Val
        275                 280                 285

Pro Val Glu Pro Asp Lys Val Glu Glu Ala Asn Lys Gly Glu Asn Thr
    290                 295                 300

Ser Leu Leu His Pro Val Ser Leu His Gly Met Asp Asp Pro Glu Arg
305                 310                 315                 320

Glu Val Leu Glu Trp Arg Phe Asp Ser Arg Leu Ala Phe His His Val
                325                 330                 335

Ala Arg Glu Leu His Pro Glu Tyr Phe Lys Asn Cys
            340                 345

<210> SEQ ID NO 14
<211> LENGTH: 3411
<212> TYPE: DNA
<213> ORGANISM: Artificial Sequence
<220> FEATURE:
<223> OTHER INFORMATION: p24-RT*-Nef-p17 (F4*)

<400> SEQUENCE: 14
atggttatcg tgcagaacat ccaggggcaa atggtacatc aggccatatc acctagaact     60
ttaaatgcat gggtaaaagt agtagaagag aaggctttca gcccagaagt aatacccatg    120
ttttcagcat tatcagaagg agccacccca caagatttaa acaccatgct aaacacagtg    180

```
gggggacatc aagcagccat gcaaatgtta aaagagacca tcaatgagga agctgcagaa      240
tgggatagag tacatccagt gcatgcaggg cctattgcac caggccagat gagagaacca      300
aggggaagtg acatagcagg aactactagt acccttcagg aacaaatagg atggatgaca      360
aataatccac ctatcccagt aggagaaatt tataaagat ggataatcct gggattaaat       420
aaaatagtaa gaatgtatag ccctaccagc attctggaca taagacaagg accaaaagaa      480
ccttttagag actatgtaga ccggttctat aaaactctaa gagccgagca agcttcacag      540
gaggtaaaaa attggatgac agaaaccttg ttggtccaaa atgcgaaccc agattgtaag      600
actattttaa aagcattggg accagcggct acactagaag aaatgatgac agcatgtcag      660
ggagtaggag gacccggcca taaggcaaga gttttgcata tgggcccat tagccctatt       720 gagactgtgt cagtaaaatt aaagccagga atggatggcc caaagttaa acaatggcca      780 ttgacagaag aaaaaataaa agcattagta gaaatttgta cagagatgga aaaggaaggg      840
aaaatttcaa aaattgggcc tgaaaatcca tacaatactc cagtatttgc cataaagaaa      900
aaagacagta ctaaatggag aaaattagta gatttcagag aacttaataa gagaactcaa      960
gacttctggg aagttcaatt aggaatacca catcccgcag ggttaaaaaa gaaaaaatca     1020
gtaacagtac tggatgtggg tgatgcatat ttttcagttc ccttagatga agacttcagg     1080
aaatatactg catttaccat acctagtata aacaatgaga caccagggat tagatatcag     1140
tacaatgtgc ttccacaggg atggaaagga tcaccagcaa tattccaaag tagcatgaca     1200
aaaatcttag agccttttag aaaacaaaat ccagacatag ttatctatca atacatggat     1260
gatttgtatg taggatctga cttagaaata gggcagcata gaacaaaaat agaggagctg     1320
agacaacatc tgttgaggtg gggacttacc acaccagaca aaaaacatca gaaagaacct     1380
ccattcctta aatgggtta tgaactccat cctgataaat ggacagtaca gcctatagtg      1440
ctgccagaaa aagacagctg gactgtcaat gacatacaga agttagtggg aaaattgaat     1500
tgggcaagtc agatttaccc agggattaaa gtaaggcaat tatgtaaact ccttagagga     1560
accaaagcac taacagaagt aataccacta acagaagaag cagagctaga actggcagaa     1620
aacagagaga ttctaaaaga accagtacat ggagtgtatt atgacccatc aaaagactta     1680
atagcagaaa tacagaagca ggggcaaggc caatggacat atcaaattta tcaagagcca     1740
tttaaaaatc tgaaaacagg aaaatatgca cgtaaacgcg gtgcccacac taatgatgta     1800
aaacaattaa cagaggcagt gcaaaaaata ccacagaaa gcatagtaat atggggaaag      1860
actcctaaat ttaaactgcc catacaaaag gaaacatggg aaacatggtg gacagagtat     1920
tggcaagcca cctggattcc tgagtgggag tttgttaata cccctccttt agtgaaatta     1980
tggtaccagt tagagaaaga acccatagta ggagcagaaa ccttctatgt agatggggca     2040
gctaacaggg agactaaatt aggaaaagca ggatatgtta ctaatagagg aagacaaaaa     2100
gttgtcaccc taactgacac aacaaatcag aagactgagt tacaagcaat ttatctagct     2160
ttgcaggatt cgggattaga agtaaacata gtaacagact cacaatatgc attaggaatc     2220
attcaagcac aaccagatca aagtgaatca gagttagtca atcaaataat agagcagtta     2280
ataaaaaagg aaaaggtcta tctggcatgg gtaccagcac acaaaggaat tggaggaaat     2340
gaacaagtag ataaattagt cagtgctgga atcaggaaag tgctagctat gggtggcaag     2400
tggtcaaaaa gtagtgtggt tggatggcct actgtaaggg aaagaatgag acgagctgag     2460
ccagcagcag atggggtggg agcagcatct cgagacctgg aaaaacatgg agcaatcaca     2520
```

```
agtagcaata cagcagctac caatgctgct tgtgcctggc tagaagcaca agaggaggag   2580
gaggtgggtt ttccagtcac acctcaggta cctttaagac caatgactta caaggcagct   2640
gtagatctta gccactttt aaaagaaaag gggggactgg aagggctaat tcactcccaa    2700
cgaagacaag atatccttga tctgtggatc taccacacac aaggctactt ccctgattgg   2760
cagaactaca caccagggcc agggtcaga tatccactga cctttggatg gtgctacaag    2820
ctagtaccag ttgagccaga taaggtagaa gaggccaata aggagagaa caccagcttg    2880 ttacaccctg tgagcctgca tggaatggat gaccctgaga gagaagtgtt agagtggagg   2940
tttgacagcc gcctagcatt tcatcacgtg gcccgagagc tgcatccgga gtacttcaag   3000
aactgcaggc ctatgggtgc gagagcgtca gtattaagcg ggggagaatt agatcgatgg   3060
gaaaaaattc ggttaaggcc agggggaaag aaaaaatata aattaaaaca tatagtatgg   3120
gcaagcaggg agctagaacg attcgcagtt aatcctggcc tgttagaaac atcagaaggc   3180
tgtagacaaa tactgggaca gctacaacca tcccttcaga caggatcaga gaacttaga   3240 tcattatata atacagtagc aaccctctat tgtgtgcatc aaaggataga gataaaagac   3300
accaaggaag ctttagacaa gatagaggaa gagcaaaaca aaagtaagaa aaaagcacag   3360
caagcagcag ctgacacagg acacagcaat caggtcagcc aaaattacta a            3411
```

<210> SEQ ID NO 15
<211> LENGTH: 1136
<212> TYPE: PRT
<213> ORGANISM: Artificial Sequence
<220> FEATURE:
<223> OTHER INFORMATION: p24-RT*-Nef-p17 (F4*)

<400> SEQUENCE: 15

```
Met Val Ile Val Gln Asn Ile Gln Gly Gln Met Val His Gln Ala Ile
 1               5                  10                  15

Ser Pro Arg Thr Leu Asn Ala Trp Val Lys Val Val Glu Glu Lys Ala
             20                  25                  30

Phe Ser Pro Glu Val Ile Pro Met Phe Ser Ala Leu Ser Glu Gly Ala
         35                  40                  45

Thr Pro Gln Asp Leu Asn Thr Met Leu Asn Thr Val Gly Gly His Gln
     50                  55                  60

Ala Ala Met Gln Met Leu Lys Glu Thr Ile Asn Glu Glu Ala Ala Glu
 65                  70                  75                  80

Trp Asp Arg Val His Pro Val His Ala Gly Pro Ile Ala Pro Gly Gln
                 85                  90                  95

Met Arg Glu Pro Arg Gly Ser Asp Ile Ala Gly Thr Thr Ser Thr Leu
            100                 105                 110

Gln Glu Gln Ile Gly Trp Met Thr Asn Asn Pro Pro Ile Pro Val Gly
        115                 120                 125

Glu Ile Tyr Lys Arg Trp Ile Ile Leu Gly Leu Asn Lys Ile Val Arg
    130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
        195                 200                 205
```

-continued

```
Ala Ala Thr Leu Glu Glu Met Met Thr Ala Cys Gln Gly Val Gly Gly
            210                 215                 220
Pro Gly His Lys Ala Arg Val Leu His Met Gly Pro Ile Ser Pro Ile
225                 230                 235                 240
Glu Thr Val Ser Val Lys Leu Lys Pro Gly Met Asp Gly Pro Lys Val
                245                 250                 255
Lys Gln Trp Pro Leu Thr Glu Glu Lys Ile Lys Ala Leu Val Glu Ile
                260                 265                 270
Cys Thr Glu Met Glu Lys Glu Gly Lys Ile Ser Lys Ile Gly Pro Glu
            275                 280                 285
Asn Pro Tyr Asn Thr Pro Val Phe Ala Ile Lys Lys Lys Asp Ser Thr
290                 295                 300
Lys Trp Arg Lys Leu Val Asp Phe Arg Glu Leu Asn Lys Arg Thr Gln
305                 310                 315                 320
Asp Phe Trp Glu Val Gln Leu Gly Ile Pro His Pro Ala Gly Leu Lys
                325                 330                 335
Lys Lys Lys Ser Val Thr Val Leu Asp Val Gly Asp Ala Tyr Phe Ser
                340                 345                 350
Val Pro Leu Asp Glu Asp Phe Arg Lys Tyr Thr Ala Phe Thr Ile Pro
            355                 360                 365
Ser Ile Asn Asn Glu Thr Pro Gly Ile Arg Tyr Gln Tyr Asn Val Leu
370                 375                 380
Pro Gln Gly Trp Lys Gly Ser Pro Ala Ile Phe Gln Ser Ser Met Thr
385                 390                 395                 400
Lys Ile Leu Glu Pro Phe Arg Lys Gln Asn Pro Asp Ile Val Ile Tyr
                405                 410                 415
Gln Tyr Met Asp Asp Leu Tyr Val Gly Ser Asp Leu Glu Ile Gly Gln
            420                 425                 430
His Arg Thr Lys Ile Glu Glu Leu Arg Gln His Leu Leu Arg Trp Gly
            435                 440                 445
Leu Thr Thr Pro Asp Lys Lys His Gln Lys Glu Pro Pro Phe Leu Lys
450                 455                 460
Met Gly Tyr Glu Leu His Pro Asp Lys Trp Thr Val Gln Pro Ile Val
465                 470                 475                 480
Leu Pro Glu Lys Asp Ser Trp Thr Val Asn Asp Ile Gln Lys Leu Val
                485                 490                 495
Gly Lys Leu Asn Trp Ala Ser Gln Ile Tyr Pro Gly Ile Lys Val Arg
            500                 505                 510
Gln Leu Cys Lys Leu Leu Arg Gly Thr Lys Ala Leu Thr Glu Val Ile
            515                 520                 525
Pro Leu Thr Glu Glu Ala Glu Leu Glu Leu Ala Glu Asn Arg Glu Ile
            530                 535                 540
Leu Lys Glu Pro Val His Gly Val Tyr Tyr Asp Pro Ser Lys Asp Leu
545                 550                 555                 560
Ile Ala Glu Ile Gln Lys Gln Gly Gln Gly Gln Trp Thr Tyr Gln Ile
                565                 570                 575
Tyr Gln Glu Pro Phe Lys Asn Leu Lys Thr Gly Lys Tyr Ala Arg Lys
            580                 585                 590
Arg Gly Ala His Thr Asn Asp Val Lys Gln Leu Thr Glu Ala Val Gln
            595                 600                 605
Lys Ile Thr Thr Glu Ser Ile Val Ile Trp Gly Lys Thr Pro Lys Phe
            610                 615                 620
Lys Leu Pro Ile Gln Lys Glu Thr Trp Glu Thr Trp Trp Thr Glu Tyr
```

```
                625                 630                 635                 640
Trp Gln Ala Thr Trp Ile Pro Glu Trp Glu Phe Val Asn Thr Pro Pro
                645                 650                 655
Leu Val Lys Leu Trp Tyr Gln Leu Glu Lys Glu Pro Ile Val Gly Ala
                660                 665                 670
Glu Thr Phe Tyr Val Asp Gly Ala Ala Asn Arg Glu Thr Lys Leu Gly
                675                 680                 685
Lys Ala Gly Tyr Val Thr Asn Arg Gly Arg Gln Lys Val Val Thr Leu
                690                 695                 700
Thr Asp Thr Thr Asn Gln Lys Thr Glu Leu Gln Ala Ile Tyr Leu Ala
705                 710                 715                 720
Leu Gln Asp Ser Gly Leu Glu Val Asn Ile Val Thr Asp Ser Gln Tyr
                725                 730                 735
Ala Leu Gly Ile Ile Gln Ala Gln Pro Asp Gln Ser Glu Ser Glu Leu
                740                 745                 750
Val Asn Gln Ile Ile Glu Gln Leu Ile Lys Lys Glu Lys Val Tyr Leu
                755                 760                 765
Ala Trp Val Pro Ala His Lys Gly Ile Gly Gly Asn Glu Gln Val Asp
                770                 775                 780
Lys Leu Val Ser Ala Gly Ile Arg Lys Val Leu Ala Met Gly Gly Lys
785                 790                 795                 800
Trp Ser Lys Ser Ser Val Val Gly Trp Pro Thr Val Arg Glu Arg Met
                805                 810                 815
Arg Arg Ala Glu Pro Ala Ala Asp Gly Val Gly Ala Ala Ser Arg Asp
                820                 825                 830
Leu Glu Lys His Gly Ala Ile Thr Ser Ser Asn Thr Ala Ala Thr Asn
                835                 840                 845
Ala Ala Cys Ala Trp Leu Glu Ala Gln Glu Glu Glu Val Gly Phe
850                 855                 860
Pro Val Thr Pro Gln Val Pro Leu Arg Pro Met Thr Tyr Lys Ala Ala
865                 870                 875                 880
Val Asp Leu Ser His Phe Leu Lys Glu Lys Gly Gly Leu Glu Gly Leu
                885                 890                 895
Ile His Ser Gln Arg Arg Gln Asp Ile Leu Asp Leu Trp Ile Tyr His
                900                 905                 910
Thr Gln Gly Tyr Phe Pro Asp Trp Gln Asn Tyr Thr Pro Gly Pro Gly
                915                 920                 925
Val Arg Tyr Pro Leu Thr Phe Gly Trp Cys Tyr Lys Leu Val Pro Val
                930                 935                 940
Glu Pro Asp Lys Val Glu Glu Ala Asn Lys Gly Glu Asn Thr Ser Leu
945                 950                 955                 960
Leu His Pro Val Ser Leu His Gly Met Asp Asp Pro Glu Arg Glu Val
                965                 970                 975
Leu Glu Trp Arg Phe Asp Ser Arg Leu Ala Phe His His Val Ala Arg
                980                 985                 990
Glu Leu His Pro Glu Tyr Phe Lys Asn Cys Arg Pro Met Gly Ala Arg
                995                 1000                1005
Ala Ser Val Leu Ser Gly Gly Glu Leu Asp Arg Trp Glu Lys Ile Arg
                1010                1015                1020
Leu Arg Pro Gly Gly Lys Lys Lys Tyr Lys Leu Lys His Ile Val Trp
1025                1030                1035                1040
Ala Ser Arg Glu Leu Glu Arg Phe Ala Val Asn Pro Gly Leu Leu Glu
                1045                1050                1055
```

```
Thr Ser Glu Gly Cys Arg Gln Ile Leu Gly Gln Leu Gln Pro Ser Leu
            1060                1065                1070

Gln Thr Gly Ser Glu Glu Leu Arg Ser Leu Tyr Asn Thr Val Ala Thr
        1075                1080                1085

Leu Tyr Cys Val His Gln Arg Ile Glu Ile Lys Asp Thr Lys Glu Ala
    1090                1095                1100

Leu Asp Lys Ile Glu Glu Glu Gln Asn Lys Ser Lys Lys Lys Ala Gln
1105                1110                1115                1120

Gln Ala Ala Ala Asp Thr Gly His Ser Asn Gln Val Ser Gln Asn Tyr
                1125                1130                1135

<210> SEQ ID NO 16
<211> LENGTH: 2313
<212> TYPE: DNA
<213> ORGANISM: Artificial Sequence
<220> FEATURE:
<223> OTHER INFORMATION: p17-p51*-Nef (F3*)

<400> SEQUENCE: 16
```

| | | | | | |
|---|---|---|---|---|---|
| atgggtgcga | gagcgtcagt | attaagcggg | ggagaattag | atcgatggga | aaaaattcgg | 60 |
| ttaaggccag | ggggaaagaa | aaaatataaa | ttaaaacata | tagtatgggc | aagcagggag | 120 |
| ctagaacgat | tcgcagttaa | tcctggcctg | ttagaaacat | cagaaggctg | tagacaaata | 180 |
| ctgggacagc | tacaaccatc | ccttcagaca | ggatcagaag | aacttagatc | attatataat | 240 |
| acagtagcaa | ccctctattg | tgtgcatcaa | aggatagaga | taaaagacac | caaggaagct | 300 |
| ttagacaaga | tagaggaaga | gcaaaacaaa | agtaagaaaa | agcacagca | agcagcagct | 360 |
| gacacaggac | acagcaatca | ggtcagccaa | aattacctcg | acaggactgg | tccgatctct | 420 |
| ccgatagaaa | cagtttcggt | caagcttaaa | ccagggatgg | atggtccaaa | ggtcaagcag | 480 |
| tggccgctaa | cggaagagaa | gattaaggcg | ctcgtagaga | tttgtactga | atggagaag | 540 |
| gaaggcaaga | taagcaagat | cgggccagag | aacccgtaca | atacaccggt | atttgcaata | 600 |
| aagaagaagg | attcaacaaa | atggcgaaag | cttgtagatt | ttagggaact | aaacaagcga | 660 |
| acccaagact | tttgggaagt | ccaactaggt | atcccacatc | cagccggtct | aaagaagaag | 720 |
| aaaatcggtca | cagtcctgga | tgtaggagac | gcatattta | tgtaccgct | tgatgaggac | 780 |
| ttccgaaagt | atactgcgtt | tactataccg | agcataaaca | atgaaacgcc | aggcattcgc | 840 |
| tatcagtaca | acgtgctccc | gcagggctgg | aaggggtctc | cggcgatatt | tcagagctct | 900 |
| atgacaaaaa | tacttgaacc | attccgaaag | cagaatccgg | atattgtaat | ttaccaatac | 960 |
| atggacgatc | tctatgtggg | ctcggatcta | gaaattgggc | agcatcgcac | taagattgag | 1020 |
| gaactgaggc | aacatctgct | tcgatggggc | ctcactactc | ccgacaagaa | gcaccagaag | 1080 |
| gagccgccgt | tcctaaagat | gggctacgag | cttcatccgg | acaagtggac | agtacagccg | 1140 |
| atagtgctgc | cgaaaaagga | ttcttggacc | gtaaatgata | tcagaaaact | agtcggcaag | 1200 |
| cttaactggg | cctctcagat | ttacccaggc | attaaggtcc | gacagctttg | caagctactg | 1260 |
| aggggaacta | aggctctaac | agaggtcatc | ccattaacgg | aggaagcaga | gcttgagctg | 1320 |
| gcagagaatc | gcgaaattct | taaggagccg | gtgcacaggg | tatactacga | cccctccaag | 1380 |
| gaccttatag | ccgagatcca | gaagcagggg | cagggccaat | ggacgtacca | gatatatcaa | 1440 |
| gaaccgtta | agaatctgaa | gactgggaag | tacgcgcgca | acgaggggc | tcatactaat | 1500 |
| gatgtaaagc | aacttacgga | agcagtacaa | aagattacta | ctgagtctat | tgtgatatgg | 1560 |
| ggcaagaccc | caaagttcaa | gctgcccata | cagaaggaaa | catgggaaac | atggtggact | 1620 |

```
gaatattggc aagctacctg gattccagaa tgggaatttg tcaacacgcc gccgctggta    1680
aaactgaggc ctatgggtgg caagtggtca aaaagtagtg tggttggatg cctactgta    1740 agggaaagaa tgagacgagc tgagccagca gcagatgggg tgggagcagc atctcgagac    1800
ctggaaaaac atggagcaat cacaagtagc aatacagcag ctaccaatgc tgcttgtgcc    1860
tggctagaag cacaagagga ggaggaggtg ggttttccag tcacacctca ggtacctta    1920 agaccaatga cttacaaggc agctgtagat cttagccact tttaaaaga aaggggggga    1980 ctggaagggc taattcactc ccaacgaaga caagatatcc ttgatctgtg gatctaccac    2040
acacaaggct acttccctga ttggcagaac tacacaccag ggccagggt cagatatcca    2100 ctgacctttg gatggtgcta caagctagta ccagttgagc cagataaggt agaagaggcc    2160
aataaaggag agaacaccag cttgttacac cctgtgagcc tgcatggaat ggatgaccct    2220
gagagagaag tgttagagtg gaggtttgac agccgcctag catttcatca cgtggcccga    2280
gagctgcatc cggagtactt caagaactgc taa                                2313
```

<210> SEQ ID NO 17
<211> LENGTH: 770
<212> TYPE: PRT
<213> ORGANISM: Artificial Sequence
<220> FEATURE:
<223> OTHER INFORMATION: p17-p51-Nef (F3)

<400> SEQUENCE: 17

```
Met Gly Ala Arg Ala Ser Val Leu Ser Gly Gly Glu Leu Asp Arg Trp
 1               5                  10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Leu Asp Arg Thr Gly Pro Ile Ser Pro Ile Glu Thr
    130                 135                 140

Val Ser Val Lys Leu Lys Pro Gly Met Asp Gly Pro Lys Val Lys Gln
145                 150                 155                 160

Trp Pro Leu Thr Glu Glu Lys Ile Lys Ala Leu Val Glu Ile Cys Thr
                165                 170                 175

Glu Met Glu Lys Glu Gly Lys Ile Ser Lys Ile Gly Pro Glu Asn Pro
            180                 185                 190

Tyr Asn Thr Pro Val Phe Ala Ile Lys Lys Lys Asp Ser Thr Lys Trp
        195                 200                 205

Arg Lys Leu Val Asp Phe Arg Glu Leu Asn Lys Arg Thr Gln Asp Phe
    210                 215                 220

Trp Glu Val Gln Leu Gly Ile Pro His Pro Ala Gly Leu Lys Lys Lys
225                 230                 235                 240
```

-continued

```
Lys Ser Val Thr Val Leu Asp Val Gly Asp Ala Tyr Phe Ser Val Pro
            245                 250                 255

Leu Asp Glu Asp Phe Arg Lys Tyr Thr Ala Phe Thr Ile Pro Ser Ile
        260                 265                 270

Asn Asn Glu Thr Pro Gly Ile Arg Tyr Gln Tyr Asn Val Leu Pro Gln
        275                 280                 285

Gly Trp Lys Gly Ser Pro Ala Ile Phe Gln Ser Ser Met Thr Lys Ile
        290                 295                 300

Leu Glu Pro Phe Arg Lys Gln Asn Pro Asp Ile Val Ile Tyr Gln Tyr
305                 310                 315                 320

Met Asp Asp Leu Tyr Val Gly Ser Asp Leu Glu Ile Gly Gln His Arg
                325                 330                 335

Thr Lys Ile Glu Glu Leu Arg Gln His Leu Leu Arg Trp Gly Leu Thr
                340                 345                 350

Thr Pro Asp Lys Lys His Gln Lys Glu Pro Pro Phe Leu Lys Met Gly
            355                 360                 365

Tyr Glu Leu His Pro Asp Lys Trp Thr Val Gln Pro Ile Val Leu Pro
        370                 375                 380

Glu Lys Asp Ser Trp Thr Val Asn Asp Ile Gln Lys Leu Val Gly Lys
385                 390                 395                 400

Leu Asn Trp Ala Ser Gln Ile Tyr Pro Gly Ile Lys Val Arg Gln Leu
                405                 410                 415

Cys Lys Leu Leu Arg Gly Thr Lys Ala Leu Thr Glu Val Ile Pro Leu
            420                 425                 430

Thr Glu Glu Ala Glu Leu Glu Leu Ala Glu Asn Arg Glu Ile Leu Lys
        435                 440                 445

Glu Pro Val His Gly Val Tyr Tyr Asp Pro Ser Lys Asp Leu Ile Ala
        450                 455                 460

Glu Ile Gln Lys Gln Gly Gln Gly Gln Trp Thr Tyr Gln Ile Tyr Gln
465                 470                 475                 480

Glu Pro Phe Lys Asn Leu Lys Thr Gly Lys Tyr Ala Arg Met Arg Gly
                485                 490                 495

Ala His Thr Asn Asp Val Lys Gln Leu Thr Glu Ala Val Gln Lys Ile
            500                 505                 510

Thr Thr Glu Ser Ile Val Ile Trp Gly Lys Thr Pro Lys Phe Lys Leu
        515                 520                 525

Pro Ile Gln Lys Glu Thr Trp Glu Thr Trp Trp Thr Glu Tyr Trp Gln
        530                 535                 540

Ala Thr Trp Ile Pro Glu Trp Glu Phe Val Asn Thr Pro Pro Leu Val
545                 550                 555                 560

Lys Leu Arg Pro Met Gly Gly Lys Trp Ser Lys Ser Val Val Gly
                565                 570                 575

Trp Pro Thr Val Arg Glu Arg Met Arg Arg Ala Glu Pro Ala Ala Asp
                580                 585                 590

Gly Val Gly Ala Ala Ser Arg Asp Leu Glu Lys His Gly Ala Ile Thr
            595                 600                 605

Ser Ser Asn Thr Ala Ala Thr Asn Ala Ala Cys Ala Trp Leu Glu Ala
        610                 615                 620

Gln Glu Glu Glu Glu Val Gly Phe Pro Val Thr Pro Gln Val Pro Leu
625                 630                 635                 640

Arg Pro Met Thr Tyr Lys Ala Ala Val Asp Leu Ser His Phe Leu Lys
                645                 650                 655
```

```
Glu Lys Gly Gly Leu Glu Gly Leu Ile His Ser Gln Arg Arg Gln Asp
                660                 665                 670

Ile Leu Asp Leu Trp Ile Tyr His Thr Gln Gly Tyr Phe Pro Asp Trp
        675                 680                 685

Gln Asn Tyr Thr Pro Gly Pro Gly Val Arg Tyr Pro Leu Thr Phe Gly
    690                 695                 700

Trp Cys Tyr Lys Leu Val Pro Val Glu Pro Asp Lys Val Glu Glu Ala
705                 710                 715                 720

Asn Lys Gly Glu Asn Thr Ser Leu Leu His Pro Val Ser Leu His Gly
                725                 730                 735

Met Asp Asp Pro Glu Arg Glu Val Leu Glu Trp Arg Phe Asp Ser Arg
                740                 745                 750

Leu Ala Phe His His Val Ala Arg Glu Leu His Pro Gly Tyr Phe Lys
        755                 760                 765

Asn Cys
    770

<210> SEQ ID NO 18
<211> LENGTH: 3000
<212> TYPE: DNA
<213> ORGANISM: Artificial Sequence
<220> FEATURE:
<223> OTHER INFORMATION: F4(p51)*

<400> SEQUENCE: 18
atggttatcg tgcagaacat ccaggggcaa atggtacatc aggccatatc acctagaact      60
ttaaatgcat gggtaaaagt agtagaagag aaggctttca gcccagaagt aatacccatg     120
ttttcagcat tatcagaagg agccacccca caagatttaa acaccatgct aaacacagtg     180
gggggacatc aagcagccat gcaaatgtta aaagagacca tcaatgagga agctgcagaa     240
tgggatagag tacatccagt gcatgcaggg cctattgcac caggccagat gagagaacca     300
aggggaagtg acatagcagg aactactagt acccttcagg aacaaatagg atggatgaca     360
aataatccac ctatcccagt aggagaaatt tataaaagat ggataatcct gggattaaat     420
aaaatagtaa gaatgtatag ccctaccagc attctggaca taagacaagg accaaaagaa     480
ccttttagag actatgtaga ccggttctat aaaactctaa gagccgagca agcttcacag     540
gaggtaaaaa attggatgac agaaaccttg ttggtccaaa atgcgaaccc agattgtaag     600
actattttaa aagcattggg accagcggct acactagaag aaatgatgac agcatgtcag     660
ggagtaggag gacccggcca taaggcaaga gttttgcata tgaggcctgg tccgatctct     720
ccgatagaaa cagtttcggt caagcttaaa ccagggatgg atggtccaaa ggtcaagcag     780
tggccgctaa cggaagagaa gattaaggcg ctcgtagaga tttgtactga atggagaag     840 gaaggcaaga taagcaagat cgggccagag aacccgtaca atacaccggt atttgcaata     900
aagaagaagg attcaacaaa atggcgaaag cttgtagatt ttagggaact aaacaagcga     960
acccaagact tttgggaagt ccaactaggt atcccacatc cagccggtct aaagaagaag    1020
aaatcggtca gtcctggta tgtaggagac gcatatttta gtgtaccgct tgatgaggac    1080
ttccgaaagt atactgcgtt tactataccg agcataaaca tgaaacgcc aggcattcgc    1140 tatcagtaca acgtgctccc gcagggctgg aaggggtctc cggcgatatt tcagagctct    1200
atgacaaaaa tacttgaacc attccgaaag cagaatccgg atattgtaat ttaccaatac    1260
atggacgatc tctatgtggg ctcggatcta gaaattgggc agcatcgcac taagattgag    1320
gaactgaggc aacatctgct tcgatggggc ctcactactc ccgacaagaa gcaccagaag    1380
```

```
gagccgccgt tcctaaagat gggctacgag cttcatccgg acaagtggac agtacagccg   1440
atagtgctgc ccgaaaagga ttcttggacc gtaaatgata ttcagaaact agtcggcaag   1500
cttaactggg cctctcagat ttacccaggc attaaggtcc gacagctttg caagctactg   1560
aggggaacta aggctctaac agaggtcatc ccattaacgg aggaagcaga gcttgagctg   1620
gcagagaatc gcgaaattct taaggagccg gtgcacaggg tatactacga ccccctccaag  1680 gaccttatag ccgagatcca gaagcagggg cagggccaat ggacgtacca gatatatcaa   1740
gaaccgttta agaatctgaa gactgggaag tacgcgcgca acgagggggc tcatactaat   1800
gatgtaaagc aacttacgga agcagtacaa aagattacta ctgagtctat tgtgatatgg   1860
ggcaagaccc caaagttcaa gctgcccata cagaaggaaa catgggaaac atggtggact   1920
gaatattggc aagctacctg gattccagaa tgggaatttg tcaacacgcc gccgctggta   1980
aaactggccc tagctatggg tggcaagtgg tcaaaaagta gtgtggttgg atggcctact   2040
gtaagggaaa gaatgagacg agctgagcca gcagcagatg gggtgggagc agcatctcga   2100
gacctggaaa acatggagc aatcacaagt agcaatacag cagctaccaa tgctgcttgt   2160
gcctggctag aagcacaaga ggaggaggag gtgggtttc cagtcacacc tcaggtacct   2220
ttaagaccaa tgacttacaa ggcagctgta gatcttagcc actttttaaa agaaaagggg   2280
ggactggaag ggctaattca ctcccaacga agacaagata tccttgatct gtggatctac   2340
cacacacaag gctacttccc tgattggcag aactacacac cagggccagg ggtcagatat   2400
ccactgacct ttggatggtg ctacaagcta gtaccagttg agccagataa ggtagaagag   2460
gccaataaag gagagaacac cagcttgtta caccctgtga gcctgcatgg aatggatgac   2520
cctgagagag aagtgttaga gtggaggttt gacagccgcc tagcatttca tcacgtggcc   2580
cgagagctgc atccggagta cttcaagaac tgcaggccta tgggtgcgag agcgtcagta   2640
ttaagcgggg gagaattaga tcgatgggaa aaaattcggt taaggccagg ggaaagaaa   2700 aaatataaat taaaacatat agtatgggca agcagggagc tagaacgatt cgcagttaat   2760
cctggcctgt tagaaacatc agaaggctgt agacaaatac tgggacagct acaaccatcc   2820
cttcagacag gatcagaaga acttagatca ttatataata cagtagcaac cctctattgt   2880
gtgcatcaaa ggatagagat aaaagacacc aaggaagctt tagacaagat agaggaagag   2940
caaaacaaaa gtaagaaaaa agcacagcaa gcagcagctg acacaggaca cagcaatcag   3000
```

<210> SEQ ID NO 19
<211> LENGTH: 1005
<212> TYPE: PRT
<213> ORGANISM: Artificial Sequence
<220> FEATURE:
<223> OTHER INFORMATION: F4(p51)*

<400> SEQUENCE: 19

```
Met Val Ile Val Gln Asn Ile Gln Gly Gln Met Val His Gln Ala Ile
1               5                   10                  15

Ser Pro Arg Thr Leu Asn Ala Trp Val Lys Val Glu Glu Lys Ala
            20                  25                  30

Phe Ser Pro Glu Val Ile Pro Met Phe Ser Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Glu Thr Ile Asn Glu Glu Ala Ala Glu
65                  70                  75                  80
```

```
Trp Asp Arg Val His Pro Val His Ala Gly Pro Ile Ala Pro Gly Gln
                85                  90                  95

Met Arg Glu Pro Arg Gly Ser Asp Ile Ala Gly Thr Ser Thr Leu
            100                 105                 110

Gln Glu Gln Ile Gly Trp Met Thr Asn Asn Pro Pro Ile Pro Val Gly
            115                 120                 125

Glu Ile Tyr Lys Arg Trp Ile Ile Leu Gly Leu Asn Lys Ile Val Arg
            130                 135                 140

Met Tyr Ser Pro Thr Ser Ile Leu Asp Ile Arg Gln Gly Pro Lys Glu
145                 150                 155                 160

Pro Phe Arg Asp Tyr Val Asp Arg Phe Tyr Lys Thr Leu Arg Ala Glu
                165                 170                 175

Gln Ala Ser Gln Glu Val Lys Asn Trp Met Thr Glu Thr Leu Leu Val
            180                 185                 190

Gln Asn Ala Asn Pro Asp Cys Lys Thr Ile Leu Lys Ala Leu Gly Pro
            195                 200                 205

Ala Ala Thr Leu Glu Glu Met Met Thr Ala Cys Gln Gly Val Gly Gly
            210                 215                 220

Pro Gly His Lys Ala Arg Val Leu His Met Arg Pro Gly Pro Ile Ser
225                 230                 235                 240

Pro Ile Glu Thr Val Ser Val Lys Leu Lys Pro Gly Met Asp Gly Pro
                245                 250                 255

Lys Val Lys Gln Trp Pro Leu Thr Glu Glu Lys Ile Lys Ala Leu Val
            260                 265                 270

Glu Ile Cys Thr Glu Met Glu Lys Glu Gly Lys Ile Ser Lys Ile Gly
            275                 280                 285

Pro Glu Asn Pro Tyr Asn Thr Pro Val Phe Ala Ile Lys Lys Lys Asp
            290                 295                 300

Ser Thr Lys Trp Arg Lys Leu Val Asp Phe Arg Glu Leu Asn Lys Arg
305                 310                 315                 320

Thr Gln Asp Phe Trp Glu Val Gln Leu Gly Ile Pro His Pro Ala Gly
                325                 330                 335

Leu Lys Lys Lys Lys Ser Val Thr Val Leu Asp Val Gly Asp Ala Tyr
            340                 345                 350

Phe Ser Val Pro Leu Asp Glu Asp Phe Arg Lys Tyr Thr Ala Phe Thr
            355                 360                 365

Ile Pro Ser Ile Asn Asn Glu Thr Pro Gly Ile Arg Tyr Gln Tyr Asn
            370                 375                 380

Val Leu Pro Gln Gly Trp Lys Gly Ser Pro Ala Ile Phe Gln Ser Ser
385                 390                 395                 400

Met Thr Lys Ile Leu Glu Pro Phe Arg Lys Gln Asn Pro Asp Ile Val
                405                 410                 415

Ile Tyr Gln Tyr Met Asp Asp Leu Tyr Val Gly Ser Asp Leu Glu Ile
            420                 425                 430

Gly Gln His Arg Thr Lys Ile Glu Glu Leu Arg Gln His Leu Leu Arg
            435                 440                 445

Trp Gly Leu Thr Thr Pro Asp Lys Lys His Gln Lys Glu Pro Pro Phe
            450                 455                 460

Leu Lys Met Gly Tyr Glu Leu His Pro Asp Lys Trp Thr Val Gln Pro
465                 470                 475                 480

Ile Val Leu Pro Glu Lys Asp Ser Trp Thr Val Asn Asp Ile Gln Lys
                485                 490                 495
```

-continued

```
Leu Val Gly Lys Leu Asn Trp Ala Ser Gln Ile Tyr Pro Gly Ile Lys
        500                 505                 510
Val Arg Gln Leu Cys Lys Leu Leu Arg Gly Thr Lys Ala Leu Thr Glu
    515                 520                 525
Val Ile Pro Leu Thr Glu Glu Ala Glu Leu Glu Leu Ala Glu Asn Arg
530                 535                 540
Glu Ile Leu Lys Glu Pro Val His Gly Val Tyr Tyr Asp Pro Ser Lys
545                 550                 555                 560
Asp Leu Ile Ala Glu Ile Gln Lys Gln Gly Gln Gly Gln Trp Thr Tyr
                565                 570                 575
Gln Ile Tyr Gln Glu Pro Phe Lys Asn Leu Lys Thr Gly Lys Tyr Ala
            580                 585                 590
Arg Lys Arg Gly Ala His Thr Asn Asp Val Lys Gln Leu Thr Glu Ala
        595                 600                 605
Val Gln Lys Ile Thr Thr Glu Ser Ile Val Ile Trp Gly Lys Thr Pro
    610                 615                 620
Lys Phe Lys Leu Pro Ile Gln Lys Glu Thr Trp Glu Thr Trp Trp Thr
625                 630                 635                 640
Glu Tyr Trp Gln Ala Thr Trp Ile Pro Glu Trp Glu Phe Val Asn Thr
                645                 650                 655
Pro Pro Leu Val Lys Leu Ala Leu Ala Met Gly Gly Lys Trp Ser Lys
            660                 665                 670
Ser Ser Val Val Gly Trp Pro Thr Val Arg Glu Arg Met Arg Arg Ala
        675                 680                 685
Glu Pro Ala Ala Asp Gly Val Gly Ala Ala Ser Arg Asp Leu Glu Lys
    690                 695                 700
His Gly Ala Ile Thr Ser Ser Asn Thr Ala Ala Thr Asn Ala Ala Cys
705                 710                 715                 720
Ala Trp Leu Glu Ala Gln Glu Glu Glu Val Gly Phe Pro Val Thr
                725                 730                 735
Pro Gln Val Pro Leu Arg Pro Met Thr Tyr Lys Ala Ala Val Asp Leu
            740                 745                 750
Ser His Phe Leu Lys Glu Lys Gly Gly Leu Glu Gly Leu Ile His Ser
        755                 760                 765
Gln Arg Arg Gln Asp Ile Leu Asp Leu Trp Ile Tyr His Thr Gln Gly
    770                 775                 780
Tyr Phe Pro Asp Trp Gln Asn Tyr Thr Pro Gly Pro Gly Val Arg Tyr
785                 790                 795                 800
Pro Leu Thr Phe Gly Trp Cys Tyr Lys Leu Val Pro Val Glu Pro Asp
                805                 810                 815
Lys Val Glu Glu Ala Asn Lys Gly Glu Asn Thr Ser Leu Leu His Pro
            820                 825                 830
Val Ser Leu His Gly Met Asp Asp Pro Glu Arg Glu Val Leu Glu Trp
        835                 840                 845
Arg Phe Asp Ser Arg Leu Ala Phe His His Val Ala Arg Glu Leu His
    850                 855                 860
Pro Glu Tyr Phe Lys Asn Cys Arg Pro Met Gly Ala Arg Ala Ser Val
865                 870                 875                 880
Leu Ser Gly Gly Glu Leu Asp Arg Trp Glu Lys Ile Arg Leu Arg Pro
                885                 890                 895
Gly Gly Lys Lys Lys Tyr Lys Leu Lys His Ile Val Trp Ala Ser Arg
            900                 905                 910
Glu Leu Glu Arg Phe Ala Val Asn Pro Gly Leu Leu Glu Thr Ser Glu
```

-continued

```
                915                 920                 925
Gly Cys Arg Gln Ile Leu Gly Gln Leu Gln Pro Ser Leu Gln Thr Gly
    930                 935                 940

Ser Glu Glu Leu Arg Ser Leu Tyr Asn Thr Val Ala Thr Leu Tyr Cys
945                 950                 955                 960

Val His Gln Arg Ile Glu Ile Lys Asp Thr Lys Glu Ala Leu Asp Lys
                965                 970                 975

Ile Glu Glu Glu Gln Asn Lys Ser Lys Lys Ala Gln Gln Ala Ala
                980                 985                 990

Ala Asp Thr Gly His Ser Asn Gln Val Ser Gln Asn Tyr
        995                 1000                1005

<210> SEQ ID NO 20
<211> LENGTH: 6
<212> TYPE: PRT
<213> ORGANISM: Artificial Sequence
<220> FEATURE:
<223> OTHER INFORMATION: Artificial Linker

<400> SEQUENCE: 20

Gly Ser Gly Gly Gly Pro
1               5
```